(12) United States Patent
Williams et al.

(10) Patent No.: US 11,279,752 B2
(45) Date of Patent: *Mar. 22, 2022

(54) TUMOR-SELECTIVE CTLA-4 ANTAGONISTS

(71) Applicants: City of Hope, Duarte, CA (US);
Thomas Jefferson University, Philadelphia, PA (US)

(72) Inventors: John C. Williams, Monrovia, CA (US);
Ulrich Rodeck, Philadelphia, PA (US);
Kurt Jenkins, Duarte, CA (US)

(73) Assignees: CITY OF HOPE, Duarte, CA (US);
THOMAS JEFFERSON UNIVERSITY, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/559,561

(22) Filed: Sep. 3, 2019

(65) Prior Publication Data
US 2020/0325212 A1 Oct. 15, 2020

Related U.S. Application Data

(63) Continuation of application No. 15/322,438, filed as application No. PCT/US2015/039103 on Jul. 2, 2015, now Pat. No. 10,414,814.

(60) Provisional application No. 62/020,806, filed on Jul. 3, 2014.

(51) Int. Cl.
| | |
|---|---|
| C07K 14/82 | (2006.01) |
| C07K 16/28 | (2006.01) |
| C07K 14/47 | (2006.01) |
| C07K 14/705 | (2006.01) |
| C07K 14/71 | (2006.01) |
| C12N 9/64 | (2006.01) |

(52) U.S. Cl.
CPC ............ *C07K 14/82* (2013.01); *C07K 14/47* (2013.01); *C07K 14/70521* (2013.01); *C07K 14/70596* (2013.01); *C07K 14/71* (2013.01); *C07K 16/2818* (2013.01); *C12N 9/6491* (2013.01); *C07K 2317/35* (2013.01); *C07K 2317/622* (2013.01); *C07K 2317/76* (2013.01); *C07K 2317/92* (2013.01); *C07K 2318/20* (2013.01); *C07K 2319/30* (2013.01); *C07K 2319/50* (2013.01)

(58) Field of Classification Search
CPC .. C07K 14/82; C07K 14/47; C07K 14/70521; C07K 14/70596; C07K 14/71; C07K 16/2818; C07K 2317/35; C07K 2317/622; C07K 2317/76; C07K 2317/92; C07K 2318/20; C07K 2319/30; C07K 2319/50; C12N 9/6491; A61P 35/00
See application file for complete search history.

(56) References Cited

U.S. PATENT DOCUMENTS

| | | | |
|---|---|---|---|
| 4,676,980 A | 6/1987 | Segal et al. | |
| 4,816,567 A | 3/1989 | Cabilly et al. | |
| 4,861,760 A | 8/1989 | Mazuel et al. | |
| 4,911,920 A | 3/1990 | Jani et al. | |
| 4,946,778 A | 8/1990 | Ladner et al. | |
| 5,212,162 A | 5/1993 | Missel et al. | |
| 5,403,841 A | 4/1995 | Lang et al. | |
| 5,530,101 A | 6/1996 | Queen et al. | |
| 5,545,806 A | 8/1996 | Longberg et al. | |
| 5,545,807 A | 8/1996 | Surani et al. | |
| 5,569,825 A | 10/1996 | Longberg et al. | |
| 5,585,089 A | 12/1996 | Queen et al. | |
| 5,625,126 A | 4/1997 | Longberg et al. | |
| 5,633,425 A | 5/1997 | Longberg et al. | |
| 5,661,016 A | 8/1997 | Longberg et al. | |
| 5,693,761 A | 12/1997 | Queen et al. | |
| 5,693,762 A | 12/1997 | Queen et al. | |
| 5,777,085 A | 7/1998 | Co et al. | |
| 5,847,082 A * | 12/1998 | Rother ................ | C07K 14/005 530/350 |
| 5,859,205 A | 1/1999 | Adair et al. | |
| 6,180,370 B1 | 1/2001 | Queen et al. | |
| 6,210,671 B1 | 4/2001 | Co | |
| 6,329,511 B1 | 12/2001 | Vasquez et al. | |
| 7,754,208 B2 * | 7/2010 | Ledbetter ................ | A61P 19/02 424/133.1 |
| 8,883,982 B2 * | 11/2014 | Seehra ............. | C07K 14/70521 530/387.3 |
| 10,414,814 B2 * | 9/2019 | Williams ............. | C12N 9/6491 |

(Continued)

FOREIGN PATENT DOCUMENTS

| | | | |
|---|---|---|---|
| CN | 103232542 A | * | 8/2013 |
| EP | 0173494 A3 | | 11/1987 |

(Continued)

OTHER PUBLICATIONS

Al-Muhammed et al., "In-vivo studies on dexamethasone sodium phosphate liposomes," J Microencapsul (1996) 13 (3):293-306.

(Continued)

*Primary Examiner* — Phuong Huynh

(74) *Attorney, Agent, or Firm* — Mintz, Levin, Cohn, Ferris, Glovsky and Popeo, P.C.

(57) ABSTRACT

Provided herein are recombinant masking proteins and recombinant ligand proteins useful in treating cancer, neurodegenerative disease, and cardiovascular disease. The recombinant masking proteins provided herein may, inter alia, be used as non-covalent masks of antagonists of, for example, cellular growth factors (e.g., TNF) or cell surface proteins (e.g., CTLA-4).

10 Claims, 12 Drawing Sheets

Specification includes a Sequence Listing.

(56) References Cited

U.S. PATENT DOCUMENTS

| | | |
|---|---|---|
| 2009/0042785 A1 | 2/2009 | Matschiner et al. |
| 2010/0189651 A1 | 7/2010 | Stagliano et al. |
| 2010/0221212 A1 | 9/2010 | Stagliano et al. |
| 2011/0178279 A1 | 7/2011 | Williams et al. |
| 2013/0060010 A1 | 3/2013 | Williams et al. |

FOREIGN PATENT DOCUMENTS

| | | |
|---|---|---|
| WO | WO-87/02671 A1 | 5/1987 |
| WO | WO-91/00360 A1 | 1/1991 |
| WO | WO-92/00373 A1 | 1/1992 |
| WO | WO-93/08829 A1 | 5/1993 |
| WO | WO-96/05309 A3 | 3/1996 |

OTHER PUBLICATIONS

Arnon et al.(Jan. 1, 1985) "Monoclonal Antibodies For Immunotargeting of Drugs In Cancer Therapy" Monoclonal Antibodies and Cancer Therapy, Reisfeld et al. (eds.), pp. 243-256.

Au et al., "Secretory production of bioactive recombinant human granulocyte-macrophage colony-stimulating factor by a baculovirus expression system," J Biotechnol (1996) 51 (2):107-113.

Beck et al., "Enterocolitis in Patients With Cancer After AntibodyBlockade of Cytotoxic T-Lymphocyte—Associated Antigen 4," J Clin Oncol (2006) 24(15):2283-2289.

Charles et al., "Cloning and expression of a rat neuronal nitric oxide synthase coding sequence in a baculovirus/insect cell system," Biochem Biophys Res Commun (1993) 196(3):1481-1489.

Chonn et al., "Recent advances in liposomal drug-delivery systems," Cuff Opin Biotechnol (1995) 6(6):698-708.

Cole et al., "The EBV-hybridoma technique and its application to human lung cancer," Monolclonal Antibodies and Cancer Therapy (1985) 27:77-96.

Curran et al., PD-1 and CTLA-4 combination blockade expandsinfiltrating T cells and reduces regulatory T andmyeloid cells within 816 melanoma tumors:' PNAS (2010) 107(9):4275-4280.

Czajkowsky et al., "Pc-fusion proteins: new developments andfuture perspectives," EMBO Mot Med (2012) 4:1015-1028.

Donaldson et al, "Design and development of masked therapeutic antibodies to limit off-target effects: Application to anti-EGFR antibodies," Cancer Biol Ther (2009) 8(22):2147-2152.

Drake et al., "Androgen ablation mitigates tolerance to a prostate/prostate cancer-restricted antigen," Cancer Cell (2005) 7:239.

Eyles et al., "Oral delivery and fate of poly(lactic acid) microsphere-encapsulated interferon in rats," J Pharm Pharmacol (1997) 49(7):669-674.

Fishwild et al. (Jul. 1996). "High-Avidity Human IgGk Monoclonal Antibodies From A Novel Strain of Minilocus Transgenic Mice," Nature Biotechnology 14:845-851.

Gao et al., "Controlled release of a contraceptive steroid from biodegradable and injectable gel formulations: In vitro evaluation," Pharm Res (1995) 12(6):857-863.

Getnet et al., "Tumor Recognition and Self-Recognition Induce Distinct Transcriptional Profiles in Antigen-Specific CD4 T Cells," J Immunol (2009) 182:4675-4685.

Gregor et al., "CTLA-4 blockade in combination with xenogeneic DNA vaccines enhances T-cell responses, tumor immunity and autoimmunity to self antigens in animal and cellular model systems," Vaccine (2004) 22:1700-1708.

Grosso et al., "LAG-3 regulates CD8+ T cell accumulation and effector function in murine self-and tumor-tolerance systems," J. Clin. Invest (2007) 117:3383-3392.

Hellstrom et al., "Antibodies For Drug Delivery"in Controlled Drug Delivery (2nd Ed.), Robinson et al. (eds.), pp. 623-653 (Marcel Dekker, Inc. 1987).

Hodge et al., "Vaccine Therapy of Established Tumors in the Absenceof Autoimmunity," Clin Can Res (2003) 9:1387-1849.

Hodi et al., "Improved Survival with Ipilimumab in Patients with Metastatic Melanoma," N Engl J Med (2010) 363:711-723.

Jones et al. (May 29, 1986). "Replacing the Complementarity-Determining Regions in a Human Antibody With Those From A Mouse," Nature 321:552-525.

Kohler et al., "Continuous cultures of fused cells secreting antibody of predefined specificity," Nature (1975) 256:495-497.

Kozbor et al. "The production of monoclonal antibodies from human lymphocytes," Immunology Today (1983) 4:72-79.

Kwon et al., "Elimination of residual metastatic prostate cancerafter surgery and adjunctive cytotoxic T lymphocyte-associated antigen 4 (CTLA-4) blockade immunotherapy," PNAS (1999) 96(26): 15074-15079.

Lonberg, N et al. (1995). "Human Antibodies From Transgenic Mice," Intern. Rev. Immunol. 13:65-93.

Lonberg, N et al. (Apr. 28, 1994). "Antigen-Specific Human Antibodies From Mice Comprising Four Distinct Genetic Modifications," Nature 368:856-859.

Marks et al., "By-passing immunization: building high affinity human antibodies by chain shuffling," Biotechnology N. Y. (1992) 10(7):779-783.

Maxwell et al., "Abatacept for rheumatoid arthritis: a Cochrane systematic review," J Rheumatol (2010) 37(2):234-245.

McCafferty et al., "Phage antibodies: filamentous phage displaying antibody variable domains," Nature (1990) 348:552-554.

Morrison et al., "Chimeric human antibody molecules: mouse antigen-binding domains with human constant region domains," PNAS (1984) 81(21):6851-6855.

Morrison et al., "Genetically engineered antibody molecules," Adv Immunol (1989) 44:65-92.

Morrison, "Immunology. Success in specification," Nature (1994) 368(6474):812-813.

Morton et al, "Differential effects of CTLA-4 substitutions on the binding of human CD80 (87-1) and CD86 (87-2)," J Immunol (1996) 156(3)1047-1054.

Ostro et al. "Use of liposomes as injectable-drug delivery systems," Am J Hosp Pharm (1989) 46(8) :1579-1587.

Padlan, "A possible procedure for reducing the immunogenicity of antibody variable domains while preserving their ligand-binding properties," Mol Immunol (1991) 28(4-5):489-498.

Padlan, "Anatomy of the antibody molecule," Mol Immunol (1994) 31 (3):169-217.

Phan et al., "CTLA-4 Blockade with Monoclonal Antibodies in Patientswith Metastatic Cancer: Surgical Issues," Annals of Surgical Oncology (2008) 15(11):3014-3021.

Presta, "Antibody engineering," Curr Opi Struct Biol (1992) 2(4):593-596.

Quezada et al.. "CTLA4 blockade and GM-CSF combination immunotherapy alters the intratumor balance of effector and regulatory T cells," J Clin Invest (2006) 116:1935-1945.

Rao, "Recent developments of collagen-based materials for medical applications and drug delivery systems," J Biomater Sci Polym Ed (1995) 7(7):623-645.

Riechmann, L. et al. (Mar. 24, 1988). "Reshaping Human Antibodies for Therapy," Nature 332:323-327.

Schonfeld et al., "An engineered lipocalin specific for CTLA-4 reveals a combining site with structural and conformationalfeatures similar to antibodies," PNAS (2009) 106(20):8198-8203.

Simmons et al., "Local secretion of anti-CTLA-4 enhances the therapeutic eYcacy of a cancer immunotherapy with reduced evidence of systemic autoimmunity," Cancer Immunol Immunother (2008) 57:1263-1270.

Suresh et al., "Bispecific monoclonal antibodies from hybrid hybridomas," Methods in Enzymology (1986) 121:210-228.

Thorpe et al., "The Preparation And Cytotoxic Properties Of Antibody-Toxin Conjugates," Immunol Rev (1982) 62:119-158.

Traunecker et al., "Bispecific single chain molecules (Janusins) target cytotoxic lymphocytes on HIV infected cells," EMBO j. (1991) 10(12):3655-3659.

Turk et al., "Determination of protease cleavage site motifs using mixture-based oriented peptide libraries," Nat Biotechnol (2001) 19(7):661-667.

Verhoeyen et al., "Reshaping human antibodies: grafting an antilysozyme activity," Science (1988) 239 (4847):1534-1536.

(56) References Cited

OTHER PUBLICATIONS

Waitz et al., "Potent induction of tumor immunity by combining tumor cryoablation with anti-CTLA-4 therapy," Cancer Res (2012) 72(2):430-439.
Waldman, "Annual Progress Report: 2009 Nonformula Grant on Cancer," Vaccines (2011) 1-9.
Weber et al., "Phase I/II Study of 1 pilimumab for Patients WithMetastatic Melanoma," J Clin Oncol (2008) 26 (36):5950-5956.
Winter et al., "Man-made antibodies," Nature (1991) 349:293-299.
Xu et al., "Affinity and cross-reactivity engineering of CTLA4-lg to modulate T cell costimulation," J Immunol (2012) 189 (9):4470-4477.
Zhang et al., "Loss of Keap1 Function in Prostate Cancer Cells Causes Chemoand Radio-resistance and Promotes Tumor Growth," Mol Cancer Ther (2010) 9(2):336.
Igoucheva et al., "Immunotargeting and eradication of orthotopic melanoma using a chemokine-enhanced DNA vaccine," Gene Therapy (2013) 20:939-948.
Burgess, et al., Journal of Cell Biology, vol. 111, pp. 2129-2138 (Year: 1990).
Lazar, et al., Molecular and Cellular Biology, vol. 8, pp. 1247-1252 (Year: 1988).
Skolnick et al., Trends in Biotechnology, 18: 34-39 (Year: 2000).
Jones et al., Pharmacogenomics Journal, 1:126-134 (Year: 2001).
Tosatto et al., Current Pharmaceutical Design, 12:2067-2086 (Year: 2006).
Rudikoff et al., Proc. Natl. Acad. Sci. USA 79:1979 (Year: 1982).
Wu et al., J. Mol. Biol. 294: 151-162 (Year: 1999).

* cited by examiner

A)

| "Fast" mixing | Volume (mL) | Sum A230 (mAU) | Mean A230 | % A230 |
|---|---|---|---|---|
| Peak 1 | 7.6-8.6 | 9171.1 | 195.1 | 25.4% |
| Peak 2 | 8.6-9.6 | 13720.4 | 291.9 | 38.0% |
| Peak 3 | 10.1-11.1 | 13248.5 | 281.9 | 36.7% |

| "Slow" mixing | Volume (mL) | Sum A230 (mAU) | Mean A230 | % A230 |
|---|---|---|---|---|
| Peak 1 | 7.6-8.6 | 4592.6 | 97.7 | 9.7% |
| Peak 2 | 8.6-9.6 | 9696.8 | 206.3 | 20.5% |
| Peak 3 | 10.1-11.1 | 33055 | 703.3 | 69.8% |

TUMOR-SELECTIVE CTLA-4 ANTAGONISTS

CROSS-REFERENCES TO RELATED APPLICATIONS

This application is a continuation application of U.S. application Ser. No. 15/322,438, filed Dec. 27, 2016, now issued as U.S. Pat. No. 10,414,814, which is a National Stage filing of International Application No. PCT/US2010/025926, filed Jul. 2, 2015, which claims the benefit of U.S. Provisional Application No. 62/020,806, filed Jul. 3, 2014, each of which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under Grant Nos. R21 CA135216 and P30 CA033572 awarded by the National Cancer Institute. The Government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048440-530001US_SEQUENCE_LISTING_ST25.TXT, created on May 21, 2020, 53,248 bytes, machine format IBM-PC, MS Windows operating system, is hereby incorporated by reference.

BACKGROUND OF THE INVENTION

Most protein-based targeted therapies currently in use target molecular mechanisms but not disease sites such as monoclonal antibodies which bind to diseased cells or to T cells (as in the case of ipilimumab and the related CTLA-4 antagonist tremelimumab). However, engagement of these targets in normal tissues gives rise to adverse events with various degrees of severity depending on the molecular target. If the therapeutic agent induces autoimmune phenomena the toxicity not only leads to significant morbidity, but also often necessitates the administration of immunosuppressants (corticosteroids, TNF-α inhibitors) which interfere with therapeutic intent.

There is a substantial, unmet need in the clinic to develop targeted therapies with reduced side effects and enhanced efficacy. Often referred to as "magic bullets", monoclonal antibodies (mAbs) preferentially target diseased tissue and are generally better tolerated than traditional chemotherapy. In most cases, therapeutic mAbs bind to an antigen that is 'self' but overexpressed in the tumor, such as the Erbb family members (e.g., EGFR, Her2). However, systemic administration of these mAbs, at therapeutic doses, leads the mAb to engage antigen expressed on normal tissues, and thus, can lead to serious adverse side effects. As an example, the mAbs cetuximab (Erbitux™) and trastuzumab (Herceptin™) that are currently used to treat neck and colon cancers and breast cancer, also give rise to acneiform skin eruptions, gastrointestinal irritation and cardiotoxicity. Serious side effects due to off-target effects have been also been observed with other mAbs, such as efalizumab (Raptiva™). Indeed, the adverse effects of efalizumab in treatment of psoriasis, recently resulted in efalizumab being withdrawn from the market due to the development of progressive multifocal leukoencephalopathy. Adverse side effects of mAbs in clinical use reduce the efficacy of these agents, cause additional, substantial costs related to monitoring these side effects, and ultimately reduce patients' quality of life. In fact, the psychological aspect of the severe skin rashes alone has led patients to discontinue cetuximab, an effective treatment approved for various epithelial malignancies. Thus, there is a need in the art for treatment options which avoid these and other adverse effects. Provided herein are solutions to these and other problems in the art.

BRIEF SUMMARY OF THE INVENTION

Accordingly, herein are provided, inter alia, compositions, kits, and methods for treating diseases using recombinant masking proteins and recombinant ligand proteins.

Provided herein are protein compositions. In one aspect these are recombinant masking proteins including two identical masking protein domains. Each of the masking protein domains includes (1) a masking dimerizing domain; (2) a ligand-masking binding domain; and (3) a cleavable masking linker connecting the ligand-masking binding domain to the masking dimerizing domain. The masking protein domains are bound together.

Also provided herein are pharmaceutical compositions. In one aspect, the pharmaceutical compositions include a pharmaceutically acceptable excipient, a recombinant masking protein as described herein, including embodiments thereof, and a recombinant ligand protein as described herein, including embodiments thereof.

The recombinant protein compositions and pharmaceutical compositions may also be included in kits described herein. In one aspect this is a kit that includes a recombinant masking protein as described herein, including embodiments thereof, and a recombinant ligand protein as described herein, including embodiments thereof.

Provided herein are methods of treating a disease in a subject in need thereof. In one aspect, the method includes administering to a subject a therapeutically effective amount of a recombinant masking protein and a recombinant ligand protein as described herein including embodiments thereof.

DETAILED DESCRIPTION OF THE INVENTION

Figure 1:
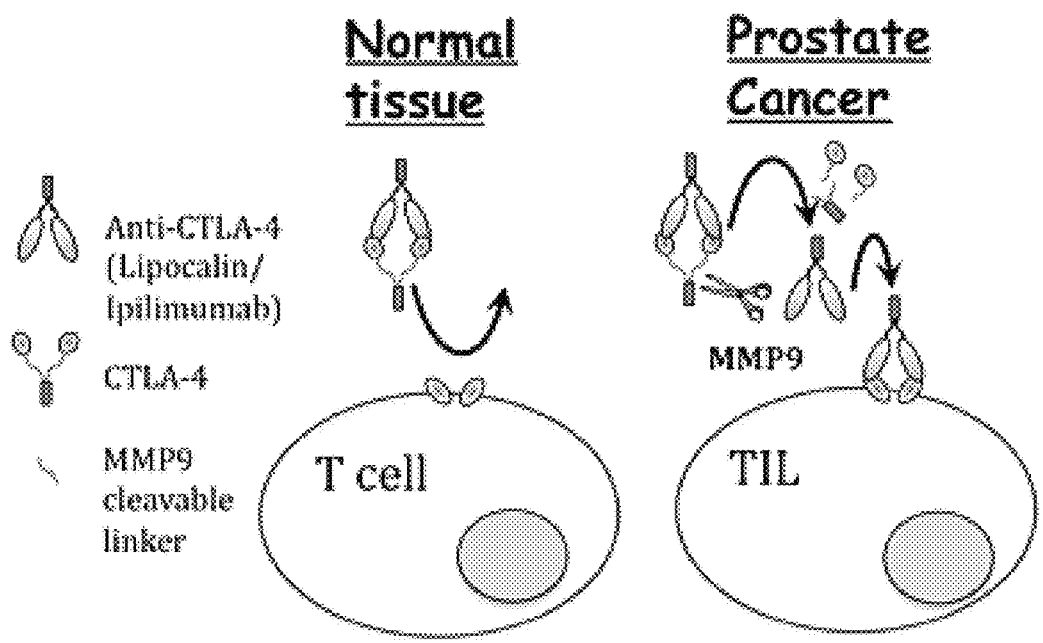
FIG. 1: Predicted mode of action of the masked CTLA-4 antagonist modified lipocalin2 (m-Lcn2): A) In normal tissues M-Lcn2 is masked by the recombinant CTLA-4 fragment tethered to it by N-terminal linkage and hence does not bind to T cells but in prostate cancer tissue, tumor-associated MMP9 cleaves the CTLA-4 mask leading to native CTLA-4 engagement and activation of tumor-infiltrating lymphocytes (TILs) (the design principle can be applied to monovalent or bivalent m-Lcn2 to exploit the avidity gain of such ligands); B) Predicted atomic structure of the bivalent CTLA-4 mask containing an Fc fragment tethered to MMP9-cleavable extensions that consist of CTLA-4-derived peptides that fit the m-Lcn2 binding pocket.
Figure 1:
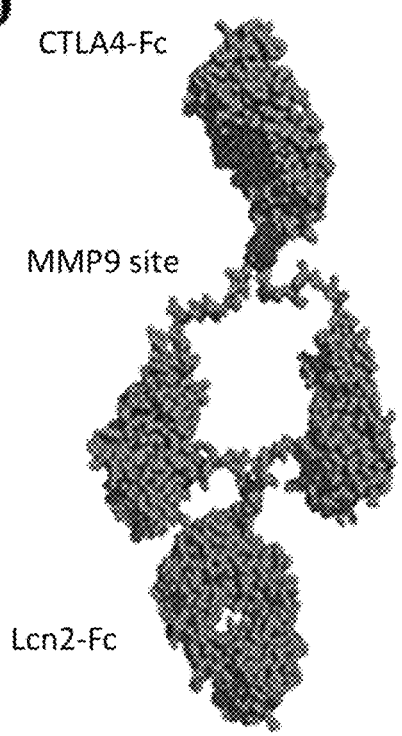

The abbreviations used herein have their conventional meaning within the chemical and biological arts. The chemical structures and formulae set forth herein are constructed according to the standard rules of chemical valency known in the chemical arts.

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer. A "fusion protein" refers to a chimeric protein encoding two or more separate protein sequences that is recombinantly expressed as a single moiety.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids sequences encode any given amino acid residue. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers nucleic acids that have the same basic chemical structure as a naturally occurring nucleic acids. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

"Synthetic mRNA" as used herein refers to any mRNA derived through non-natural means such as standard oligonucleotide synthesis techniques or cloning techniques. Such mRNA may also include non-proteinogenic derivatives of naturally occurring nucleotides. Additionally, "synthetic mRNA" herein also includes mRNA that has been expressed through recombinant techniques or exogenously, using any expression vehicle, including but not limited to prokaryotic cells, eukaryotic cell lines, and viral methods. "Synthetic mRNA" includes such mRNA that has been purified or otherwise obtained from an expression vehicle or system.

The term "modulation", "modulate", or "modulator" are used in accordance with their plain ordinary meaning and refer to the act of changing or varying one or more properties. "Modulator" refers to a composition that increases or decreases the level of a target molecule or the function of a target molecule or the physical state of the target of the molecule. "Modulation" refers to the process of changing or varying one or more properties. For example, as applied to the effects of a modulator on a biological target, to modulate means to change by increasing or decreasing a property or function of the biological target or the amount of the biological target.

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In embodiments inhibition refers to reduction of a disease or symptoms of disease. Thus, in embodiments, inhibition includes, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the relative to the activity or function of the protein in the absence of the activator (e.g. composition described herein). Thus, in embodiments, activation may include, at least in part, partially or totally increasing stimulation, increasing or enabling activation, or activating, sensitizing, or up-regulating signal transduction or enzymatic activity or the amount of a protein decreased in a disease.

The term "recombinant" when used with reference, for example, to a cell, a nucleic acid, a protein, or a vector, indicates that the cell, nucleic acid, protein or vector has been modified by or is the result of laboratory methods. Thus, for example, recombinant proteins include proteins produced by laboratory methods. Recombinant proteins can include amino acid residues not found within the native (non-recombinant) form of the protein or can be include amino acid residues that have been modified, e.g., labeled.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. In some embodiments, antibodies or fragments of antibodies may be derived from different organisms, including humans, mice, rats, hamsters, camels, etc. Antibodies of the invention may include antibodies that have been modified or mutated at one or more amino acid positions to improve or modulate a desired function of the antibody (e.g. glycosylation, expression, antigen recognition, effector functions, antigen binding, specificity, etc.).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. The Fc (i.e. fragment crystallizable region) is the "base" or "tail" of an immunoglobulin and is typically composed of two heavy chains that contribute two or three constant domains depending on the class of the antibody. By binding to specific proteins the Fc region ensures that each antibody generates an appropriate immune response for a given antigen. The Fc region also binds to various cell receptors, such as Fc receptors, and other immune molecules, such as complement proteins.

Antibodies exist, for example, as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

A single-chain variable fragment (scFv) is typically a fusion protein of the variable regions of the heavy (VH) and light chains (VL) of immunoglobulins, connected with a short linker peptide of 10 to about 25 amino acids. The linker may usually rich in glycine for flexibility, as well as serine or threonine for solubility. The linker can either connect the N-terminus of the VH with the C-terminus of the VL, or vice versa.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

Techniques for conjugating therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to to an antibody. A "therapeutic agent" as referred to herein, is a composition useful in treating or preventing a disease such as cancer, neurodegenerative disease, or cardiovascular disease.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

The term "recombinant masking protein" refers to a recombinantly expressed polypeptide capable of binding to, or otherwise exhibiting an affinity for, a particular type of ligand (e.g. polypeptide, polynucleotide, antibody, cellular component, or tissue) or ligand domain as described herein. When non-covalently bound to the ligand (e.g. ligand domain of a recombinant ligand protein as described herein), a recombinant masking protein inhibits or otherwise prevents the activity or binding of the recombinant ligand protein to its cognate receptor or protein. A recombinant masking protein includes one or more protein masking domains having one or more "masking dimerizing domains." The masking dimerizing domains serve as an anchor or structural support for a "ligand-masking binding domain." The masking dimerizing domains are pairs of identical proteins (e.g. 1-1 (dimer) or 2-2 (tetramer)) and, in embodiments, are antibody Fc domains or regions (e.g. full length or fragments of IgG Fc or IgM Fc). Recombinant masking proteins include one or more "cleavable masking linkers" as described herein. A recombinant masking protein further includes one or more ligand-masking binding domains which non-covalently binds to, and thereby exhibit affinity for, a cognate ligand domain. The ligand-masking binding domain exhibits sufficient affinity for its cognate ligand domain to prevent the activity or binding of the ligand domain to a protein or receptor. The ligand-masking binding domain may be a polypeptide, polynucleotide, antibody, glycoprotein, or receptor capable of selectively recognizign and binding to a ligand domain.

A "cellular protein domain" is a protein (e.g. full length or functional or antigenic fragment thereof) having intracellular or extracellular activity. A cellular protein domain may be associated with a protein signal transduction pathway or receptor/ligand binding. A cellular protein domain may be a cellular growth factor domain (e.g. a full length or functional fragment of a protein associated with cellular growth) or a cellular surface protein domain (e.g. a full length or functional fragment of a protein associated with a protein or receptor located on the cell surface). In embodiments, the cellular protein domain is a protein known to be associated with the cause of, or in the progression of, a particular disease state (e.g. cancer, neurodegenerative disease, or cardiovascular disease).

The term "recombinant ligand protein" refers to a recombinantly expressed polypeptide capable of binding to, or otherwise exhibiting an affinity for, a particular type of receptor or protein found in or on a cell, or ligand-masking binding domain as described herein. A recombinant ligand protein is composed of one or more "ligand dimerizing domains" which may serve as an anchor or structural support for a "ligand domain" via attachment through a ligand linker as described herein. The ligand domain may be a polypeptide, polynucleotide, antibody, glycoprotein, or receptor capable of selectively recognizing and binding to a corresponding ligand-masking binding domain of a recombinant masking protein. The ligand dimerizing domains are pairs of identical proteins (e.g. 1-1 (dimer) or 2-2 (tetramer)) and, in embodiments, are antibody Fc domains or regions (e.g. full length or fragments of IgG Fc or IgM Fc). The ligand domain may be a cellular protein binding domain (e.g. a full length or functional fragment of a cellular protein recognized or otherwise bound by a particular cellular protein domain as described herein, including embodiments thereof. In embodiments, the recombinant ligand protein is an antibody. In embodiments, the recombinant ligand protein is a monoclonal antibody (mAb). The mAb may be a therapeutic monoclonal antibody. The mAb may be an mAb that recognizes a cellular protein domain as described herein, including embodiments thereof. In embodiments, the mAb is ipilimumab, engineered recombinant lipocalin2, cetuximab, trastuzumab, efalizumab, Etanercept, Adalimumab, Bevacizumab, Gemtuzumab, Infliximab, Natalizumab, Ofatumumab, Panitumumab, Rituximab, Tocilizumab, Abciximab, Ustekinumab, Pertuzumab, or Alemtuzumab.

A "targeting domain" as used herein, refers to a monovalent composition capable of binding to, or otherwise exhibiting an affinity for, a particular type of tissue or component thereof. The addition of a targeting domain to a recombinant masking protein can direct the recombinant masking protein to particular sites within the body. Targeting domains may include, for example, proteins, antibodies, antibody fragments, peptides, carbohydrates, lipids, oligonucleotides, DNA, RNA, or small molecules having a molecular weight less than 2000 Daltons. In embodiments, a targeting domain is a single-chain variable fragment (scFv) domain as described herein.

As used herein, "treating" or "treatment of" a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently.

As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a cleavable linker as described herein and a protease. In embodiments contacting includes, for example, allowing a recombinant masking protein described herein to interact with a recombinant ligand protein.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The compound of the invention can be administered alone or can be coadministered to the patient. Coadministration is meant to include simultaneous or sequential administration of the compound individually or in combination (more than one compound or agent). Co-administration as used herein also refers to administration of ADCs as described herein. Thus, in embodiments, the preparations can also be combined, when desired, with other active substances (e.g. to reduce metabolic degradation). The compositions of the present invention can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.*

49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

A "effective amount" is an amount sufficient for an active compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations.

Pharmaceutical compositions provided by the present invention include compositions wherein the active ingredient (e.g. compositions described herein, including embodiments or examples) is contained in a therapeutically effective amount, i.e., in an amount effective to achieve its intended purpose. The actual amount effective for a particular application will depend, inter alia, on the condition being treated. For any recombinant masking protein and/or recombinant ligand protein described herein, the therapeutically effective amount can be initially determined from cell culture assays. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer, neurodegeneration, or cardiovascular disease and severity of such symptoms), kind of concurrent treatment, complications from the disease being treated or other health-related problems. Other therapeutic regimens or agents can be used in conjunction with the methods and compounds of the invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner.

Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Anti-cancer agent" is used in accordance with its plain ordinary meaning and refers to a composition (e.g. compound, drug, antagonist, inhibitor, modulator) having anti-neoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

The compounds described herein can be used in combination with one another, with other active agents known to be useful in treating a cancer such as anti-cancer agents.

Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclixmab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate;

rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or r1L.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin Al (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like. In embodiments, the compositions herein may be used in combination with adjunctive agents that may not be effective alone, but may contribute to the efficacy of the active agent in treating cancer.

The compositions described herein can be used in combination with one another, with other active agents known to be useful in treating a neurodegenerative disease. Exemplary active agents include but are not limited to: levodopa, dopamine agonists (e.g. bromocriptine, pergolide, pramipexole, ropinirole, piribedil, cabergoline, apomorphine, lisuride), MAO-B inhibitors (e.g. selegiline or rasagiline), amantadine, anticholinergics, antipsychotics (e.g. clozapine), cholinesterase inhibitors, modafinil, or non-steroidal anti-inflammatory drugs. In embodiments, the compositions herein may be used in combination with adjunctive agents that may not be effective alone, but may contribute to the efficacy of the active agent in treating neurodegenerative disease.

The compounds described herein can be used in combination with one another, with other active agents known to be useful in treating a cardiovascular disease such as angiotensin-converting enzyme (ACE) inhibitors, Aldosterone inhibitors, Angiotensin II receptor blockers (ARB), beta blockers, calcium-channel blockers, vasodilators, statins, antiplatelet agents, anticoagulants, or diuretics. In embodiments, the compositions herein may be used in combination with adjunctive agents that may not be effective alone, but may contribute to the efficacy of the active agent in treating cardiovascular disease.

In embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In embodiments, co-administration can be accomplished by co-formulation, i.e., preparing a single pharmaceutical composition including both active agents. In embodiments, the active agents can be formulated separately. In embodiments, the active and/or adjunctive agents may be linked or conjugated to one another.

The term "associated" or "associated with" in the context of a substance or substance activity or function associated with a disease (e.g. a protein associated disease, or symptom associated with a cancer, neurodegenerative disease, or cardiovascular disease) means that the disease (e.g. cancer, neurodegenerative disease, or cardiovascular disease) is caused or characterized by (in whole or in part) the substance or substance activity or function, or a symptom of the disease is caused or characterized by (in whole or in part) the substance or substance activity or function. As used herein, what is described as being associated with a disease, if a causative agent, could be a target for treatment of the disease. For example, a disease associated with aberrant CTLA-4 expression or function, may be treated with an agent (e.g. composition as described herein) effective for decreasing the level of activity of CTLA-4.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active or prodrug form of a composition as provided herein with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "cancer" refers to all types of cancer, neoplasm, benign or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulinoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The P388 leukemia model is widely accepted as being predictive of in vivo anti-leukemic activity. It is believed that a compound that tests positive in the P388 assay will generally exhibit some level of anti-leukemic activity in vivo regardless of the type of leukemia being treated. Accordingly, the present application includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

As used herein, the terms "metastasis," "metastatic," and "metastatic cancer" can be used interchangeably and refer to the spread of a proliferative disease or disorder, e.g., cancer, from one organ to another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans).

As used herein, an "autoimmune disease" refers to a disease or disorder that arises from altered immune reactions by the immune system of a subject, e.g., against substances tissues and/or cells normally present in the body of the subject. Autoimmune diseases include, but are not limited to, arthritis, rheumatoid arthritis, psoriatic arthritis, juvenile idiopathic arthritis, scleroderma, systemic scleroderma, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, psoriasis, ichthyosis, Graves ophthalmopathy, inflammatory bowel disease, Addison's disease, vitiligo, asthma, and allergic asthma.

As used herein, the term "neurodegenerative disease" refers to a disease or condition in which the function of a subject's nervous system becomes impaired. Examples of neurodegenerative diseases that may be treated with a compound or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes *dorsalis*, drug-induced Parkinsonism, progressive supranuclear palsy, corticobasal degeneration, multiple system atrophy, Idiopathic Parkinson's disease, Autosomal dominant Parkinson disease, Parkinson disease, familial, type 1 (PARK1), Parkinson disease 3, autosomal dominant Lewy body (PARK3), Parkinson disease 4, autosomal dominant Lewy body (PARK4), Parkinson disease 5 (PARK5), Parkinson disease 6, autosomal recessive early-onset (PARK6), Parkinson disease 2, autosomal recessive juvenile (PARK2), Parkinson disease 7, autosomal recessive early-onset (PARK7), Parkinson disease 8 (PARK8), Parkinson disease 9 (PARK9), Parkinson disease 10 (PARK10), Parkinson disease 11 (PARK11), Parkinson disease 12 (PARK12), or Parkinson disease 13 (PARK13).

As used herein, "cardiovascular diseases" refer to diseases associated with the heart, blood vessels or both. Cardiovascular diseases include, but are not limited to, coronary heart disease, cardiomyopathy, hypertensive heart disease, heart failure, cardiac dysrhythmias, inflammatory heart disease, peripheral arterial disease, cerebrovascular disease and inflammatory heart disease.

A "cleavable masking linker" as used herein refers to a portion of a polyvalent linker covalently bonded to a ligand-masking binding domain and covalently bonded to a masking dimerizing domain. In embodiments the cleavable masking linker is recombinantly expressed. In embodiments, the cleavable masking linker is a linker formed by reacting a functional (reactive) group attached to the linker with a masking dimerizing domain using, for example, conjugate chemistry. In embodiments, the cleavable masking linker may be a linker formed by reacting a functional (reactive) group attached to the linker with a ligand-masking binding domain using, for example, conjugate chemistry. A cleavable masking linker may have the formula:

$$\text{LMBD-CML-MDD} \tag{I}$$

Figure 2:
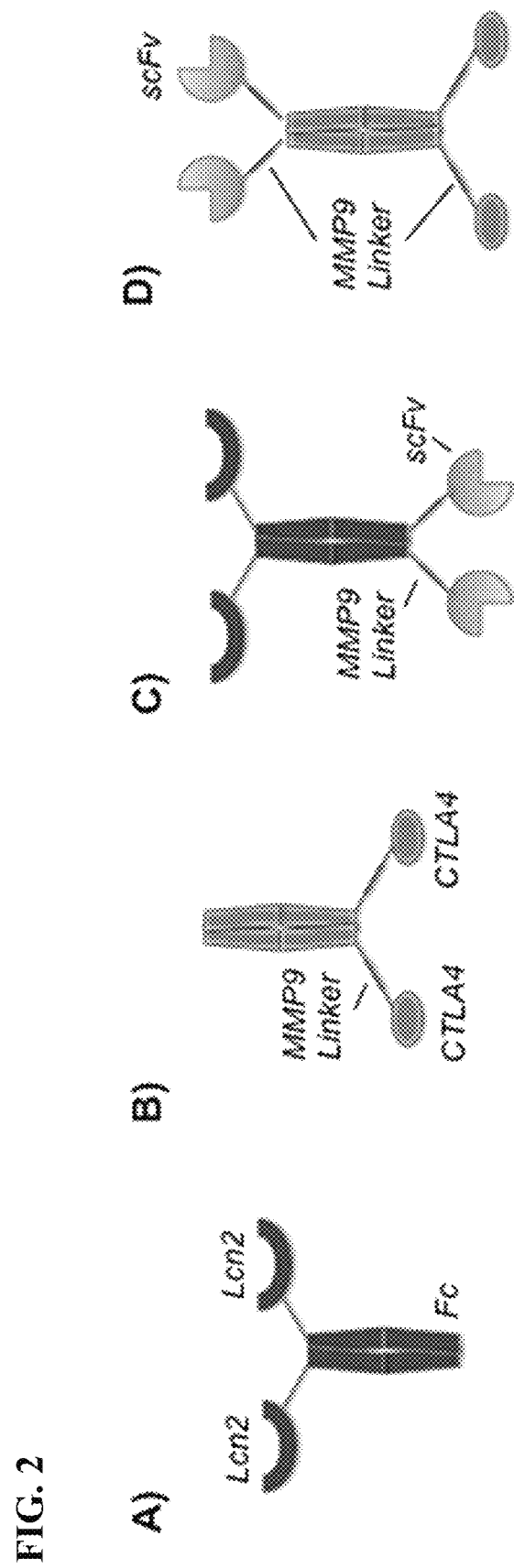
FIG. 2: Variant m-Lcn2 and mask designs to facilitate tumor targeting: A) To create a bivalent analog, m-Lcn2 is fused to the human $IgG_1$ Fc domain; B) To create a bivalent mask, CTLA-4 is fused to the same Fc domain, but the linker contains a MMP9 site; C) To enhance tumor targeting, an HA scFv may be fused to the C-terminus of the m-Lcn2-Fc construct (MMP9 cleavage site may added to enhance engagement TILs at tumor sites) and a non-cleavable linker may also be generated; D) The same targeting principle may be applied to the CTLA4-Fc mask (please refer to FIG. 1 panel B).

In Formula (I), LMBD is a ligand-masking binding domain, CML is a cleavable masking linker, and MDD is a dimeric masking domain. As described herein, each recombinant masking protein may include one or more cleavable masking linkers. A cleavable masking linker includes a cleavage site as described herein. FIGS. 1 and 2 set forth exemplary recombinant masking proteins having exemplary ligand-masking domains and cleavable masking linkers.

A "ligand linker" as used herein refers to a portion of a polyvalent linker covalently bonded to a ligand domain and covalently bonded to a ligand dimerizing domain. In embodiments the ligand linker is recombinantly expressed. In embodiments, the ligand linker is a linker formed by reacting a functional (reactive) group attached to the linker with a ligand dimerizing domain using, for example, conjugate chemistry. In embodiments, the ligand linker may be a linker formed by reacting a functional (reactive) group attached to the linker with the ligand domain using, for example, conjugate chemistry. A ligand linker may have the formula:

LDD-LL-LD          (II).

In Formula (II), LDD is a ligand dimerizing domain, LL is a ligand linker, and LD is a ligand domain. As described herein, each recombinant ligand protein may include one or more ligand linkers. In embodiments, the ligand linker includes a cleavage site as described herein. FIGS. 1 and 2 set forth exemplary recombinant masking proteins having exemplary ligand domains and linker linkers.

A "targeting linker" as used herein refers to a portion of a polyvalent linker covalently bonded to a targeting domain and covalently bonded to a masking dimerizing domain. In embodiments the targeting linker is recombinantly expressed. In embodiments, the targeting linker is a linker formed by reacting a functional (reactive) group attached to the linker with a masking dimerizing domain using, for example, conjugate chemistry. In embodiments, the targeting linker may be a linker formed by reacting a functional (reactive) group attached to the linker with a targeting domain using, for example, conjugate chemistry. A targeting linker may have the formula:

TD-TL-MDD          (III).

In Formula (III), TD is a targeting domain, TL is a targeting linker, and MDD is a masking dimerization domain. As described herein, each recombinant masking protein may include one or more targeting linkers and one or more targeting domains. In embodiments, the targeting linker includes a cleavage site as described herein. FIGS. 1 and 2 set forth exemplary recombinant masking proteins having exemplary targeting domains and targeting linkers.

A "cleavage site" as used herein, refers to a recognizable site for cleavage of a portion of a linker (e.g. polyvalent linker as described hereinabove) found in a recombinant masking protein or recombinant ligand protein described herein. Thus, a cleavage site may be found in the sequence of a cleavable masking linker, a ligand linker, or a targeting linker as described herein, including embodiments thereof. In embodiments, the cleavage site is an amino acid sequence that is recognized and cleaved by a cleavage agent (e.g. a peptidyl sequence). Exemplary cleavage agents include proteins, enzymes, DNAzymes, RNAzymes, metals, acids, and bases. Exemplary cleavage sites are defined herein.

The terms "conjugate" and "conjugate chemistry" refer to reactions with known reactive groups which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups used for conjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(i) metal silicon oxide bonding; and (l) metal bonding to reactive phosphorus groups (e.g. phosphines) to form, for example, phopshate diester bonds.

The reactive functional groups can be chosen such that they do not participate in, or interfere with, the chemical stability of the compositions described herein. Alternatively, a reactive functional group can be protected from participating in the crosslinking reaction by the presence of a protecting group.

Described herein are 'antibody prodrugs' that use tumor-associated properties to activate a modified mAb at a disease site. Discovered herein, a non-covalent recombinant masking protein (e.g. mAb mask), when integrated with clinically validated mAbs (i.e. recombinant ligand proteins described herein), reduces the validated mAb's affinity or occludes its antigen binding site in normal tissue but becomes activated at the tumor by tumor-specific proteases.

The term "CTLA-4" or "CTLA-4 protein" as provided herein includes any of the recombinant or naturally-occurring forms of the cytotoxic T-lymphocyte-associated protein 4 (CTLA-4) or variants or homologs thereof that maintain CTLA-4 protein activity (e.g. within at least 50%, 80%, 90%, 95%, 96%, 97%, 98%, 99% or 100% activity compared to CTLA-4). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CTLA-4 polypeptide. In embodiments, CTLA-4 is the protein as identified by the NCBI sequence reference GI:83700231, homolog or functional fragment thereof.

The term "LCN2" as provided herein includes any of the recombinant or naturally-occurring forms of the lipocalin 2 (LCN2) protein or variants or homologs thereof that maintain LCN2 protein activity (e.g. within at least 50%, 80%, 90%, 95%, 96%, 97%, 98%, 99% or 100% activity compared to LCN2). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring LCN2 polypeptide. In embodiments, the LCN2 protein is the protein as identified by the NCBI sequence reference GI:38455402, homolog or functional fragment thereof.

The modified lipocalin2 (mLcn2) used as a CTLA-4 antagonist (CTLA-4 binding protein) herein binds to murine, primate and human CTLA-4. In embodiments, mLCN2 has the sequence of SEQ ID NO:15. In some aspects, the mLcn2 has at least 90%, 95%, 96%, 97%, 98%, 99% or 100% amino acid sequence identity across the whole sequence or a portion of the sequence (e.g. a 50, 100, 150 or 200 continuous amino acid portion) compared to SEQ ID NO:15. In embodiments, mLcn2 is the protein as identified by SEQ ID NO:15 or homolog or functional fragment thereof.

The term "MMP 2" or "MMP 2 protease" as provided herein includes any of the recombinant or naturally-occurring forms of the matrix metalloproteinase 2 (MMP 2) or variants or homologs thereof that maintain MMP 2 activity (e.g. within at least 50%, 80%, 90%, 95%, 96%, 97%, 98%, 99% or 100% activity compared to MMP 2). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring MMP 2 polypeptide. In embodiments, MMP 2 is the protein as identified by the NCBI sequence reference GI:189217853, homolog or functional fragment thereof.

The term "MMP 9" or "MMP 9 protease" as provided herein includes any of the recombinant or naturally-occurring forms of the matrix metalloproteinase 9 (MMP 9) or variants or homologs thereof that maintain MMP 9 activity (e.g. within at least 50%, 80%, 90%, 95%, 96%, 97%, 98%, 99% or 100% activity compared to MMP 9). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring MMP 9 polypeptide. In embodiments, MMP 9 is the protein as identified by the NCBI sequence reference GI:74272287, homolog or functional fragment thereof.

The term "MMP 13" or "MMP 13 protease" as provided herein includes any of the recombinant or naturally-occurring forms of the matrix metalloproteinase 13 (MMP 13) or variants or homologs thereof that maintain MMP 13 activity (e.g. within at least 50%, 80%, 90%, 95%, 96%, 97%, 98%, 99% or 100% activity compared to MMP 13). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring MMP 13 polypeptide. In embodiments, MMP 13 is the protein as identified by the NCBI sequence reference GI:4505209, homolog or functional fragment thereof.

The term "ADAM 9" or "ADAM 9 protease" as provided herein includes any of the recombinant or naturally-occurring forms of the disintegrin and metalloprotease domain-containing (ADAM) protein 9 or variants or homologs thereof that maintain ADAM 9 activity (e.g. within at least 50%, 80%, 90%, 95%, 96%, 97%, 98%, 99% or 100% activity compared to ADAM 9). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ADAM 9 polypeptide. In embodiments, ADAM 9 is the protein as identified by the NCBI sequence reference GI:4501915, homolog or functional fragment thereof.

The term "ADAM 10" or "ADAM 10 protease" as provided herein includes any of the recombinant or naturally-occurring forms of the disintegrin and metalloprotease domain-containing (ADAM) protein 10 or variants or homologs thereof that maintain ADAM 10 activity (e.g. within at least 50%, 80%, 90%, 95%, 96%, 97%, 98%, 99% or 100% activity compared to ADAM 10). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ADAM 10 polypeptide. In embodiments, ADAM 10 is the protein as identified by the NCBI sequence reference GI:4557251, homolog or functional fragment thereof.

The term "ADAM 17" or "ADAM 17 protease" as provided herein includes any of the recombinant or naturally-occurring forms of the disintegrin and metalloprotease domain-containing (ADAM) protein 17 or variants or homologs thereof that maintain ADAM 17 activity (e.g. within at least 50%, 80%, 90%, 95%, 96%, 97%, 98%, 99% or 100% activity compared to ADAM 17). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ADAM 17 polypeptide. In embodiments, ADAM 17 is the protein as identified by the NCBI sequence reference GI:73747889, homolog or functional fragment thereof.

The term "PSA" or "PSA protease" as provided herein includes any of the recombinant or naturally-occurring forms of the prostate-specific antigen (PSA), also known as gamma seminoprotein or kallikrein-3, or variants or homologs thereof that maintain PSA activity (e.g. within at least 50%, 80%, 90%, 95%, 96%, 97%, 98%, 99% or 100% activity compared to PSA). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PSA polypeptide. In embodiments, PSA is the protein as identified by the NCBI sequence reference GI:71834853, homolog or functional fragment thereof.

I. COMPOSITIONS

Provided herein are recombinant masking protein compositions. The recombinant masking protein includes two identical masking protein domains. Each masking protein domain includes (1) a masking dimerizing domain; (2) a ligand-masking binding domain; and (3) a cleavable masking linker connecting the ligand-masking binding domain to the masking dimerizing domain, and where the masking protein domains are bound together. The masking protein domains may be bound together through the respective masking dimerizing domains.

The masking dimerizing domain may be an Fc protein domain. The Fc protein domain may be an IgG or IgM Fc protein. In embodiments, the Fc protein is an IgG Fc protein. The IgG Fc protein may be an $IgG_1$ Fc protein. In embodiments, the $IgG_1$ Fc protein has a molecular weight of about 5 kDa, 10 kDa, 15 kDa, 20 kDa, 25 kDa, 30 kDa, 35 kDa, 40 kDa, 45 kDa, 50 kDa, 55 kDa, 60 kDa, 70 kDa, 75 kDa, 80 kDa, 85 kDa, 90 kDa, 95 kDa, 100 kDa, 110 kDa, 120 kDa, 130 kDa, 140 kDa, 150 kDa, 160 kDa, or 170 kDa. The $IgG_1$ Fc protein may have a molecular weight of about 30 kDa to about 70 kDa. The $IgG_1$ Fc protein may have a molecular weight of about 40 kDa to about 60 kDa. In embodiments, the Fc protein is an IgM Fc protein. The masking dimerizing domain may be a multivalent protein domain (e.g. preferably dimeric, but also trimeric and tetrameric protein domains). The masking dimerizing domain may be a nanoparticle.

In embodiments, the masking domain is about 50, 75, 100, 125, 150, 175, 200, 225, 250, 275, 300, 325, 350, 375, 400, 425, 450, 475, or 500 amino acids in length. In embodiments, the masking domain is about 50 to about 450 amino acids in length. In embodiments, the masking domain is about 50 to about 450 amino acids in length. In embodiments, the masking domain is about 50 to about 400 amino acids in length. In embodiments, the masking domain is about 50 to about 350 amino acids in length. In embodiments, the masking domain is about 50 to about 300 amino acids in length. In embodiments, the masking domain is about 50 to about 250 amino acids in length. In embodiments, the masking domain is about 50 to about 200 amino acids in length. In embodiments, the masking domain is about 50 to about 150 amino acids in length. In embodiments, the masking domain is about 50 to about 100 amino acids in length. In embodiments, the masking domain is about 100 to about 200 amino acids in length. In embodiments, the masking domain is about 125 to about 200 amino acids in length. In embodiments, the masking domain is about 150 to about 200 amino acids in length. In embodiments, the masking domain is about 175 to about 200 amino acids in length.

The ligand-masking binding domain may be a small molecule or a protein (e.g. a cellular protein domain). The cellular protein domain may be a cellular growth factor domain, a cellular surface protein domain or functional fragment thereof. Thus, in embodiments, the cellular protein domain may be a cellular growth factor domain. The cellular growth factor domain may be a cytokine domain. The cellular growth factor domain may be a hormone domain. In embodiments, the cellular growth factor domain is a PDGF domain (e.g. a full length or functional fragment of platelet-derived growth factor), an EGF domain (e.g. a full length or functional fragment of epidermal growth factor), a TGF domain (e.g. a full length or functional fragment of transforming growth factor alpha or beta), a VEGF domain (e.g. a full length or functional fragment of vascular endothelial growth factor), a FGF domain (e.g. a full length or functional fragment of fibroblast growth factor), or a TNF domain (e.g. a full length or functional fragment of tumor necrosis factor). The cellular growth factor domain may be a TNF domain.

In embodiments, the cellular protein domain is a cellular surface protein domain. The cellular surface protein domain may be a receptor tyrosine kinase domain. In embodiments, the receptor tyrosine kinase domain is a class I, class II, class III, class IV, class V, class VI, class VII, class VII, class IX, class X, class XI, class XII, class XIII, class XIV, class XV, class XVI, or class XVII receptor tyrosine kinase domain (e.g. a full length or functional fragment thereof). In embodiments, the receptor tyrosine kinase domain is an ErbB receptor domain (e.g. a full length or functional fragment of ErbB). The ErbB domain may be an EGFR domain (e.g. a full length or functional fragment of ErbB-1/EGFR), a Her2 domain (e.g. a full length or functional fragment of ErbB-2/Her2), a Her3 domain (e.g. a full length or functional fragment of ErbB-3/Her3), or a Her4 domain (e.g. a full length or functional fragment of ErbB-4/Her4). In embodiments, the Erbb domain is an EGFR domain or a Her2 domain. In embodiments, the receptor tyrosine kinase domain is a PDGFR domain (e.g. a full length or functional fragment of platelet derived growth factor receptor). In embodiments, the receptor tyrosine kinase domain is a FGFR domain (e.g. a full length or functional fragment of fibroblast growth factor receptor). In embodiments, the receptor tyrosine kinase domain is a VEGFR domain (e.g. a full length or functional fragment of vascular endothelial growth factor receptor). In embodiments, the receptor tyrosine kinase domain is a HGFR domain (e.g. a full length or functional fragment of hepatocyte growth factor receptor). In embodiments, the cellular surface protein domain is an ErbB receptor domain or a T-cell receptor domain.

The cellular surface protein domain may be a T-cell receptor domain. The T-cell receptor domain may be a CTLA-4 domain or a functional fragment thereof. The T-cell receptor domain may be a CTLA-4 domain. Thus, in embodiments, the ligand-masking binding domain is CTLA-4 or a variant thereof. In embodiments, the CTLA-4 domain has the sequence set forth in Table 1.

TABLE 1

SEQ ID NOs of CTLA-4 variants

| SEQ ID NO: | Description |
|---|---|
| SEQ ID NO: 1 | WT CTLA-4 |
| SEQ ID NO: 2 | E31A and R33A CTLA-4 |
| SEQ ID NO: 3 | E31S CTLA-4 |
| SEQ ID NO: 4 | E31K CTLA-4 |
| SEQ ID NO: 5 | E31R CTLA-4 |
| SEQ ID NO: 6 | E31S, R33E, T51H CTLA-4 |
| SEQ ID NO: 7 | T51H CTLA-4 |
| SEQ ID NO: 8 | K95A CTLA-4 |
| SEQ ID NO: 9 | E97A CTLA-4 |
| SEQ ID NO: 10 | K95A and E97A CTLA-4 |

In embodiments, the ligand-masking binding domain is an antibody-masking binding domain (i.e. a masking binding domain that binds to an antibody). The antibody-masking binding domain may be a monoclonal antibody-masking domain (i.e. a masking binding domain that binds to a monoclonal antibody). Thus, in embodiments, the ligand-masking domain is a lipocalin 2 masking domain (i.e. a masking binding domain that binds to mLCN2). The ligand-masking domain may be an ipilimumab-masking domain (i.e. a masking binding domain that binds to ipilimumab). The ligand-masking domain may be an efalizumab-masking domain (i.e. a masking biding domain that binds to efalizumab). The ligand-masking domain may be a trastuzumab-masking domain (i.e. a masking binding domain that binds to trastuzumab). The ligand-masking domain may be a cetuximab-masking domain (i.e. a masking binding domain that binds to cetuximab). The ligand-masking domain may be an infliximab-masking domain (i.e. a masking binding domain that binds to infliximab). The ligand-masking domain may be an etanercept-masking domain (i.e. a masking binding domain that binds to etanercept). The ligand-masking domain may be an adalimumab-masking domain (i.e. a masking binding domain that binds to adalimumab). The ligand-masking domain may be an abciximab-masking domain (i.e. a masking binding domain that binds to abciximab). The ligand-masking domain may be a rituximab-masking domain (i.e. a masking binding domain that binds to rituximab). The ligand-masking domain may be a bevacizumab-masking domain (i.e. a masking binding domain that binds to bevacizumab). The ligand-masking domain may be a gemtuzumab-masking domain (i.e. a masking binding domain that binds to gemtuzumab). The ligand-masking domain may be a natalizumab-masking domain (i.e. a masking binding domain that binds to natalizumab). The ligand-masking domain may be a panitumumab-masking domain (i.e. a masking binding domain that binds to panitumumab). The ligand-masking domain may be an ofatumumab-masking domain (i.e. a masking binding domain that binds to ofatumumab). The ligand-masking domain may be a tocilizumab-masking domain (i.e. a masking binding domain that binds to tocilizumab). The ligand-masking domain may be an ustekinumab-masking domain (i.e. a masking binding domain that binds to ustekinumab). The ligand-masking domain may be a pertuzumab-masking domain (i.e. a masking binding domain that binds to pertuzumab). The ligand-masking domain may be an alemtuzumab-masking domain (i.e. a masking binding domain that binds to alemtuzumab).

The cleavable masking linker may optionally include a protease cleavage site. In embodiments, the protease cleavage site is recognized by a protease specific to a cancer or tumor site (i.e. the protease is only expressed or is overexpressed in the cancer or tumor site). In embodiments, the protease cleavage site is a matrix metalloprotease cleavage site (e.g. a protease cleavage site recognized and cleaved by a matrix metalloprotease as described herein), a disintegrin and metalloproteinase domain-containing (ADAM) metalloprotease cleavage site (e.g. a protease cleavage site recognized and cleaved by an ADAM) or a prostate specific antigen (PSA) protease cleavage site (e.g. a protease cleavage site recognized and cleaved by PSA). In embodiments, the protease cleavage site is a matrix metalloprotease cleavage site. In embodiments, the protease cleavage site is a site recognized by metalloproteinase 2 (MMP2) or metalloproteinase 9 (MMP9). In embodiments, the protease cleavage site is a site recognized by metalloproteinase 9 (MMP9). In embodiments, the protease cleavage site is a peptidyl sequence.

In embodiments, the cleavable masking linker includes a enzymatic cleavage site (e.g. a site cleaved via an enzyme-catalyzed reaction), a metal cleavage site (e.g. a site cleaved via a metal-catalyzed reaction), an acid cleave site (e.g. a site cleaved via an acid-catalyzed reaction), a base cleave site (e.g. a site cleaved via a base-catalyzed reaction), or a redox cleavage site (e.g. a site cleaved via a redox-catalyzed reaction).

The cleavage site on the cleavable masking linker may be cleaved at its contact point with the ligand-masking binding domain. Alternatively, the cleavage site on the cleavable masking linker may be cleaved at its contact point with the masking dimerization domain. In embodiments, the cleavage site on the cleavable masking linker may be may be cleaved at a point between its contact points with the masking dimerization domain and the ligand-masking binding domain.

In embodiments, the recombinant masking protein is bound to a recombinant ligand protein. The recombinant ligand protein includes two identical ligand protein domains. Each ligand protein domain includes: (1) a ligand dimerizing domain; (2) a ligand domain; bound to one of the ligand-masking binding domains of the recombinant masking protein; and (3) a ligand linker connecting the ligand domain to the ligand dimerizing domain, and where the ligand protein domains are bound together. The ligand protein domains may be bound together through the respective ligand dimerizing domains.

The ligand dimerizing domain may be an Fc protein domain as described herein, including embodiments thereof. The ligand dimerizing domain may be an Fc protein domain that is an $IgG_1$ Fc protein as described herein, including embodiments thereof.

In embodiments, the recombinant ligand protein is a monoclonal antibody (mAb). In embodiments, the recombinant ligand protein is ipilimumab, lipocalin2, cetuximab, trastuzumab, efalizumab, etanercept, adalimumab, bevacizumab, gemtuzumab, infliximab, natalizumab, ofatumumab, panitumumab, rituximab, tocilizumab, abciximab, ustekinumab, pertuzumab, or alemtuzumab.

The ligand domain may be a cellular protein binding domain. The cellular protein binding domain may be a cellular growth factor binding domain, a cellular surface protein binding domain or functional fragment thereof. Thus, in embodiments, the cellular protein binding domain may be a cellular growth factor binding domain. The cellular growth factor binding domain may be a cytokine binding domain. The cellular growth factor binding domain may be a hormone binding domain. In embodiments, the cellular growth factor binding domain is a PDGF binding domain (e.g. a full length or functional fragment of platelet-derived growth factor), an EGF binding domain (e.g. a full length or functional fragment of epidermal growth factor), a TGF binding domain (e.g. a full length or functional fragment of transforming growth factor alpha or beta), a VEGF binding domain (e.g. a full length or functional fragment of vascular endothelial growth factor), a FGF binding domain (e.g. a full length or functional fragment of fibroblast growth factor), or a TNF receptor domain (e.g. a full length or functional fragment of tumor necrosis factor). The cellular growth factor domain may be a TNF receptor domain.

In embodiments, the cellular protein binding domain is a cellular surface protein binding domain. The cellular surface protein binding domain may be a receptor tyrosine kinase binding domain. In embodiments, the receptor tyrosine kinase binding domain is a class I, class II, class III, class IV, class V, class VI, class VII, class VII, class IX, class X, class XI, class XII, class XIII, class XIV, class XV, class XVI, or class XVII receptor tyrosine kinase binding domain (e.g. a full length or functional fragment thereof). In embodiments, the receptor tyrosine kinase binding domain is an ErbB receptor binding domain (e.g. a full length or functional fragment of ErbB). The ErbB binding domain may be an EGFR binding domain (e.g. a full length or functional fragment of ErbB-1/EGFR), a Her2 binding domain (e.g. a full length or functional fragment of ErbB-2/Her2), a Her3 binding domain (e.g. a full length or functional fragment of ErbB-3/Her3), or a Her4 binding domain (e.g. a full length or functional fragment of ErbB-4/Her4). In embodiments, the Erbb binding domain is an EGFR binding domain or a Her2 binding domain. In embodiments, the receptor tyrosine kinase binding domain is a PDGFR binding domain (e.g. a full length or functional fragment of platelet derived growth factor receptor). In embodiments, the receptor tyrosine kinase binding domain is a FGFR binding domain (e.g. a full length or functional fragment of fibroblast growth factor receptor). In embodiments, the receptor tyrosine kinase binding domain is a VEGFR binding domain (e.g. a full length or functional fragment of vascular endothelial growth factor receptor). In embodiments, the receptor tyrosine kinase binding domain is a HGFR binding domain (e.g. a full length or functional fragment of hepatocyte growth factor receptor). In embodiments, the cellular surface protein binding domain is an ErbB receptor binding domain or a T-cell receptor binding domain.

The cellular surface protein domain may be a T-cell receptor binding domain. The T-cell receptor domain may be a CTLA-4 binding domain or a functional fragment thereof. The T-cell receptor domain may be a CTLA-4 binding domain. The CTLA-4 binding domain may be a LCN2 binding domain.

In embodiments, the ligand domain includes a CDR domain. The ligand domain may be an antibody domain.

The ligand linker may optionally include a cleavage site. The ligand linker cleavage site may include a protease cleavage site, a enzymatic cleavage site, a metal cleavage site, an acid cleave site, a base cleave site, or a redox cleavage site as described herein, including embodiments thereof.

In embodiments, the masking dimerizing domains connect to a targeting domain through a targeting linker. The targeting linker may be connected to the C-terminus of the masking dimerizing domain. Thus, in embodiments, if the targeting linker is connected to the C-terminus of the masking dimerizing domain, the cleavable masking linker may be connected to the N-terminus of the masking dimerizing domain. In embodiments, the targeting linker may be connected to the N-terminus of the masking dimerizing domain. In such embodiments, the cleavable masking linker may be connected to the C-terminus of the masking dimerizing domain. The targeting linker may be a cleavable targeting linker. In embodiments, the cleavable targeting linker includes a protease cleavage site. The protease cleavage site is as described herein, including embodiments thereof. Thus, in embodiments, the protease cleavage site is a matrix metalloprotease cleavage site, a disintegrin and metalloproteinase domain-containing (ADAM) metalloprotease cleavage site or a prostate specific antigen (PSA) protease cleavage site. In embodiments, the protease cleavage site is different on each masking dimerizing domain. In a preferred embodiment, the protease cleavage site on each targeting linker is cleaved by the same protease. In embodiments, the protease cleavage site on the targeting linker is cleaved by the same protease as the protease cleavage site on the cleavable masking linker.

In embodiments, the cleavable targeting linker includes an enzymatic cleavage site, a metal cleavage site, an acid cleave site, a base cleave site, or a redox cleavage site as described herein, including embodiments thereof.

The cleavage site on the cleavable targeting linker may be cleaved at its contact point with the targeting domain. Alternatively, the cleavage site on the cleavable targeting linker may be cleaved at its contact point with the masking dimerization domain. In embodiments, the cleavage site on the cleavable masking linker may be may be cleaved at a point between its contact points with the masking dimerization domain and the targeting domain.

The cleavable linkers described herein (e.g. cleavable masking linker, cleavable ligand linker and cleavable targeting linker) may be orthogonal (i.e. one or more sites may be cleaved independently of the other(s) thereby leaving the uncleaved site(s) intact). Thus, in embodiments, the cleavable linkers described herein may be orthogonally cleaved through the same type of catalysis (e.g. protealysis) by using different cleavage sites or different catalysts (e.g. proteases). Alternatively, the cleavable linkers described herein may be orthogonally cleaved through different types of catalysis.

In embodiments, the targeting domain is a domain that localizes the domain, and its attached recombinant masking protein to a specific cell, tissue, organ, or location within an organism. In embodiments, the targeting domain localizes a recombinant masking protein to a cancer (e.g. a cancer cell or tumor). The recombinant masking protein may be bound to a recombinant ligand protein as described herein. The targeting domain may be a single-chain variable fragment (scFv) domain. In embodiments, the scFv domain is a hemagglutinin (HA) scFv domain.

In embodiments, the ligand dimerizing domains connect to a targeting domain through a targeting linker. The targeting linker may be connected to the C-terminus of the ligand dimerizing domain. Thus, in embodiments, if the targeting linker is connected to the C-terminus of the ligand dimerizing domain, the ligand linker may be connected to the N-terminus of the ligand dimerizing domain. In embodiments, the targeting linker may be connected to the N-terminus of the ligand dimerizing domain. In such embodiments, the ligand linker may be connected to the C-terminus of the ligand dimerizing domain. The targeting linker may be a cleavable targeting linker. The cleavable targeting linker is as described herein, including embodiments thereof. In embodiments, the protease cleavage site on the targeting linker connecting the targeting domain to the ligand dimerization domain is cleaved by the same protease which cleaves the protease cleavage site on the cleavable masking linker or by the same protease which cleaves the protease cleavage site on the cleavable targeting linker connecting a targeting domain to the cleavable masking linker. The targeting domain connected to the ligand dimerization is a targeting domain as described herein, including embodiments thereof. Thus, in embodiments, the targeting domain connected to the ligand dimerization domain may be a scFv domain. The scFv domain may be a hemaglutinin scFv domain.

II. PHARMACEUTICAL COMPOSITIONS

Provided herein are pharmaceutical compositions. In one aspect, the pharmaceutical compositions include a recombinant masking protein and a recombinant ligand protein as described herein. In another aspect, the pharmaceutical compositions include a recombinant masking protein.

The pharmaceutical composition may be prepared and administered in a wide variety of dosage formulations and may be administered orally, rectally, or by injection (e.g. intravenously, intramuscularly, intracutaneously, subcutaneously, intraduodenally, or intraperitoneally).

Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the recombinant protein compositions described herein may be mixed with the carrier having the necessary binding properties in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include a formulation of the recombinant proteins described herein with or without other carriers, and surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the compositions described herein are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the compositions provided herein, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the compositions described herein. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted according to the particular application and the potency of the therapeutic agent used. The composition can, if desired, also contain other compatible therapeutic agents.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

The pharmaceutical composition may include compositions wherein the therapeutic agent is contained in a therapeutically effective amount, i.e., in an amount effective to achieve its intended purpose. The actual amount effective for a particular application will depend, inter alia, on the condition being treated. For example, when administered in methods to treat cancer, such compositions will contain amounts of therapeutic agent effective to achieve the desired result.

The dosage and frequency (single or multiple doses) of the pharmaceutical composition administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of therapeutic agent by considering factors such as potency, bioavailability, patient body weight, presence and severity of adverse side effects, preferred mode of administration, and the toxicity profile of the selected agent.

The ratio between toxicity and therapeutic effect for a particular compound is its therapeutic index and can be expressed as the ratio between LD50 (the amount of compound lethal in 50% of the population) and ED50 (the amount of compound effective in 50% of the population). Therapeutic agents that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the ED50 with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the therapeutic agent is used.

When parenteral application is needed or desired, particularly suitable admixtures for the recombinant proteins described herein included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. Pharmaceutical admixtures suitable for use in the pharmaceutical compositions presented herein may include those described, for example, in Pharmaceutical Sciences (17th Ed., Mack Pub. Co., Easton, Pa.) and WO 96/05309, the teachings of both of which are hereby incorporated by reference.

Thus, in one aspect is a pharmaceutical composition that includes a pharmaceutically acceptable excipient, a recombinant masking protein and a recombinant ligand protein. The recombinant masking protein includes two identical masking protein domains. Each masking protein domain includes: (1) a masking dimerizing domain as described herein, including embodiments thereof; (2) a ligand-masking binding domain as described herein, including embodiments thereof; and (3) a cleavable masking linker as described herein, including embodiments thereof, that connects the ligand-masking binding domain to the masking dimerizing domain. The masking protein domains are bound together. The recombinant ligand protein includes two identical ligand protein domains as described herein, including embodiments thereof. Each ligand protein domain includes: (1) a ligand dimerizing domain as described herein, including embodiments thereof; (2) a ligand domain as described herein, including embodiments thereof; and (3) a ligand linker connecting the ligand domain to the ligand dimerizing domain as described herein, including embodiments thereof. The ligand protein domains are bound together. In embodiments, the ligand domain is bound to one of said ligand-masking domains.

In embodiments, the masking dimerizing domains of the pharmaceutical composition are connected to a targeting domain through a targeting linker. The targeting domain and targeting linker are as described hereinabove in the Compositions section. In embodiments, the targeting linker is a cleavable targeting linker as described hereinabove in the Compositions section.

In embodiments, the ligand dimerizing domains of the pharmaceutical composition are connected to a targeting domain through a targeting linker. The targeting domain and targeting linker are as described hereinabove in the Compositions section. In embodiments, the targeting linker is a cleavable targeting linker as described hereinabove in the Compositions section.

The pharmaceutical composition of the compositions described herein may be supplied in an administration device, such as a syringe, pen, or jet injector. In embodiments, the pharmaceutical compositions described herein may be supplied as an aqueous suspension or as a powder within a vessel (which may optionally be reconstituted with a suitable diluent such as buffers, saline, or water). The vessel may be a storage device, such as an intravenous bag or other readily usable container capable of storing and protecting the pharmaceutical compositions contained therein. The vessel may be an administration device, such as a syringe, pen, or jet injector. When the vessel is a syringe or a storage device such as an intravenous bag, the pharmaceutical compositions described herein may be supplied in a concentration or dose ready for use. The pharmaceutical compositions described herein may be supplied as a kit as described herein.

III. KITS

Also provided herein are kits. In one aspect, the kits herein include a recombinant masking protein and a recombinant ligand protein. The recombinant masking protein includes two identical masking protein domains. Each masking protein domain includes: (1) a masking dimerizing domain as described herein, including embodiments thereof; (2) a ligand-masking binding domain as described herein, including embodiments thereof; and (3) a cleavable masking linker as described herein, including embodiments thereof, that connects the ligand-masking binding domain to the masking dimerizing domain. The masking protein domains are bound together. The recombinant ligand protein includes two identical ligand protein domains as described herein, including embodiments thereof. Each ligand protein domain includes: (1) a ligand dimerizing domain as described herein, including embodiments thereof; (2) a ligand domain as described herein, including embodiments thereof; and (3) a ligand linker connecting the ligand domain to the ligand dimerizing domain as described herein, including embodiments thereof. The ligand protein domains are bound together. In embodiments, the ligand domain is bound to one of said ligand-masking domains.

The recombinant masking protein and the recombinant ligand protein, including components thereof, are as described hereinabove the in compositions section. The recombinant masking protein and recombinant ligand protein may be in one container. The recombinant masking protein and recombinant ligand protein may be in separate containers. When provided in separate containers, the recombinant masking protein and the recombinant ligand protein may be mixed together and administered using the methods provided herein. The ligand domain of the recombinant ligand protein may be bound to one of the ligand masking domains of the recombinant masking protein.

The composition of the kit may be supplied in an administration device, such as a syringe, pen, or jet injector. The compositions of the kit may be supplied as an aqueous suspension or as a powder within a vessel (which may optionally be reconstituted with a suitable diluent such as buffers, saline, or water). The vessel may be a storage device, such as an intravenous bag or other readily usable container capable of storing and protecting the compositions contained therein. The vessel may be an administration device, such as a syringe, pen, or jet injector. When the vessel is a syringe or a storage device such as an intravenous bag, the pharmaceutical compositions described herein may be supplied in a concentration or dose ready for use. The pharmaceutical compositions described herein may be supplied as a kit as described herein.

IV. METHODS

Also provided herein are methods of treating a disease in a subject in need thereof. In one aspect, the method includes administering to a subject in need thereof a therapeutically effective amount of a recombinant masking protein as described herein, including embodiments thereof and a recombinant ligand protein as described herein, including embodiments thereof. In embodiments, the recombinant masking protein and the recombinant ligand protein are administered simultaneously to the subject in need. In embodiments, the recombinant masking protein and the recombinant ligand protein are administered sequentially to the subject in need (e.g. within about 1, 2, 3, 4, 5, 6 7, 8, 9, 10, 11, 12, 13, 14, 15, 16, 1, 1, 19, 20, 25, 30, 35, 40, 45, 50, 55, or 60 min of each other). In embodiments, the recombinant masking protein and the recombinant ligand protein are administered within about 1, 2, 3, 4, 5, 6, 7, 8, 9, 10, 11, 12, 13, 14, 15, 16, 17, 18, 19, 20, 22, 24, 28, 32, 36, 40, or 48 hours of each other.

In embodiments, the recombinant masking protein and the recombinant ligand protein are combined and/or administered as a pharmaceutical composition described herein, including embodiments thereof. In embodiments, the recombinant protein and recombinant ligand protein are supplied in a kit before administration to the subject in need thereof.

In embodiments of the methods herein, the ligand domain may be bound to at least one of the ligand-masking domains prior to administration. The recombinant masking protein and/or the recombinant ligand protein may independently include a targeting domain connected to the masking dimerizing domain or ligand dimerizing domain respectively through a targeting linker. The targeting domain and targeting linker are as described herein, including embodiments thereof. In embodiments, the targeting linker is a cleavable targeting linker as described herein, including embodiments thereof (e.g. the cleavable targeting linker includes a protease cleavage site).

In embodiments, the methods herein provide for decreased adverse effects associated with monoclonal antibody therapies. Thus, administration of the compositions herein may reduce acneiform eruptions, enterocolitis, dermatitis, hypophysitis, uveitis, hepatitis, nephritis, gastrointestinal irritation, cardiotoxicity, or development of progressive multifocal leukoencephalopathy. In embodiments, the methods include a reduction of co-administration of an immunosuppressant (e.g. immunosuppressant administered with monoclonal antibody therapies to limit autoimmune disorders). Thus, the compositions herein may be administered alone or be coadministered to the patient. Coadministration is meant to include simultaneous or sequential administration of the compound individually or in combination (more than one compound or agent). Thus, the preparations can also be combined, when desired, with other active substances (e.g. anticancer agents).

The compositions of the present invention can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

The method may include allowing a portion of the recombinant masking protein and the recombinant ligand protein to localize to a cancer cell or tumor. The may include allowing a cleaving agent (e.g. a protease) to cleave one or more of the cleavage sites (e.g. the cleavage site of the cleavable masking linker, the cleavable ligand linker, or cleavable targeting linker).

In embodiments, the disease is cancer, an autoimmune disease, a neurodegenerative disease, or a cardiovascular disease. The cancer may be leukemia, lymphoma, head and neck cancer, colorectal cancer, prostate cancer, melanoma, breast cancer or neuroblastoma. The cancer may be leukemia. The cancer may be lymphoma. The cancer may be head and neck cancer. The cancer may be colorectal cancer. The cancer may be prostate cancer. The cancer may be melanoma. The cancer may be breast cancer. The cancer may be neuroblastoma. The recombinant masking protein and recombinant ligand protein may be co-administered with other anti-cancer agents described herein.

In certain embodiments, the cancer cell forms part of a tumor, wherein the cleaving agent (e.g. a protease) may be located proximal to the cancer cell. The linkers described herein may be cleaved at the cleavage site. Thus, if the linker is a cleavable masking linker, the linker is cleaved at the cleavage site and the ligand-masking domain is freed. If the linker is a targeting linker, the linker may be cleaved at the cleavage site and the targeting domain is freed. The cleaving agent may be a protease. The cleaving agent may be matrix metalloproteinase (MMP). The MMP may be MMP-2 or MMP-9.

In embodiments, the autoimmune disease is Crohn's disease, rheumatoid arthritis, asthma, or psoriasis. The autoimmune disease may be Crohn's disease. The autoimmune disease may be rheumatoid arthritis. The autoimmune disease may be asthma. The autoimmune disease may be psoriasis.

The neurodegenerative disease may be Alzheimer's disease or multiple sclerosis. The neurodegenerative disease may be Alzheimer's disease. The neurodegenerative disease may be multiple sclerosis.

V. Sequences
CTLA4-Fc_WT:
(SEQ ID NO: 1)
MHVAQPAVVLASSRGIASFVCEYASPGKATEVRVTVLRQADSQVTEVCAATYMMGNELTFLDDSICT
GTSSGNQVNLTIQGLRAMDTGLYICKVELMYPPPYYLGIGNGTQIYVIDPEPCPDSDGSRSGGTSGG
GSVPLSLYSGSTSGSGKSSEGSGQASTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK.

E31A_R33A:
(SEQ ID NO: 2)
MHVAQPAVVLASSRGIASFVCEYASPGKATAVAVTVLRQADSQVTEVCAATYMMGNELTFLDDSICT
GTSSGNQVNLTIQGLRAMDTGLYICKVELMYPPPYYLGIGNGTQIYVIDPEPCPDSDGSRSGGTSGG
GSVPLSLYSGSTSGSGKSSEGSGQASTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTIPPV
LDSDGSFFLYSKLTVDKSRWQQGNVFSCSVMHEALHNHYTQKSLSLSPGK.

>E31S:
(SEQ ID NO: 3)
MHVAQPAVVLASSRGIASFVCEYASPGKATSVRVTVLRQADSQVTEVCAATYMMGNELTFLDDSICT
GTSSGNQVNLTIQGLRAMDTGLYICKVELMYPPPYYLGIGNGTQIYVIDPEPCPDSDGSRSGGTSGG
GSVPLSLYSGSTSGSGKSSEGSGQASTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTIPPV
LDSDGSFFLYSKLTVDKSRWQQGNVFSCSVMHEALHNHYTQKSLSLSPGK.

E31K:
(SEQ ID NO: 4)
MHVAQPAVVLASSRGIASFVCEYASPGKATKVRVTVLRQADSQVTEVCAATYMMGNELTFLDDSICT
GTSSGNQVNLTIQGLRAMDTGLYICKVELMYPPPYYLGIGNGTQIYVIDPEPCPDSDGSRSGGTSGG
GSVPLSLYSGSTSGSGKSSEGSGQASTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTIPPV
LDSDGSFFLYSKLTVDKSRWQQGNVFSCSVMHEALHNHYTQKSLSLSPGK.

E31R:
(SEQ ID NO: 5)
MHVAQPAVVLASSRGIASFVCEYASPGKATRVRVTVLRQADSQVTEVCAATYMMGNELTFLDDSICT
GTSSGNQVNLTIQGLRAMDTGLYICKVELMYPPPYYLGIGNGTQIYVIDPEPCPDSDGSRSGGTSGG
GSVPLSLYSGSTSGSGKSSEGSGQASTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTIPPV
LDSDGSFFLYSKLTVDKSRWQQGNVFSCSVMHEALHNHYTQKSLSLSPGK.

E31S_R33E_T51H:
(SEQ ID NO: 6)
MHVAQPAVVLASSRGIASFVCEYASPGKATSVEVTVLRQADSQVTEVCAAHYMMGNELTFLDDSICT
GTSSGNQVNLTIQGLRAMDTGLYICKVELMYPPPYYLGIGNGTQIYVIDPEPCPDSDGSRSGGTSGG
GSVPLSLYSGSTSGSGKSSEGSGQASTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALPA

-continued
```
PIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK.

T51H:
                                                            (SEQ ID NO: 7)
MHVAQPAVVLASSRGIASFVCEYASPGKATEVRVTVLRQADSQVTEVCAAHYMMGNELTFLDDSICT

GTSSGNQVNLTIQGLRAMDTGLYICKVELMYPPPYYLGIGNGTQIYVIDPEPCPDSDGSRSGGTSGG

GSVPLSLYSGSTSGSGKSSEGSGQASTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK.

K95A
                                                            (SEQ ID NO: 8)
MHVAQPAVVLASSRGIASFVCEYASPGKATEVRVTVLRQADSQVTEVCAATYMMGNELTFLDDSICT

GTSSGNQVNLTIQGLRAMDTGLYICAVELMYPPPYYLGIGNGTQIYVIDPEPCPDSDGSRSGGTSGG

GSVPLSLYSGSTSGSGKSSEGSGQASTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK.

E97A:
                                                            (SEQ ID NO: 9)
HVAQPAVVLASSRGIASFVCEYASPGKATEVRVTVLRQADSQVTEVCAATYMMGNELTFLDDSICTG

TSSGNQVNLTIQGLRAMDTGLYICKVALMYPPPYYLGIGNGTQIYVIDPEPCPDSDGSRSGGTSGGG

SVPLSLYSGSTSGSGKSSEGSGQASTHTCPPCPAPELLGGPSVFLFPPKPKDTLMISRTPEVTCVVV

DVSHEDPEVKFNWYVDGVEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK.

K95A_E97A:
                                                           (SEQ ID NO: 10)
MHVAQPAVVLASSRGIASFVCEYASPGKATEVRVTVLRQADSQVTEVCAATYMMGNELTFLDDSICT

GTSSGNQVNLTIQGLRAMDTGLYICAVALMYPPPYYLGIGNGTQIYVIDPEPCPDSDGSRSGGTSGG

GSVPLSLYSGSTSGSGKSSEGSGQASTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK.
```

VI. EXAMPLES

1. Example 1

Despite major advances, locally advanced and metastatic prostate cancer remain a clinical challenge. In contrast to early, non-disseminated prostate cancer, advance prostate cancer cannot be cured by current treatment modalities. In addition to chemotherapy, radiation and hormone therapy, immunotherapy has recently left its mark on prostate cancer management (see the approval of Sipuleucel-T for the treatment of late-stage prostate cancer). In other cancers, such as advanced melanoma, dramatic improvements in overall survival of patients were reported with a monoclonal antibody (MDX-010, ipilimumab) that recognizes and blocks the immunosuppressive cytotoxic T-lymphocyte antigen (CTLA)-4 receptor on T cells. Hodi, 2010. These results ultimately led to FDA-approval of ipilimumab for the treatment of advanced melanoma. Furthermore and of particular importance to this application, phase-III clinical studies are currently being conducted to explore the use of ipilimumab in advanced prostate cancer and other neoplastic diseases.

However, ipilimumab can cause severe (grade 3-4) systemic adverse events reflecting immune-mediated toxicities. Beck, 2006; Phan, 2008; Weber, 2008. These include enterocolitis, dermatitis, hypophysitis, uveitis, hepatitis, and nephritis. Enterocolitis is the most common major toxicity (21% of patients) requiring extensive countermeasures including colectomy due to perforation of the colon in several patients. Beck, 2006. The apparent risks of systemic CTLA-4 blockade raise questions regarding its use. Herein, it was discovered, inter alia, that directing these agents to tumor sites spares normal tissues and appears to be an alternative and safer approach. This discovery enhances the therapeutic ratio of CTLA-4 antagonists including ipilimumab and an engineered lipocalin2 derivative recently developed as an effective CTLA-4 antagonist. Schonfeld, 2009.

Most protein-based therapies currently in clinical use target molecular mechanisms but not disease sites. With few exceptions (such as lipocalin2) these are monoclonal antibodies (mAbs) which bind to diseased cells or to T cells (as in the case of ipilimumab). However, these monoclonal antibodies engage these targets in normal tissues and give rise to adverse events with various degrees of severity. If the therapeutic agent induces autoimmune phenomena, the toxicity not only leads to significant morbidity but often necessitates the administration of immunosuppressants (corticosteroids, TNF-α inhibitors) which may blunt therapeutic intent.

Thus, herein, the 'targeted release' of proteins at disease sites was investigated. This concept relates to the reversible occlusion or 'reversible masking' of reactive sites by ligands which can be removed by proteases present and active at disease sites. In the case of mAbs, the occluding moieties are recombinant antigen (Ag) fragments covalently linked to heavy or light IgG chains. In this design, the Ag fragment occludes the antigen binding sites on the IgG and, thus, prevents binding to native antigen on target cells. However, the linker tethering the Ag fragment to the mAb contains protease cleavage sites which are susceptible to tumor-associated proteases (for example matrix metalloproteinases (MMPs)). Cleavage of the linker in the tumor microenvironment reduces the strength (valency) of the intermolecular interaction, dissociation of the complex and engagement of native Ag on tumor or resident normal cells. It has been previously demonstrated that reversible masking of the EGFR antagonistic antibodies cetuximab (C225) and matuzumab (425) is feasible. Donaldson, 2009. However, these prior studies were not directed to non-IgG molecules such as CTLA-4 antagonists to restrict its immunostimulatory effects to the tumor environment (see FIG. 1 panel A).

The CTLA-4 antagonist of choice is modified lipocalin2 (m-Lcn2) which has been optimized to engage CTLA and to reverse CTLA-4-dependent immunosuppression. Schonfeld, 2009. M-Lcn2 was selected due to several favorable molecular characteristics. First, it is a stable soluble CTLA-4 ligand of which several variants with different affinities for CTLA-4 ranging from ~100 nM to 250 pM have been identified. Secondly, the m-Lcn2 monomer is small (~180 aa) as compared to IgG, yet it acts in a manner similar to ipilimumab as regards CTLA-4 antagonism. Thirdly, m-Lcn2 binds to and blocks both human and murine CTLA-4 enabling studies in syngeneic mouse tumor models as proposed here. Lastly, detailed structural knowledge of the m-Lcn2 interaction with CTLA-4 (Schonfeld, 2009) allows design of a m-Lcn2/CTLA fragments that will readily dissociate upon MMP9 cleavage. Local CTLA-4 blockade at tumor sites has previously been tested by using B16 melanoma cells engineered to secrete a CTLA-4 antagonistic antibody Simmons, 2008. The previous work showed that local delivery of anti-CTLA-4 IgG secreted by GM-CSF-producing tumor cell-based vaccines activated potent anti-tumor responses associated with low circulating mAb levels in the host. Importantly, lowering the systemic exposure of the host to the anti-CTLA-4 also correlated with reduced systemic autoimmunity.

Herein, are described different reversible recombinant masked m-Lcn2 variants and testing of their immunostimulatory properties in vitro and in vivo using appropriate mouse cancer models.

Different versions of CTLA-4 antagonists tested provide effective CTLA-4 blockade at tumor sites while exhibiting a reduced adverse side effect profile compared to systemically active CTLA-4 antagonists. m-Lcn2, a re-engineered human lipocalin that binds both murine and human CTLA4 with high affinity and which enables us to translate successful outcomes in murine studies to human clinical trials will be the focus. m-Lcn2 is monovalent whereas ipilumumab (and nearly all approved mAb-based therapeutics) are bivalent. Thus, to mimic ipilumumab and leverage affinity gains by avidity, a bivalent analog was created (FIG. 2 panel A). Specifically, we fused m-Lcn2 to a human IgG1 Fc-fragment.

The bivalent nature of m-Lcn2-Fc is also critical in creating a non-covalent tumor-activated, bivalent mask. To create the m-Lcn2 mask, CTLA-4 was fused to the N-terminus of the IgG1 Fc through a flexible linker encoding a protease recognition sequence (MMP9) that is cleaved by a protease (MMP9) present and active at prostate cancer sites (FIG. 2 panel B). Cleavage of the MMP9 linker reverts the valency of the mask to a monomeric interaction, significantly reduces the affinity of the masking moiety, and permits the bivalent m-Lcn2 to associate with TIL-associated CTLA-4 (FIG. 1). The cleaved, monomeric CTLA-4, which cannot compete with endogenous, multimeric CTLA-4, is predicted to diffuse away from the tumor microenvironment (see FIG. 1).

By reversibly masking m-Lcn2, systemic administration to disease sites is achieved by cleavage of the mask and differential affinity at the tumor site. To add a 'second layer' of tumor targeting, we fused scFv recognizing a tumor-specific antigen to either the m-Lcn2 or to the mask (FIG. 2 panels C and D). Without being bound by any particular theory, we hypothesize that anchoring the masked m-Lcn2 complex at the tumor site will increase the residence time at the tumor, enhance its proteolytic cleavage and facilitate unmasking. To accomplish this, scFv will be fused to the C-terminus of the Fc (Czajkowsky, 2012) through a Gly-Ser linker with and without an MMP9 site. To enable in vivo studies in an appropriate prostate cancer mouse model (ProTRAMP mice), we will use a hemagglutinin (HA) scFv. Zhang, 2010.

Separating the mask from the m-Lcn2-Fc simplifies the optimization and characterization of the therapeutic moiety (e.g., m-Lcn2-Fc). The linker and the protease site, can be independently matched and optimized to the tumor. Using a Fc domain for dimerization is advantageous, in part due to the fact that Fc containing biologic agents (mAbs) constructs are in clinical use, but also since Fc fusions frequently express well, are easily purified using protein A/L, resins, and offer favorable PK/PD properties.

Collectively, these constructs described here provide a broad platform to test whether antagonizing CTLA-4 expressed by TILs at tumor sites is feasible and effective in mitigating adverse side effects associated with this treatment modality.

Before creating the bivalent m-Lcn2-Fc construct, we first verified that the monovalent m-Lcn2 binds to human CTLA4 as described by Skerra and colleagues. Schonfeld, 2009. The m-Lcn2 cDNA was commercially synthesized and subcloned into a bacterial expression vector. The protein was isolated from the periplasm and purified to homogeneity by standard methods (>95% by SDS-PAGE). The binding affinity of this construct was determined using surface plasmon resonance (SPR) wherein CTLA-4-Fc (purchased from R&D systems) was chemically tethered to CMS chip. The affinity was essentially identical to the reported value.

Next, the same m-Lcn2 cDNA was subcloned N-terminal to a linker-Fc domain present in an insect expression vector. Viral stocks were produced, titrated and used to express the construct. The secreted product was purified to homogeneity using standard methods. The same process was carried out for the CTLA-4 mask. The MMP9 site was incorporated through site directed mutagenesis.

Figure 3:
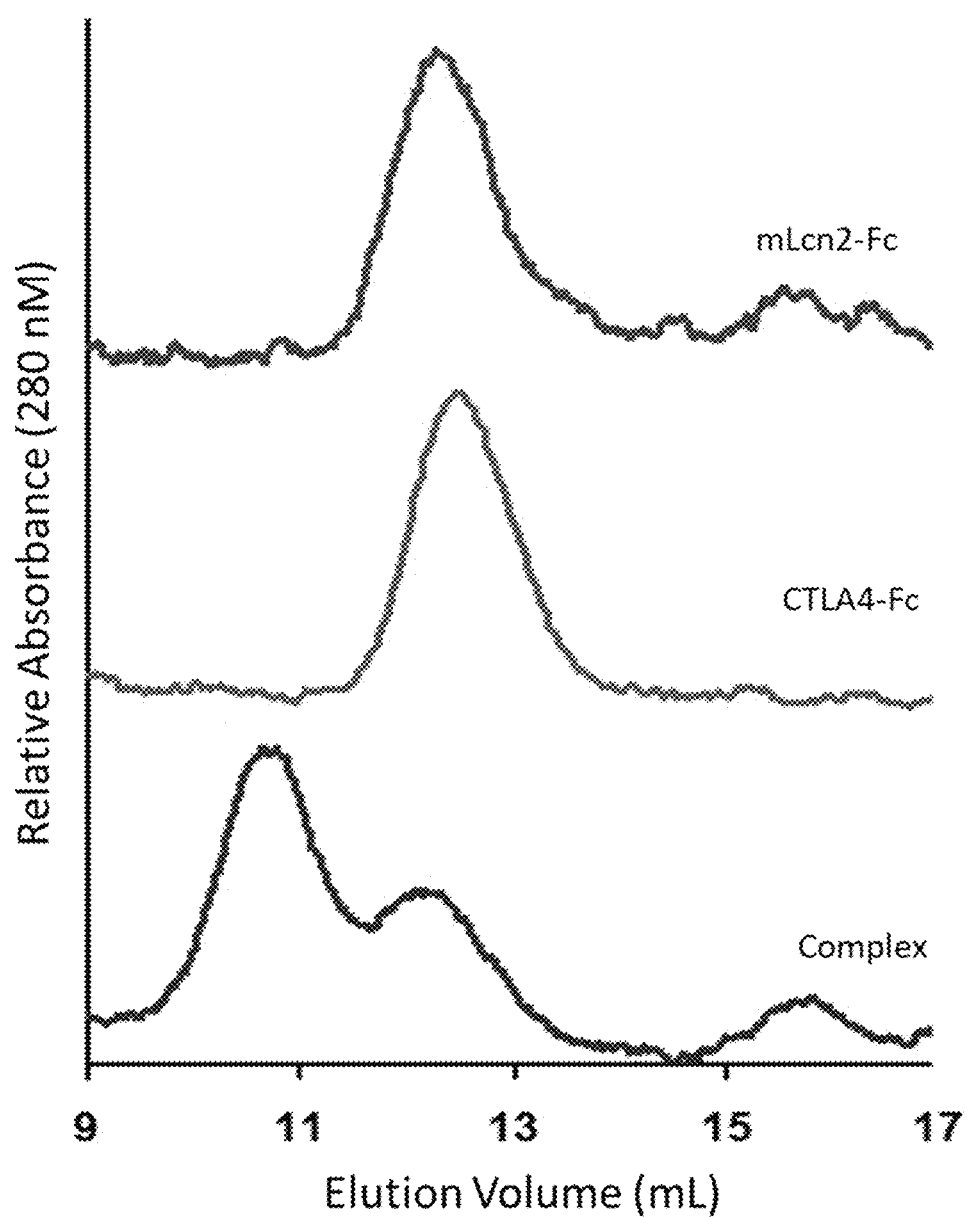
FIG. 3: Characterization of mask prototype complex with m-Lcn2-Fc and CTLA-4-Fc: A) SEC indicates the formation of a complex (orange trace) at 11.4 mL; B) SPR traces indicate m-Lcn2-Fc binds with high affinity to CTLA-4-MMP9-Fc (highest concentration is 300 nM). C) SDS-PAGE of CTLA-4-MMP9-Fc before and after 8 hrs of MMP9 treatment (control is a mutated the MMP9 site that was not cleaved by MMP9 (right panel)).
Figure 3:
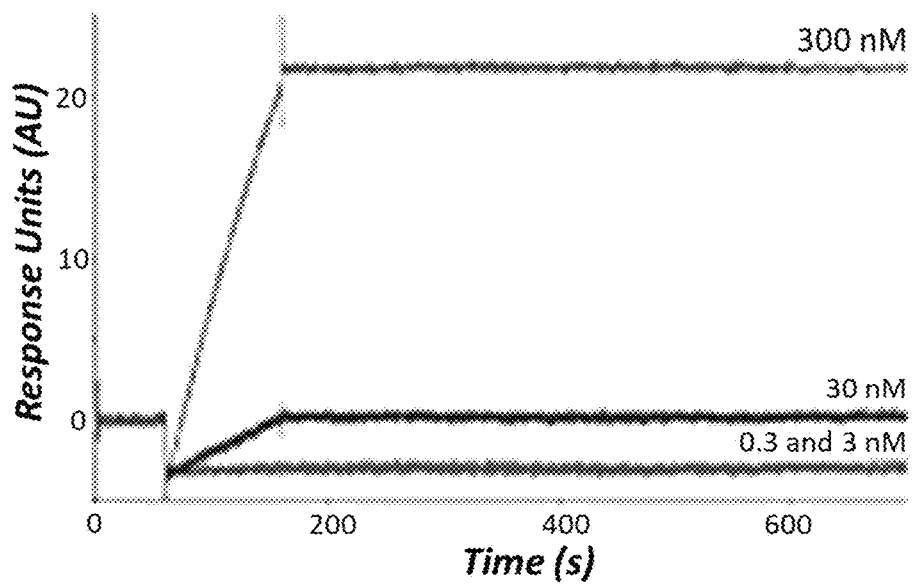
Figure 3:
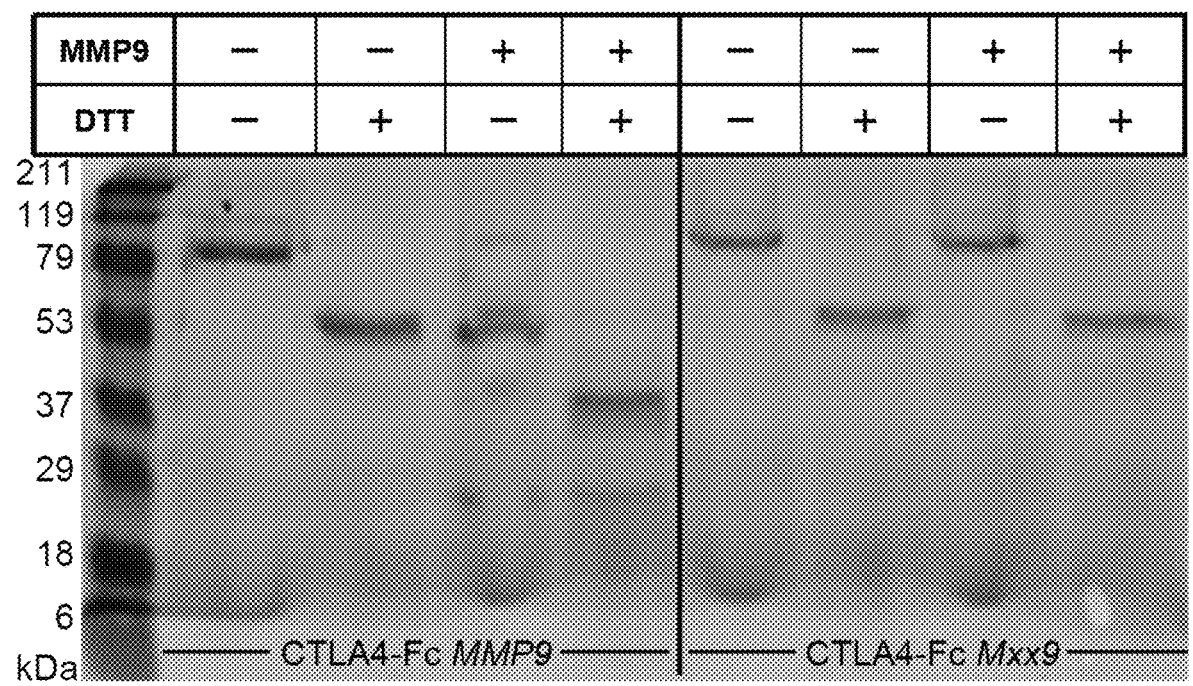

To verify that the m-Lcn2-Fc and CTLA-4-Fc form a 1:1 complex, we used analytical size exclusion chromatography (SEC) (FIG. 3 panel A). A definitive shift to earlier elution volumes was observed, consistent with a molecular mass of 200 kD, as expected. To verify an increase in the apparent affinity due to the energy additivity of bivalent-bivalent interaction, the mask, CTLA-4-MMP9-Fc, was coupled to a CM5 sensor chip and titrated with the bivalent m-Lcn2-Fc. A substantial increase in affinity was observed. In fact, no dissociation was observed and thus no calculation could be completed for an apparent dissociation constant (FIG. 3 panel B). An approximate upper limit is estimated at $K_D=200$ pM. In an attempt to establish the off-rate, a competition assay was carried out. Specifically, the 1:1 m-Lcn2-Fc|CTLA-4-MMP9-Fc complex was isolated and incubated with 10 fold excess of Alexafluor-labeled CTLA-4-MMP9-Fc. The exchange by size exclusion chromatography was followed by monitoring at 495 nM. After two weeks, less than 5% exchange was observed. Taken together, these results suggest that the bivalent m-Lcn2-Fc/CTLA-4-Fc complex is stable well beyond its predicted biological half-life (<3-5 days) upon administration in vivo.

Figure 4:
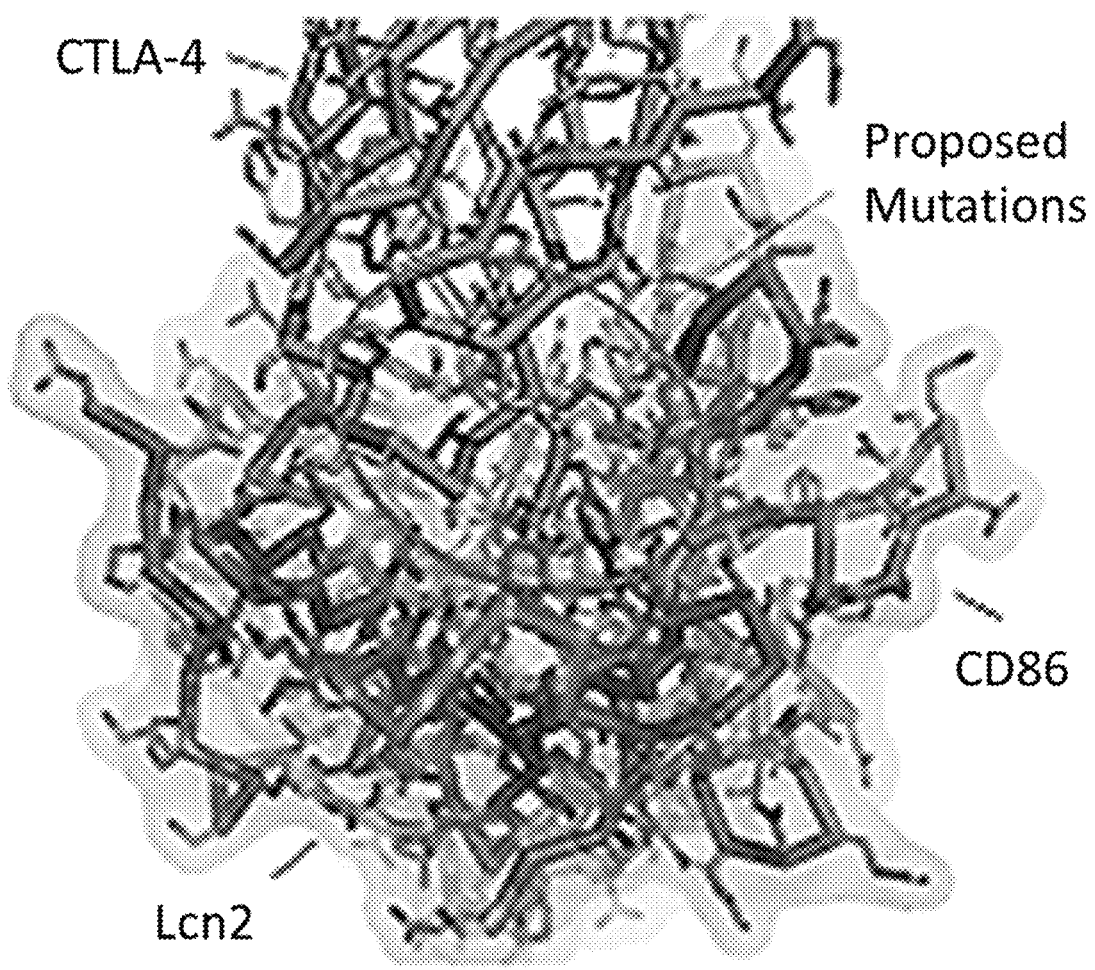
FIG. 4: Proposed mutations in the CTLA-4 mask to facilitate unmasking and block CTLA-4 receptor binding on cells.

Recombinant MMP9 was demonstrated to effectively cleave the CTLA4-MMP9-Fc mask (FIG. 3 panel C), but not the m-Lcn2-Fc. To enhance the dissociation rate after MMP9 cleavage, we superimposed the structures of CTLA-4 bound to CD80, CD86 and m-Lcn2. Based on this superposition, mutations in CTLA-4 were identified that can be introduced individually (or in combination to lower the affinity of the m-Lcn2 mask and simultaneously reduce the affinity of the cleaved CTLA-4 to cell-associated CD80/86 (FIG. 4). These include Thr32, Glu33, Tyr100 and Tyr104. Each is at the Lcn2 and CD80/86 interface and each is surface exposed.

Each will be mutated to alanine, expressed, purified and characterized by SPR (monovalent m-Lcn2 and m-Lcn2-Fc will be chemically tethered to individual channels of the SPR chip). In particular, we seek to reduce the lifetime of the monovalent interaction ($K_{OFF}=5.1\times10^{-4}$ s$^{-1}$; $t_{1/2}=0.693/K_{OFF}=22$ mins). A 10-fold increase in the off-rate would mitigate potential loss of the tumor localization of the m-Lcn2-Fc due to diffusion back to the blood stream. Reducing the affinity of the individual interactions will affect the overall affinity of the bivalent mask to the bivalent m-Lcn2-Fc (e.g., 100 fold weaker). Due to significant gains in affinity due to avidity, we expect efficient masking (e.g., 320 nM×320 nM=100 fM), however, we will immediately observe significant losses in the SPR experiments. Such losses reflect potential issues within the linker (e.g., too long, too flexible, too restricted). Issues with the linkers require creating a series of linkers between the Fc and the CTLA4 portions of the mask. First, we reduce the length in an iterative fashion (e.g., remove 2 residues per cycle until we lose avidity). Next, we alter the amino acid sequence. The linker is composed primarily of glycines beyond the MMP9 cleavage site. To reduce the flexibility inherent in glycine repeat sequences, we add serines, threonines and/or glutamines. In each iteration, we test the affinity by SPR and the MMP9 susceptibility of the complex.

The cleavage of the mask by MMP9 will be optimized. Given the apparent affinity of the bivalent mask is sufficient, we alter the position of the MMP9 site. Specifically, we move the site to the N-terminal and C-terminal position of the linker. We compare the proteolytic rate of each in the presence of the m-Lcn2-Fc. The linker may be extended to make the site more solvent exposed. We add residues to the N- and C-termini of the linker. As before, each will be characterized by SPR to ensure efficient masking.

An scFv that recognizes HA will be fused to the C-terminus of the Fc domain in both the m-Lcn2-Fc construct and the CTLA-4 mask. Zhang, 2010. The inclusion of this domain allows tumor targeting, but also sufficiently extends the residence time at the tumor for efficient proteolysis. It also counteracts extended off-rates of the mask. The cDNA will be commercially synthesized and subcloned into the current constructs. We characterize by SPR the affinity the scFv to HA and ensure that its presence does not affect the binding of Lcn2 for CTLA-4 and vice versa. We will also characterize MMP9 proteolytic cleavage. Similar iterations as outlined above will be carried out if necessary.

We test functionally whether masking of m-Lcn2 disrupts its ability to boost T cell activation and whether unmasking restores T cell activation. This can be done using in vitro assays of T cell activation. In vitro screening is a cost-effective way to select optimized candidates for in vivo testing of anti-tumor effects and immune activation. Specifically we test whether the m-Lcn2 construct enhances naive and antigen-specific (OT-1) T cell activity. In addition to masked constructs we test constructs targeted to prostate cells by linking scFvs recognizing hemagglutinin expressed selectively in the prostate. We assess the effect of masking/tumor cell targeting of m-Lcn2 variants on immune effector functions in the presence and absence of recombinant MMP9 as appropriate and by using controls in which linkers do not contain MMP-9 cleavable sites.

Previous work has shown that CTLA-4 antagonistic antibodies augment efficacy of immunotherapeutic approaches to mouse tumors including B16 melanoma (Quezada, 2006; Curran, 2010; Korman, 2005; Gregor, 2004) and TRAMP-C2 prostate cancer cells (Kwon, 1999; Waitz, 2012). Specifically Waitz, et al showed effective but not complete growth inhibition of subcutaneous TRAMP-C2 grafts in C57/B16 mice by a combination of cryoablation and antibody-mediated CTLA-4 blockade. By contrast, CTLA-4 blockade alone was insufficient for tumor growth inhibition. Based on these findings, the TRAMP-C2 implant model is highly suitable for assaying anti-tumor effects of cleavable and uncleavable m-Lcn2 constructs alone or in combination with cryoablation. This model will likely not accommodate testing the masked m-Lcn2-Fc design equipped with tumor-targeted sc-Fvs as we do not have access to antibodies recognizing tumor-associated antigens on TRAMP cells and SV40T is not detectable on the cell surface of TRAMP prostate epithelial cells.

Instead, we use a different model system generated to avoid these issues. TRAMP mice were crossed with mice expressing hemagglutinin under control of the probasin promoter. See Getnet, 2009; Grosso, 2007. In this double transgenic model (referred to in the following as Pro-TRAMP), hemagglutinin represents a prostate-associated antigen co-expressed with SV40T in both normal and transformed parenchymal prostate cells. Therefore, tumor tissue targeting will be achieved by C-terminally linking HA-specific scFvs onto the Fc fragment of the mLcn-2Fc construct.

In addition to testing efficacy of masked, cleavable m-Lcn2 constructs we focus on (i) monitoring potential adverse events induced by CTLA-4 blockade in mice (ii) testing whether masking m-Lcn2 reduces such adverse effects and, (iii) assessing redistribution of m-Lcn2 to tumor tissues. Regardless of the extent of adverse events associated with m-Lcn2 administration, this model system provides important information on biodistribution of masked m-Lcn2 constructs critical to the avoidance or reduction of adverse events in patients. Tumor-specific immune responses in all experimental and control animals will be assessed and as shown in Table 1. Novak, 2007.

To assess how m-Lcn2-mediated blockade of cell-associated CTLA-4 affects antigen-specific activation of the T cells, we will generate TRAMP-C2 cells expressing chicken ovalbumin (Ova) reporter by stable transduction of the cells with a plasmid encoding full-length Ova. The resultant TRAMP-C2-Ova cells will be used for the analysis of the IFNγ production and cytotoxic T lymphocyte (CTL) activity of Ova-SIINFEKL peptide-specific T cells isolated from OT-I transgenic mice. Production of IFNγ by the activated T cells in the absence or presence of the CTLA-4 blockade will be assessed by ELISpot assay a commercial kit (eBioscience). Analysis of CTL activity will be done using TRAMP-C2-Ova activated OT-I cells as described below for B16 mouse melanoma cells (Table 2). All assays will be done in triplicates using OT-I cells activated in vitro by the pre-incubation with TRAMP-C2-Ova cells in the absence of presence of the recombinant proteins under investigation.

TABLE 2

T-cell activation by masked and unmasked m-Lcn2-Fc proteins.

| | In vitro stimulation assay |
|---|---|
| B16-OVA | 15 |
| | 14 |
| B16-OVA + m-Lcn2-Fc | 167 |
| | 159 |
| B16-OVA + masked m-Lcn2-Fc | 24 |
| | 20 |

*Elispot assays (IFN-γ) were performed following MLR using splenocytes isolated from OT-1 (ovalbumin-specific TCR transgenic) mice after stimulation in vitro (5 d) with B16 melanoma cells expressing Ova peptide in the presence and absence of recombinant masked and unmasked m-Lcn2 constructs as indicated and as shown in FIG. 1. Note 10-fold induction of IFN-γ production by unmasked but not by masked m-Lcn2-Fc.

We have tested the effects of masked and unmasked prototypic m-Lcn2-Fc constructs (FIG. 1) using Ova-expressing B16 melanoma cells and splenocytes derived from OT-1 mice (Table 2). This experiment revealed a marked increase in IFNγ production associated with bivalent m-Lcn2-Fc treatment which was reversible to almost background levels by use of the bivalent CTLA-4 mask. Similar results were obtained using splenocytes from naive mice stimulated with phetohemagglutinin. Based on these very promising results we anticipate to advance at least two masked m-Lcn2 designs in mice. One of these is a version of the prototypical design shown in FIG. 1 panel A, whereas the second will be one of the tumor-targeted design containing anti-HA scFvs and schematically shown in FIG. 2. Selection of the optimized construct will be done by a combination of biophysical (SPR) and functional assays.

Effects of Reversibly Masked m-Lcn2 on TRAMP-C2 Growth in C56BL/6 Mice.

To assess efficacy of the non-targeted, masked m-Lcn2-Fc/CTLA4-Fc complexes we will use a model based on inhibition of TRAMP-C2 cells upon subcutaneous grafting to male C57BL/6 mice. Waitz, 2012. *Mycoplasma*-free (PCR-tested) TRAMP-C2 cells ($1 \times 10^6$) will be inoculated subcutaneously into the left flank of mice. After 28 d tumors will be cryoablated followed by a $2^{nd}$ inoculation of $0.2 \times 10^6$ TRAMP-C2 cells in the right flank. Masked and unmasked m-Lcn2-Fc proteins will be injected on days 1, 4, 7, and 10 after the $2^{nd}$ inoculation and tumor growth monitored for further 60 days. Controls will consist of constructs and complexes rendered MMP9 resistant by introducing point mutations in the MMP consensus site; these variants proteins are not expected to inhibit tumor growth. Hamster IgG (negative control) and the anti-mouse 9H10 antibody (positive control) are purchased from BD Biosciences. We will use 100-200 µg of IgG/injection and equimolar concentrations of masked and unmasked recombinant m-Lcn2-Fc proteins.

In this model neither single modality cryoablation nor anti-CTLA-4 treatment protect and all mice die within 30 days of the $2^{nd}$ tumor cell inoculation. Waitz, 2012. In contrast, cryoablation combined with CTLA-4 blockade by 9H10 confers long-term protection (>60 days) to approximately 50% of mice. We expect the cleavable masked and unmasked m-Lcn2 constructs produce long-term protection. By contrast the uncleavable versions of these proteins should not provide any protection. If protection is observed in this setting we plan to also test whether protection can be achieved by recombinant, cleavable m-Lcn2 alone in the absence of cryoablation. As TRAMP-C2 cells overexpress MMP9 we will perform these assays with unmodified TRAMP-C2s. If necessary we will transfect TRAMP-C2 cells with a plasmid encoding MMP9 and use cells secreting high levels of active MMP9.

Independently of the potential therapeutic effect of masked m-Lcn2 we will determine whether reversible masking leads to reduced incidence or severity of autoimmune parameters in mice treated with CTLA-4 antagonists. Quantification of "autoimmune" status in treated mice will be done by determining the levels of autoantibodies reactive with anti-nuclear antibodies ANA, sSDNA, and dsDNA using commercial ELISA kits. These parameters were chosen based on previous work assessing systemic immune related events associated with vaccination strategies in mice (Hodge, 2003) and showing significant increases of these antibodies in the circulation when CTLA-4 antagonistic antibody was systemically administered to mice (Simmons, 2008). These experiments will reveal whether 'naked' m-Lcn2 triggers systemic immune responses in a manner similar to CTLA-4 antagonistic antibodies and whether reversibly masked m-Lcn2 will reduce systemic immune responses. Serum will be collected at several time points within 2 weeks of m-Lcn2 variant protein administration. We will also assay biodistribution of cleavable and non-cleavable m-Lcn2 in TRAMP-C2 tumor tissue in mice to document interaction of unmasked m-Lcn2 interacts with TILs in situ. This will be done by double staining tissue sections for T cell surface markers (CD4, CD8) and m-Lcn2 using an antibody recognizing the His-tag which is not removed by MMP9. We will further detect cleaved and uncleaved m-Lcn2 in sera of treated mice by immunoblot analysis.

Second generation unmasked or masked m-Lcn2 constructs targeted to prostate cancer will be tested in vivo using ProTRAIVIP mice in which prostate epithelia express the model influenza hemagglutinin under control of a prostate-specific minimal rat probasin promoter (Drake, 2005 #1818). Using this model will make it possible to monitor immune phenomena associated with CTLA-4 blockade directed to tumor/tissue sites as it leads to intraprostatic infiltration and accumulation of clonotypic, HA-specific cytotoxic T-cells. Drake, 2005. This model also mimics the situation of several prostate cancer-associated antigens in human prostate cancer which would ultimately serve to target recombinant CTLA-4 antagonists to human disease sites.

We will use this model to demonstrate enrichment of anti-HA-enabled CTLA-4 antagonists in the prostate. This will be done by i.p. injection of these and control recombinant proteins that do not contain anti-HA scFv sequences into tumor-bearing animals (>10-weeks old) followed by detection of these in different tissues using commercially available anti-His and anti-human Fc antibodies.

Secondly, we will test whether targeting m-Lcn2-Fc or monomeric m-Lcn2 to the prostate delays or inhibits tumor development in ProTRAMP mice. These mice develop tumors with similar kinetics as TRAMP mice. Drake, 2005. To asssay effects of CTLA-4 blockade on tumor development in these mice we plan to take advantage of a mouse model to monitor abscopal effects of radiation therapy in combination with immunotherapy. Harris, 2008. Specifically we will perform pelvic irradiation of 20-24 week old ProTRAMP mice followed by CTLA-4 antagonist administration within 3 to 5 weeks after irradiation. This time regimen has been found by Harris et al. to be superior to others in enabling anti-tumor immune responses in ProTRAMP mice.

It is expected that the scFv-enabled m-Lcn2 proteins (monomers an or Fc-enabled dimers) preferentially localize to the prostate and are more effective in inhibiting the development of spontaneous prostate cancer in this model.

The antigen binding site of trastuzumab, domain IV of the Her2 receptor, was tethered to the dimeric Fc region of the human IgG1 through a flexible peptide linker containing a tumor-specific protease site, MMP. This approach offered significant advantages over the covalent masked antibodies, because the non-covalent Fc masks can be added to mAbs already in the clinic. This mitigates the testing and optimization of modified mAbs. Further, a single cleavage of the non-covalent mask reduces the valency of the mask and initiates immediate release the mAb.

1. Example 2

| Boxshade alignment | | |
|---|---|---|
| CTLA4-Fc_WT | 1 | MHVAQPAVVLASSRGIASFVCEYASPGKATEVRVTVLRQADSQVTEVCAATYMMGNELTF |
| E31S | 1 | MHVAQPAVVLASSRGIASFVCEYASPGKATSVRVTVLRQADSQVTEVCAATYMMGNELTF |
| T51H | 1 | MHVAQPAVVLASSRGIASFVCEYASPGKATEVRVTVLRQADSQVTEVCAAHYMMGNELTF |
| E31A R33A | 1 | MHVAQPAVVLASSRGIASFVCEYASPGKATAVAVTVLRQADSQVTEVCAATYMMGNELTF |
| E31S_R33E_T51H | 1 | MHVAQPAVVLASSRGIASFVCEYASPGKATSVEVTVLRQADSQVTEVCAAHYMMGNELTF |
| | | |
| CTLA4-Fc_WT | 61 | LDDSICTGTSSGNQVNLTIQGLRAMDTGLYICKVELMYPPPYYLGIGNGTQTYVIDPEPC |
| E31S | 61 | LDDSICTGTSSGNQVNLTIQGLRAMDTGLYICKVELMYPPPYYLGIGNGTQTYVIDPEPC |
| T51H | 61 | LDDSICTGTSSGNQVNLTIQGLRAMDTGLYICKVELMYPPPYYLGIGNGTQTYVIDPEPC |
| E31A_R33A | 61 | LDDSICTGTSSGNQVNLTIQGLRAMDTGLYICKVELMYPPPYYLGIGNGTQTYVIDPEPC |
| E31S R33E T51H | 61 | LDDSICTGTSSGNQVNLTIQGLRAMDTGLYICKVELMYPPPYYLGIGNGTQTYVIDPEPC |
| | | |
| CTLA4-Fc_WT | 121 | PDSDGSRSGGTSGGGSVPLSLYSGSTSGSGKSSEGSGQASTHTCPPCPAPELLGGPSVFL |
| E31S | 121 | PDSDGSRSGGTSGGGSVPLSLYSGSTSGSGKSSEGSGQASTHTCPPCPAPELLGGPSVFL |
| T51H | 121 | PDSDGSRSGGTSGGGSVPLSLYSGSTSGSGKSSEGSGQASTHTCPPCPAPELLGGPSVFL |
| E31A_R33A | 121 | PDSDGSRSGGTSGGGSVPLSLYSGSTSGSGKSSEGSGQASTHTCPPCPAPELLGGPSVFL |
| E31S R33E T51H | 121 | PDSDGSRSGGTSGGGSVPLSLYSGSTSGSGKSSEGSGQASTHTCPPCPAPELLGGPSVFL |
| | | |
| CTLA4-Fc_WT | 181 | FPPKPKDTLMISRTPEVTCVVVDVSHEDPEVKFNWYVDGVEVHNAKTKPREEQYNSTYRV |
| E31S | 181 | FPPKPKDTLMISRTPEVTCVVVDVSHEDPEVKFNWYVDGVEVHNAKTKPREEQYNSTYRV |
| T51H | 181 | FPPKPKDTLMISRTPEVTCVVVDVSHEDPEVKFNWYVDGVEVHNAKTKPREEQYNSTYRV |
| E31A_R33A | 181 | FPPKPKDTLMISRTPEVTCVVVDVSHEDPEVKFNWYVDGVEVHNAKTKPREEQYNSTYRV |
| E31S R33E T51H | 181 | FPPKPKDTLMISRTPEVTCVVVDVSHEDPEVKFNWYVDGVEVHNAKTKPREEQYNSTYRV |
| | | |
| CTLA4-Fc WT | 241 | VSVLTVLHQDWLNGKEYKCKVSNKALPAPIEKTISKAKGQPREPQVYTLPPSRDELTKNQ |
| E31S | 241 | VSVLTVLHQDWLNGKEYKCKVSNKALPAPIEKTISKAKGQPREPQVYTLPPSRDELTKNQ |
| T51H | 241 | VSVLTVLHQDWLNGKEYKCKVSNKALPAPIEKTISKAKGQPREPQVYTLPPSRDELTKNQ |
| E31A_R33A | 241 | VSVLTVLHQDWLNGKEYKCKVSNKALPAPIEKTISKAKGQPREPQVYTLPPSRDELTKNQ |
| E31S R33E T51H | 241 | VSVLTVLHQDWLNGKEYKCKVSNKALPAPIEKTISKAKGQPREPQVYTLPPSRDELTKNQ |
| | | |
| CTLA4-Fc WT | 301 | VSLTCLVKGFYPSDIAVEWESNGQPENNYKTTPPVLDSDGSFFLYSKLTVDKSRWQQGNV |
| E31S | 301 | VSLTCLVKGFYPSDIAVEWESNGQPENNYKTTPPVLDSDGSFFLYSKLTVDKSRWQQGNV |
| T51H | 301 | VSLTCLVKGFYPSDIAVEWESNGQPENNYKTTPPVLDSDGSFFLYSKLTVDKSRWQQGNV |
| E31A_R33A | 301 | VSLTCLVKGFYPSDIAVEWESNGQPENNYKTTPPVLDSDGSFFLYSKLTVDKSRWQQGNV |
| E31S_R33E_T51H | 301 | VSLTCLVKGFYPSDIAVEWESNGQPENNYKTTPPVLDSDGSFFLYSKLTVDKSRWQQGNV |
| | | |
| CTLA4-Fc WT | 361 | FSCSVMHEALHNHYTQKSLSLSPGK [SEQ ID NO: 1] |
| E315 | 361 | FSCSVMHEALHNHYTQKSLSLSPGK [SEQ ID NO: 3] |
| T51H | 361 | FSCSVMHEALHNHYTQKSLSLSPGK [SEQ ID NO: 7] |
| E31A_R33A | 361 | FSCSVMHEALHNHYTQKSLSLSPGK [SEQ ID NO: 2] |
| E315 R33E T51H | 361 | FSCSVMHEALHNHYTQKSLSLSPGK [SEQ ID NO: 6] |

2. Example 3

```
            CLUSTAL 2.1 multiple sequence alignment

CTLA4-Fc_WT       MHVAQPAVVLASSRGIASFVCEYASPGKATEVRVTVLRQADSQVTEVCAATYMMGNELTF   60
E31A_R33A         MHVAQPAVVLASSRGIASFVCEYASPGKATAVAVTVLRQADSQVTEVCAATYMMGNELTF   60
E31S              MHVAQPAVVLASSRGIASFVCEYASPGKATSVRVTVLRQADSQVTEVCAATYMMGNELTF   60
T51H              MHVAQPAVVLASSRGIASFVCEYASPGKATEVRVTVLRQADSQVTEVCAAHYMMGNELTF   60
E31S_R33E_T51H    MHVAQPAVVLASSRGIASFVCEYASPGKATSVEVTVLRQADSQVTEVCAAHYMMGNELTF   60
                  *****************************  * ****************** ********

CTLA4-Fc_WT       LDDSICTGTSSGNQVNLTIQGLRAMDTGLYICKVELMYPPPYYLGIGNGTQTYVIDPEPC  120
E31A_R33A         LDDSICTGTSSGNQVNLTIQGLRAMDTGLYICKVELMYPPPYYLGIGNGTQTYVIDPEPC  120
E31S              LDDSICTGTSSGNQVNLTIQGLRAMDTGLYICKVELMYPPPYYLGIGNGTQTYVIDPEPC  120
T51H              LDDSICTGTSSGNQVNLTIQGLRAMDTGLYICKVELMYPPPYYLGIGNGTQTYVIDPEPC  120
E31S_R33E_T51H    LDDSICTGTSSGNQVNLTIQGLRAMDTGLYICKVELMYPPPYYLGIGNGTQTYVIDPEPC  120
                  ************************************************************

CTLA4-Fc_WT       PDSDGSRSGGTSGGGSVPLSLYSGSTSGSGKSSEGSGQASTHTCPPCPAPELLGGPSVFL  180
E31A_R33A         PDSDGSRSGGTSGGGSVPLSLYSGSTSGSGKSSEGSGQASTHTCPPCPAPELLGGPSVFL  180
E31S              PDSDGSRSGGTSGGGSVPLSLYSGSTSGSGKSSEGSGQASTHTCPPCPAPELLGGPSVFL  180
T51H              PDSDGSRSGGTSGGGSVPLSLYSGSTSGSGKSSEGSGQASTHTCPPCPAPELLGGPSVFL  180
E31S_R33E_T51H    PDSDGSRSGGTSGGGSVPLSLYSGSTSGSGKSSEGSGQASTHTCPPCPAPELLGGPSVFL  180
                  ************************************************************

CTLA4-Fc_WT       FPPKPKDTLMISRTPEVTCVVVDVSHEDPEVKFNWYVDGVEVHNAKTKPREEQYNSTYRV  240
E31A_R33A         FPPKPKDTLMISRTPEVTCVVVDVSHEDPEVKFNWYVDGVEVHNAKTKPREEQYNSTYRV  240
E31S              FPPKPKDTLMISRTPEVTCVVVDVSHEDPEVKFNWYVDGVEVHNAKTKPREEQYNSTYRV  240
T51H              FPPKPKDTLMISRTPEVTCVVVDVSHEDPEVKFNWYVDGVEVHNAKTKPREEQYNSTYRV  240
E31S_R33E_T51H    FPPKPKDTLMISRTPEVTCVVVDVSHEDPEVKFNWYVDGVEVHNAKTKPREEQYNSTYRV  240
                  ************************************************************

CTLA4-Fc_WT       VSVLTVLHQDWLNGKEYKCKVSNKALPAPIEKTISKAKGQPREPQVYTLPPSRDELTKNQ  300
E31A_R33A         VSVLTVLHQDWLNGKEYKCKVSNKALPAPIEKTISKAKGQPREPQVYTLPPSRDELTKNQ  300
E31S              VSVLTVLHQDWLNGKEYKCKVSNKALPAPIEKTISKAKGQPREPQVYTLPPSRDELTKNQ  300
T51H              VSVLTVLHQDWLNGKEYKCKVSNKALPAPIEKTISKAKGQPREPQVYTLPPSRDELTKNQ  300
E31S_R33E_T51H    VSVLTVLHQDWLNGKEYKCKVSNKALPAPIEKTISKAKGQPREPQVYTLPPSRDELTKNQ  300
                  ************************************************************

CTLA4-Fc_WT       VSLTCLVKGFYPSDIAVEWESNGQPENNYKTTPPVLDSDGSFFLYSKLTVDKSRWQQGNV  360
E31A_R33A         VSLTCLVKGFYPSDIAVEWESNGQPENNYKTTPPVLDSDGSFFLYSKLTVDKSRWQQGNV  360
E31S              VSLTCLVKGFYPSDIAVEWESNGQPENNYKTTPPVLDSDGSFFLYSKLTVDKSRWQQGNV  360
T51H              VSLTCLVKGFYPSDIAVEWESNGQPENNYKTTPPVLDSDGSFFLYSKLTVDKSRWQQGNV  360
E31S_R33E_T51H    VSLTCLVKGFYPSDIAVEWESNGQPENNYKTTPPVLDSDGSFFLYSKLTVDKSRWQQGNV  360
                  ************************************************************

CTLA4-Fc_WT       FSCSVMHEALHNHYTQKSLSLSPGK-  [SEQ ID NO: 1]                    385
E31A_R33A         FSCSVMHEALHNHYTQKSLSLSPGK-  [SEQ ID NO: 2]                    385
E31S              FSCSVMHEALHNHYTQKSLSLSPGK-  [SEQ ID NO: 3]                    385
T51H              FSCSVMHEALHNHYTQKSLSLSPGK-  [SEQ ID NO: 7]                    385
E31S_R33E_T51H    FSCSVMHEALHNHYTQKSLSLSPGK-  [SEQ ID NO: 6]                    385
                  *************************
```

4. Example 4

Wildtype trastuzumab mask No. 1. Human Her2 (underline); The Fc human IgG1 (bold); Cleavage site (e.g MMP9 site) (bold underline):

(SEQ ID NO: 11)
<u>CSQFLRGQECVEECRVLQGLPREYVNARHCLPCHPECQPQNGSVTCFGP</u>

<u>EADQCVACAHYKDPPFCVARCPSGVKPDLSYMPIWKFPDEEGACQPCPI</u>

<u>NGSRSGGTSGGGS</u><b><u>VPLSLYS</u></b>GSTSGSGKSSEGSGQASTHTCPPCPAPEL

LGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHE

ALHNHYTQKSLSLSPGK.

Wildtype trastuzumab mask No. 2. Human Her2 (underline); the Fc human IgG1 (bold); Cleavage site (e.g MMP9 site) (bold underline):

(SEQ ID NO: 12)
<u>CSQFLRGQECVEECRVLQGLPREYVNARHCLPCHPECQPQNGSVTCFGP</u>

<u>EADQCVACAHYKDPPFCVARCPSGVKPDLSYMPIWKFPDEEGACQPCPI</u>

<u>NGSRSGGTSGGGS</u><b><u>VPGSGSS</u></b>GSTSGSGKSSEGSGQASTHTCPPCPAPEL

LGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPI

-continued

EKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHE

ALHNHYTQKSLSLSPGK.

Mutated EGFR domain III heavy chain mask (N-terminus of the heavy chain of Cetuximab). The point mutations prevent "aggregation" (i.e., keeping the mask from binding to cetuximab itself) EGRF domain III (underline); mutations (bold); cleavage site (MMP9 site) (bold underline):

(SEQ ID NO: 13)
MRPSGTAGAALLALLAALCPASRARKVCNGIGIGEFKDSLSINATNIKH

FKNCTSISGDLHILPVAFRGDSFTHTPPLDPQELDILKTVKEITGFLLI

AAWPENRTDLHAFENLEIIRGRTNMDGQFSLAVVSLNITSLGLRSLKEI

SDGDVIISGNKNLCYANTINWKKLFGTSGQKTKIISNRGENSCKATGQV

CHALCSPEGCWGPEPKDCVSCRNVSRGRECSRGGGSGGGSGGGSVPLSL

YSGSTSGSGKSSEGSGSGAQVOLKQSGPGLVQPSQSLSITCTVSGFSLT

NYGVHWVRQSPGKGLEWLGVIWSGGNTDYNTPFTSRLSINKDNSKSQVF

FKMNSLQSNDTAIYYCARALTYYDYEFAYWGQGTLVTVSAASTKGPSVF

PLAPSSKSTSGGTAALGCLVKDYFPEPVTVSWNSGALTSGVHTFPAVLQ

SSGLYSLSSVVTVPSSSLGTQTYICNVNHKPSNTKVDKRVEPKSCDKTH

TCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKG

FYPSDIAVEWESNGQPENNYKTTPPVLDSDGSFFLYSKLTVDKSRWQQG

NVFSCSVMHEALHNHYTQKSLSLSPGK.

Mutated EGFR domain III light chain mask:

(SEQ ID NO: 14)
MRPSGTAGAALLALLAALCPASRADILLTQSPVILSVSPGERVSFS

CRASQSIGTNIHWYQQRTNGSPRLLIKYASESISGIPSRFSGSGSG

TDFTLSINSVESEDIADYYCQQNNNWPTTFGAGTKLELKRTVAAPS

VFIFPPSDEQLKSGTASVVCLLNNFYPREAKVQWKVDNALQSGNSQ

ESVTEQDSKDSTYSLSSTLTLSKADYEKHKVYACEVTHQGLSSPVT

KSFNRGA.

The modified lipocalin2 (mLcn2):

(SEQ ID NO: 15)
Q D S T S D L I P A P P L S K V P L

Q Q N F Q D N Q F H G K W Y V V G L A G

N R I L R D D Q H P M N M Y A T I Y E L

K E D K S Y N V T S V I S S H K K C E Y

T I A T F V P G S Q P G E F T L G N I K

S Y G D K T S Y L V R V V S T D Y N Q Y

A V V F F K L A E D N A E F F A I T I Y

G R T K E L A S E L K E N F I R F S K S

L G L P E N H I V F P V P I D Q C I D G

5. Example 5

Figure 5:
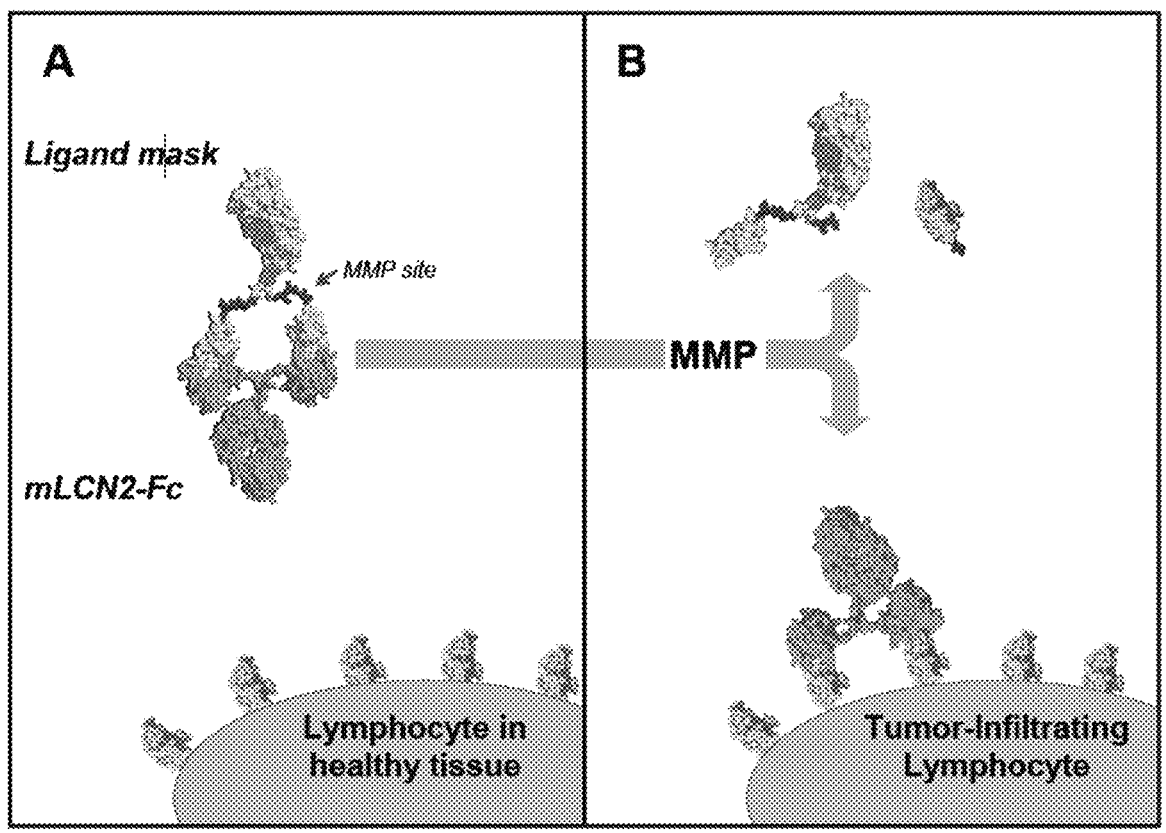
FIG. 5: Representation of non-covalent CTLA4-Fc mask system. CTLA4 antagonist prodrug is systemically administered as a 1:1 mLCN2-Fc:CTLA4-Fc complex. A Non-covalent CTLA4-Fc MMP mask inhibits mLCN2-Fc from binding endogenous CTLA4 in normal, healthy tissue. B Once the prodrug enters the tumor microenvironment, local protease overexpression (shown here as MMP) activates the prodrug by cleaving one or both MMP sites on the ligand mask. Avidity and, therefore, affinity are lost between the mask and mLCN2-Fc, permitting dissociation of mask and enabling mLCN2-Fc to bind to CTLA4 within the tumor.

The bivalent mask consists of two extracellular domains of human CTLA4 fused via protease substrate to an IgG1 (FIG. 5). Briefly, the masked mAb prodrug incorporated a non-covalent mask to occlude the antigen-binding region (CDR) of antibodies. In this design, the non-covalent mask consisted of recombinant antigen fragments fused to human IgG1 through a flexible peptide linker containing tumor-associated protease substrate. The bivalent-bivalent avidity of the mAb:mask interaction attains very high affinities. Expressed mathematically:

$$AG_{total} = AG_1 + AG_2 - AG_{linker}$$

where $AG_{total}$ is the change in free energy of the total system, $AG_1$ and $AG_2$ are the free energies of each CDR: antigen interaction, and $AG_{linker}$ is the free energy due to linking each antigen (e.g., entropy loss, conflicts in geometry, etc.). Since $AG = -RT \ln(K)$, $$-RT \ln(K_{total}) = -RT \ln(K_1) - RT \ln(K_2) + RT \ln(K_{linker})$$

If $AG_{linker}$ is negligible (i.e., 0), the binding constants are multiplicative:

$$-RT \ln(K_{total}) = -RT \ln(K_1) - RT \ln(K_2)$$

$$-RT \ln(K_{total}) = -RT[\ln(K_1) + \ln(K_2)]$$

$$-RT \ln(K_{total}) = -RT[\ln(K_1 \cdot K_2)]$$

$$K_{total} = K_1 \cdot K_2$$

Assuming proper geometry and minimal entropy loss for the mLCN2-Fc prodrug construct, the affinity between bivalent molecules mLCN2-Fc and CTLA4-Fc mask is $5.5 \times 10^{-9} M \cdot 5.5 \times 10^{-9} M = 3.0 \times 10^{-17} M$ (see Chapter 2 for $K_D$ determination of monomeric mLCN2:CTLA4 interaction). If the protease substrate on the mask linker is hydrolized, avidity is lost and the affinity returns to 5.5 nM, thereby permitting dissociation of the mask and subsequent activation of mLCN2-Fc.

However, the $k_d$ between monovalent mLCN2 and CTLA4 was observed to be $2 \times 10^{-4}$ s$^{-1}$. Using the equation for dissociation half-life time, $t_{1/2} = \ln(2)/k_d$, we find the dissociative half-life time of monomeric CTLA4 and mLCN2 to be 3465 s (~58 min). Mutations were introduced into the CTLA4 mask at the binding interface to hasten dissociation upon activation. Once dissociated, the CTLA4 mask could potentially bind endogenous ligands CD80 and CD86 and function as an immunosuppressant (e.g., abatacept [2]). Using crystal structures and published biochemical reports, we investigated mutations on the CTLA4 mask to abrogate binding to CD80/CD86 as well as address the dissociation obstacle [3, 4].

Described herein is the engineering of a non-covalent mask for mLCN2-Fc for intratumoral delivery of a CTLA4 antagonist. The mask consists of human CTLA4 extracellular domain fused via an MMP9 substrate to IgG1, conferring high affinity through avidity to the system. Cell-staining and functional assays showed intact masked prodrug was incapable of binding CTLA4. Ligand mask, both apo and complexed with mLCN2-Fc, was cleaved by MMP9 in vitro. Upon activation by MMP9—a protease overexpressed in many human tumors—avidity is lost and the dissociation of mask would permit mLCN2-Fc binding to CTLA4 on tumor-infiltration lymphocytes.

Materials and Methods

Molecular Biology. Human CD86 extracellular domain (UniProt entry: P42081) was cloned to the N-terminus of IgG1 (UniProt entry: P01857) and inserted into the insect cell expression vector pVL1393 with a secretion signal gp67 at the N-terminus [5, 6]. DNA sequencing confirmed successful subcloning (City of Hope DNA Sequencing Core, Duarte, Calif.).

Protein expression and purification of Fc constructs. Bivalent constructs containing human Fc (IgG1) were cloned in the pVL1393 vector and transfected into Sf9 insect cells with BestBac 2.0 Baculovirus Cotransfection kit (Expression System). High titer virus was generated and used to infect Tni cells at an MOI of 3 for protein production. Cells were harvested 48 h post-infection, centrifuged, and supernatant was applied to Protein A resin (GenScript). Column was washed extensively with PBS, and protein was eluted with 0.1 M glycine pH 3.0 and immediately pH neutralized with 1 M Tris-HCl pH 8.0. Concentrated eluate was applied to HiLoad 26/60 Superdex 200 column (GE Healthcare) in PBS and peak fractions were concentrated, flash frozen, and stored at −80° C.

Surface Plasmon Resonance (SPR). SPR experiments were performed on a GE Biacore T100 instrument at 25° C. Ligands were amine coupled to CMS chips at 300 $R_{max}$. Blank lanes were used as baseline control. Analyte titrations were prepared as serial dilutions in HBS-EP+ running buffer (10 mM Hepes pH 7.4, 150 mM NaCl, 3 mM EDTA, 0.05% v/v P20). Increasing concentrations of analytes were flowed over blank and ligand lanes at 50 µL/min. Regeneration buffer (1 M NaCl, 10 mM glycine pH 2.6) was flowed at 90 µL/min for 10 s. Data analyses were performed using Biacore T100 Evaluation Software, version 1.1.1 (GE Healthcare). Response reported as the difference between blank and peptide lanes.

In vitro MMP9 cleavage assays. Time-course cleavage assay: CTLA4-Fc MMP9 and Mxx9 proteins were complexed with mLCN2-Fc and purified by gel-filtration. Samples were dialyzed against cleavage buffer (5 mM CaCl2; 0.02% NP-40, 50 mM Tris pH 7.4, 150 mM NaCl). 8 µg of apo or complex samples were treated with 1 µg recombinant human MMP9 (ProSpecBio) or equivalent volume buffer and incubated at 37° C. At selected times, samples were mixed with 2×SDS running buffer in the presence or absence of DTT and loaded on a 5% stacking/12% resolving SDS-PAGE. Gel electrophoresis was performed at 150 V for 45 min and gel was stained with Coomassie Brilliant Blue. Temperature-dependence cleavage assay: 125 µg of CTLA4-Fc WP9 was incubated 12 hours at 4°, 25°, or 37° C. in the presence or absence of 0.2 µg recombinant human MMP-9. Samples were run in non-reducing conditions on a 8-25% gradient PhastGel (GE) and stained with Coomassie Brilliant Blue.

Flow cytometry. Murine cells: Splenocytes were isolated from C57BL/6 mice; 75E6 cells per well were plated in a 6-well plate in IMDM with 10% FBS plus antibiotic/antimycotic. For primed samples, T-cells were co-cultured with 20% sterile-filtered tumor supernatant (TSN) from C4 murine melanoma cell culture for 24 h. Following incubation, denoted samples received 20 µg CTLA4-Fc MMP9 in PBS immediately chased with 20 jig Alexa Fluor 647-conjugated mLCN2-Fc in PBS. Sterile PBS immediately chased with 20 µg 647mLCN2-Fc in PBS was added to remaining treatment wells. Cells were incubated one hour at 37° C., protected from light. Cells were collected and spun 1500 RPM 4 C for 5 min. Supernatant was aspirated and cells were resuspended in 450 µL staining buffer (SB, 2% BSA in PBS). Cells were treated with 1:100 dilution of α-FcγR (Robosep) for five minutes. For each experimental group, 200 µL of cells were distributed to 2 flow cytometry tubes. A 1:50 dilution of either α-muCD4-FITC or α-muCD8-FITC (BD Biosciences) was added to sample tubes, subsequently covered and incubated on ice for 30 min protected from light. Cells were washed with SB and resuspended in 300 µL DAPI solution. Samples were analyzed on BD Accuri C6 system (BD Biosciences). Data were analyzed using FlowJo software (Tree Star).

Human Cells:

Human Daudi cells (ATCC, CCL-213) were maintained in RPMI-1649 medium plus 10% FBS. For flow cytometric experiments, cells were washed twice with SB. 2E6 cells per sample were stained with indicated amounts of Alexa Fluor 647-conjugated CTLA4-Fc for 30 min in the dark at room temperature. Cells were washed twice and resuspended in 1:200 DAPI in staining buffer. Flow cytometry was performed at the City of Hope FACS facility with a CyAn ADP 9 (Beckman Coulter) and the data were analyzed using FlowJo software (Tree Star). Analytical size exclusion chromatography (SEC). Purified samples were mixed 1:1 molar ratio, prepared at 6 µM in PBS and incubated for 1 h at 4° C. SEC was performed at 4° C. using a Superdex 200 10/300 GL (GE Healthcare) and monitored at 230 nm. ELISpot IFN-γ ELISpot was performed according to manufacturer's protocol (eBioscience). Briefly, splenocytes were harvested from OT-I C57BL/6-Tg(TcraTcrb)1100Mjb/Crl transgenic mice (Charles River). In vitro activation: Single-cells suspensions of splenocytes were co-cultured with phytohaemagglutinin (PHA) or irradiated B16-TAC cells (B16 murine melanoma cells expressing TAC antigen [7]) in the presence or absence of sterile mLCN2-Fc or pre-complexed mLCN2-Fc:CTLA4-Fc for five days. In vivo activation: OT-I mice were injected at day 0 and 7 with adenovirus encoding TAC antigen as previously described [8]. At day 14 spleens were harvested and mixed with irradiated B16-TAC cells. Samples from all activation methods were incubated on anti-IFN-γ antibody-coated ELISpot plate for 24 h. IFN-γ production was measured by ELISpot plate reader (Cellular Technology, Ltd.).

Production and Purification of CTLA4-Fc MMP9 Mask

A protease-cleavable, non-covalent mask for mLCN2-Fc was created by modifying the recombinant CTLA4-Fc protein. Specifically, a sequence in the linker between CTLA4 and Fc was mutated to VPLSLYS, a hydrolyzable MMP9 substrate [9]. This protein mask [CTLA4-Fc MMP9] was biosynthesized by insect cells at a yield of ~20 mg/L growth.

As demonstrated by SEC and SPR, mLCN2-Fc bound to WT CTLA4-Fc (henceforth called "CTLA4-Fc Mxx9," i.e., non-cleavable mask) with high affinity. This trend was also seen with MMP9-cleavable CTLA4-Fc MMP9. However, when mLCN2-Fc was mixed at equimolar ratio with CTLA4-Fc MMP9, multiple peaks were seen at a lower elution volume by analytical SEC analysis (FIG. 6). mLCN2-Fc was mixed with CTLA4-Fc at concentrations of 20 µM per protein ("fast mixing," FIG. 6 panel A) and three major peaks of higher elution volume were observed: Peak 1 (volumetric range from 7.6-8.6 mL) accounted for ~25% of the area under the curve (AUC); Peak 2 (from 8.6-9.6 mL)

was 38% of AUC; and Peak 3 (from 10.1-11.1 mL) was 37% of AUC. When lower initial concentrations of mLCN2-Fc and CTLA4-Fc (40 nM each protein) were mixed and given time to come to equilibrium prior to SEC analysis, three peaks of higher elution volume were also seen ("slow mixing," FIG. 6 panel A purple trace). Peak 3 accounted for ~70% of the total AUC, whereas Peaks 1 and 2 combined for the remaining 30%.

Figure 6:
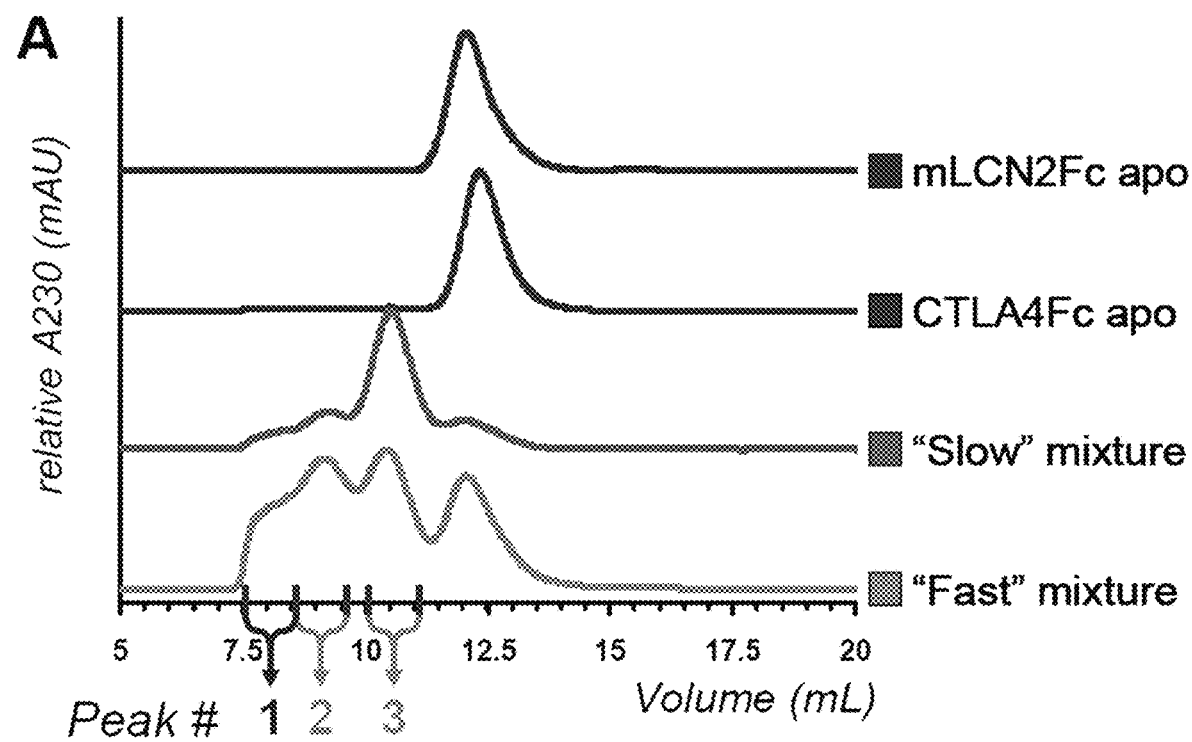
FIG. 6: Binding stoichiometry of mLCN2-Fc and CTLA4-Fc MMP9 is dependent on initial protein concentrations. A High initial protein concentrations ("Fast" mixture) resulted in multiple high-order binding mixtures, as demonstrated by SEC. Most protein was bound 1:1 when lower initial concentrations were used ("Slow" mixture). Peaks 1, 2, and 3 of initial B "Fast" mixture and C "Slow" mixture were isolated and reanalyzed by SEC.
Figure 6:
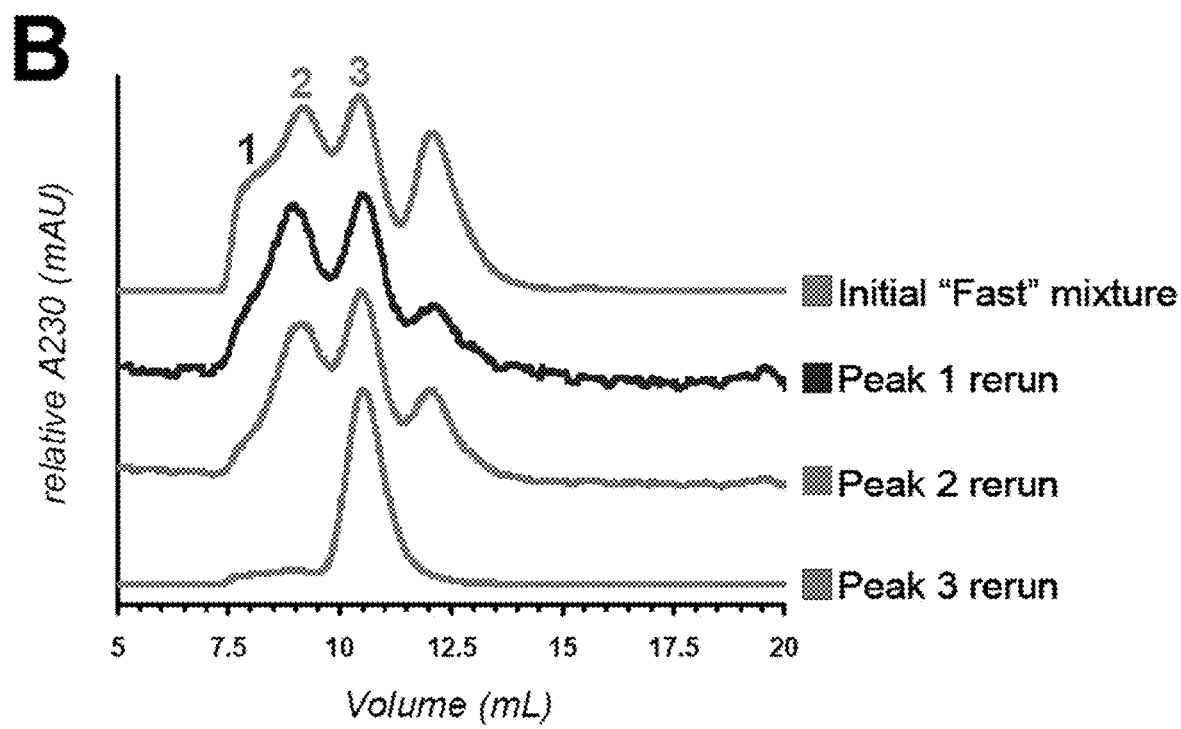
Figure 6:
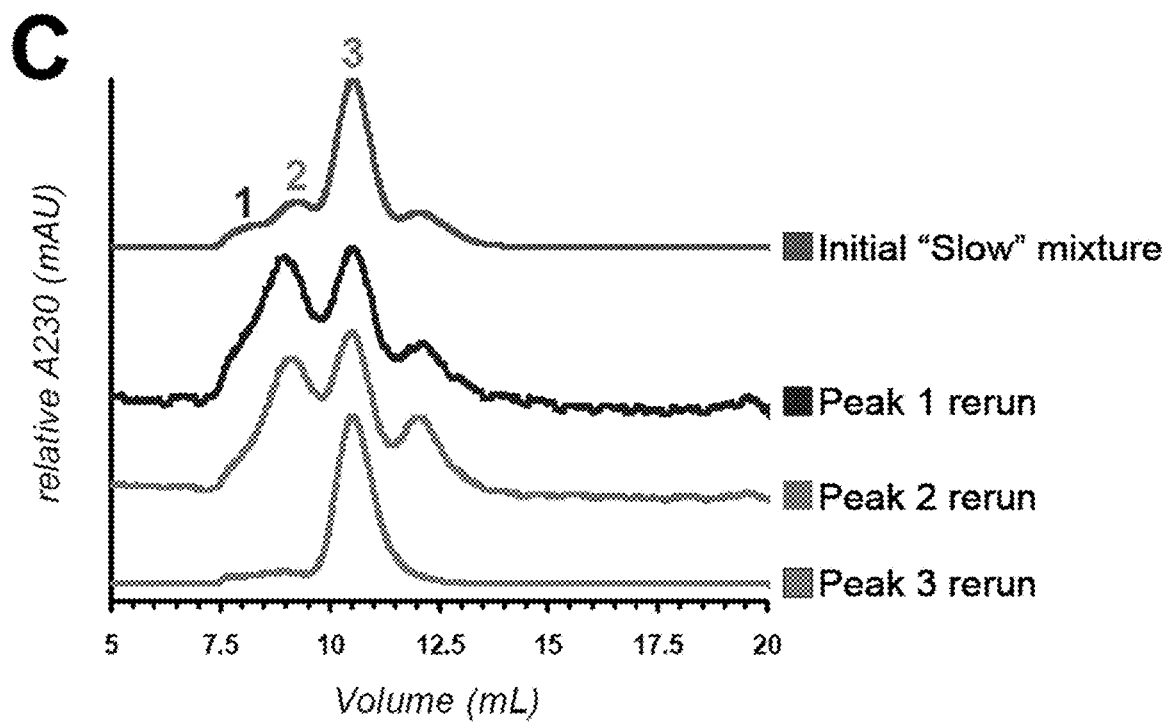

The three peaks from each SEC were isolated and separately reanalyzed by SEC. Peak 1 from the both reactions eluted at three separate peaks of higher molecular weight (FIG. 6 panels B and C). Peak 2 from both initial reactions eluted as two major peaks (orange). Peak 3, which contained 1:1 complexes of mLCN2-Fc and CTLA4-Fc, eluted as one major peak at 10.5 mL (grey).

In Vitro MMP9 Cleavage of Non-Covalent Mask

Recombinant CTLA4-Fc MMP9 mask contains MMP9 hydrolysis substrate, VPLSLYS, between CTLA4 and Fc domains. To assess MMP9 cleavage, we also created a mask that was incapable of MMP9 cleavage (CTLA4-Fc Mxx9). Both masks were capable of binding mLCN2-Fc, qualitatively shown by SEC. A series of in vitro experiments tested the cleavage of CTLA4-Fc MMP9 by recombinant human MMP9.

Incubating CTLA4-Fc MMP9 with recombinant MMP9 at 37° C. for 9 h resulted in two major protein bands, as resolved by SDS-PAGE (FIG. 3). Addition of MMP9 had no effect on CTLA4-Fc Mxx9 bands. Next, MMP9 cleavage reactions were tested at different temperatures to assess the temperature dependence of CTLA4-Fc MMP9 cleavage. Reactions at 25° C. and 37° C. had similar band intensities of cleavage products, whereas a stronger band at the molecular weight of intact mask was seen in the reaction at 4° C. (FIG. 3). A time-course experiment analyzed the rate of in vitro CTLA4-Fc MMP9 cleavage at 37° C. (FIG. 3). At 2 h the intensity of the full-length band was ~50% of the 0 h timepoint, and at 8 h most of the band was gone. Finally the cleavage of pre-complexed mLCN2-Fc:CTLA4-Fc MMP9 was assessed (FIG. 3). Complexed CTLA4-Fc MMP9 was cleaved at a rate similar to that of apo CTLA4-Fc MMP9 (FIG. 3).

CTLA4-Fc MMP9 Mask Inhibits mLCN2-Fc Binding to T-Cells

Figure 7:
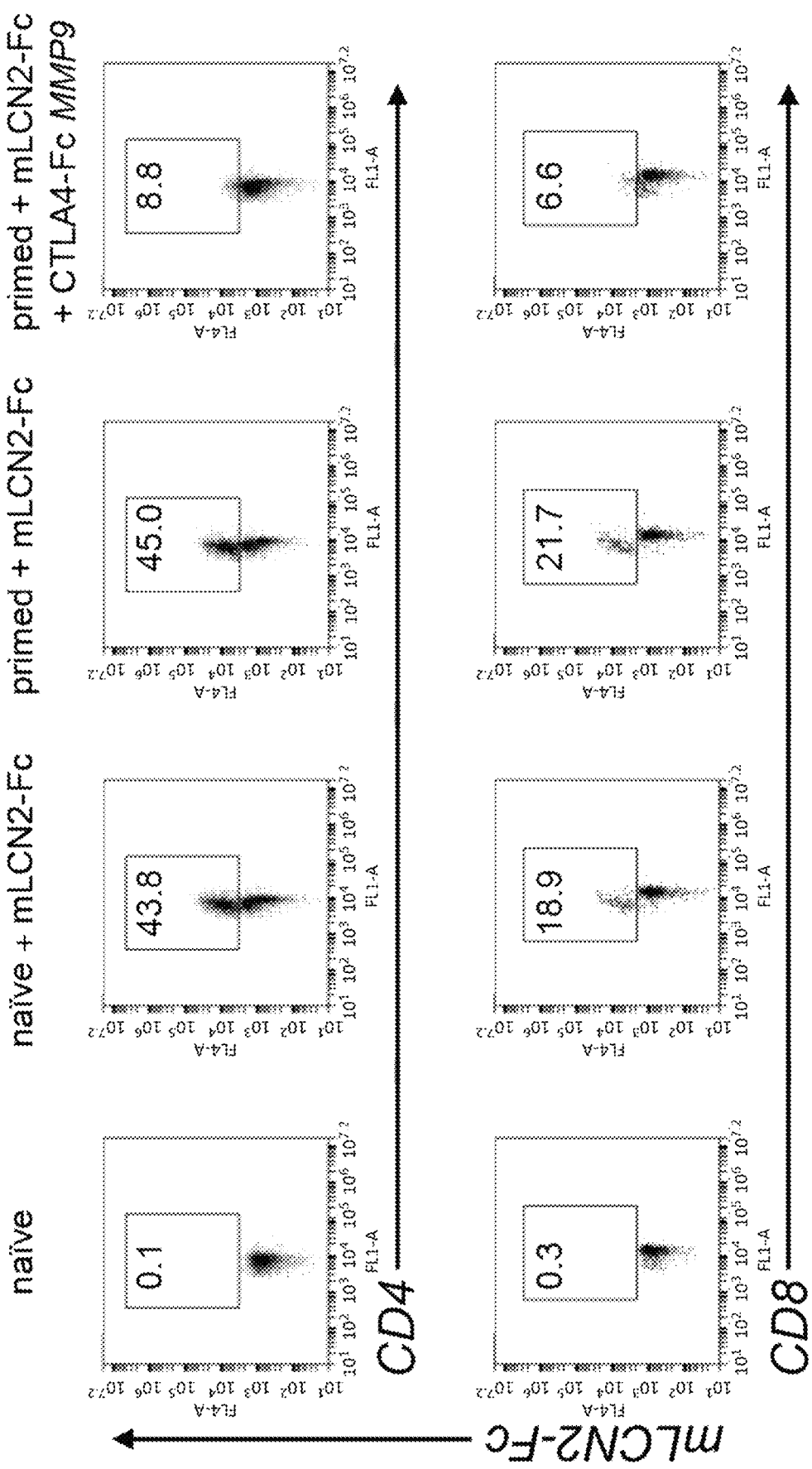
FIG. 7: CTLA4-Fc MMP9 inhibits the engagement of mLCN2-Fc and murine T-cells. Murine splenocytes were isolated and cultured in the absence or presence of tumor supernatant (naïve or primed, respectively). After 24 h, 20 µg CTLA4-Fc MMP9 was added in the competition condition. Subsequently 20 µg 647'mLCN2-Fc was added to all treatment wells. Cells were analyzed by flow cytometry for CD4$^+$ (top row), CD8$^+$ (bottom), and 647'mLCN2-Fc staining.

Binding of CTLA4 on live cells was tested in a competition assay by staining murine T-cells with 647'mLCN2-Fc or CTLA4-Fc MMP9 plus 647'mLCN2-Fc. Fluorescently labeled 647'mLCN2-Fc was added to naïve and primed cells in the presence or absence of CTLA4-Fc MMP9. CD4+ and CD8+ cells were subsequently identified by flow cytometry and analyzed for mLCN2-Fc staining (FIG. 7). A 5-fold and 3-fold reduction of mLCN2-Fc staining in CD4+ and CD8+ cells, respectively, was seen with the addition of CTLA4-Fc. In cells treated with mLCN2-Fc only, we observed a slight increase in binding between the naive and primed T-cell samples of both CD4+ (2.7% increase) and CD8+ (14.8%) cells.

Figure 8:
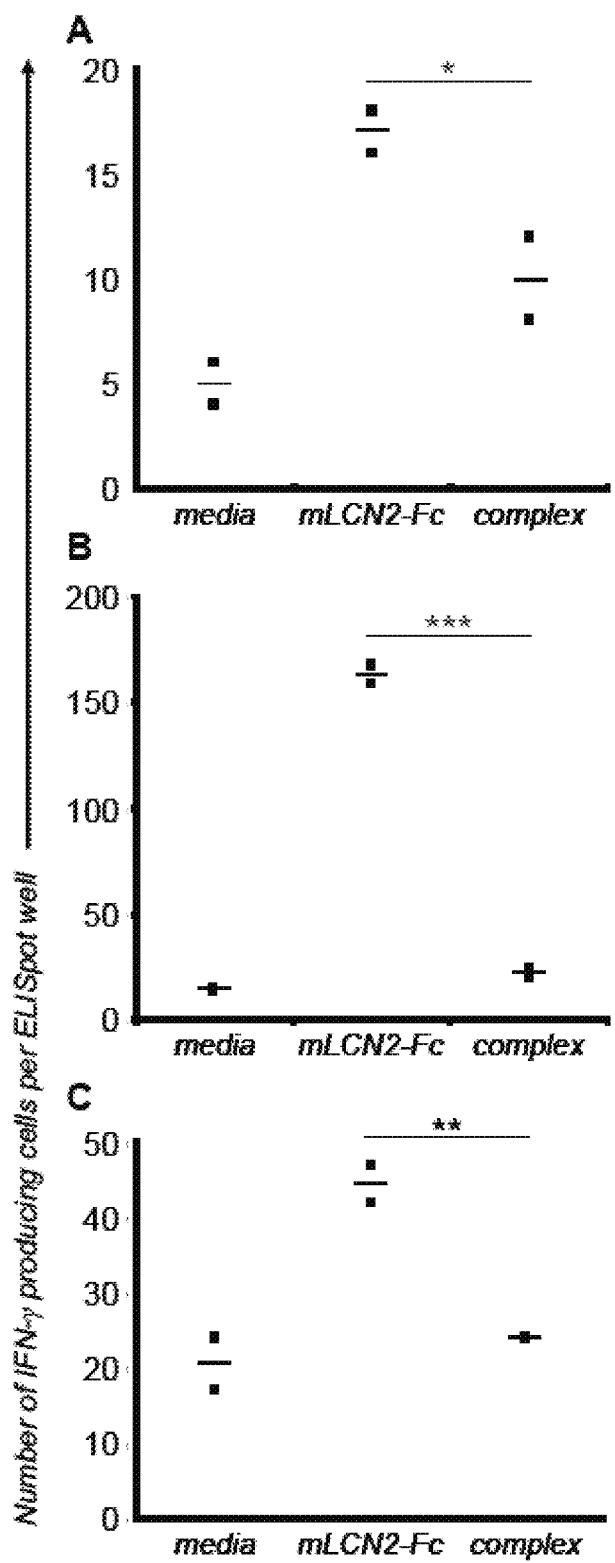
FIG. 8: CTLA4-Fc MMP9 inhibits mLCN2-Fc-mediated stimulation of IFN-γ production by T-cells in vitro. Cytokine IFN-γ production in murine splenocytes co-cultured with mLCN2-Fc or mLCN2-Fc:CTLA4-Fc (complex) was analyzed by ELISpot. Splenocytes from OT-I mice were activated by A phytohaemagglutinin (PHA), B TAC-expressing B16 melanoma cells in vitro, or C in vivo vaccination with adenovirus encoding TAC antigen. Black squares represent the number of IFN-γ producing cells per well. Black bisecting bar is the average per condition. Statistics provided from one-tail t-test. * p<0.05;  p<0.01; * p<0.001.

Functional assay by cytokine ELISpot analysis tested the immune stimulation of masked mLCN2-Fc. Splenocytes from OT-I transgenic mice, activated with PHA or irradiated B16-TAC cells in vitro or with adenovirus encoding TAC antigen in vivo, were incubated with apo mLCN2-Fc or mLCN2-Fc:CTLA4-Fc MMP9 complex for five days. Cells were applied to an ELISpot to quantify IFN-γ production (i.e., T-cell stimulation). In all tested settings of T-cell activation, co-incubation with mLCN2-Fc had significantly higher stimulation of IFN-γ production compared to co-incubation with mLCN2-Fc:CTLA4-Fc complex (FIG. 8). The largest differential in IFN-γ production was seen in the in vitro activation by B16-TAC cells experimental groups (FIG. 8 panel B). In this activation setting, we observed 163±6 IFN-γ producing cells in samples treated with apo mLCN2-Fc, whereas samples treated with mLCN2-Fc:CTLA4-Fc generated 21±3 IFN-γ producing cells. For comparison, cells treated with only media yielded 15±7 IFN-γ producing cells.

Non-Covalent Mask Binds Human CD86 In Vitro

Figure 9:
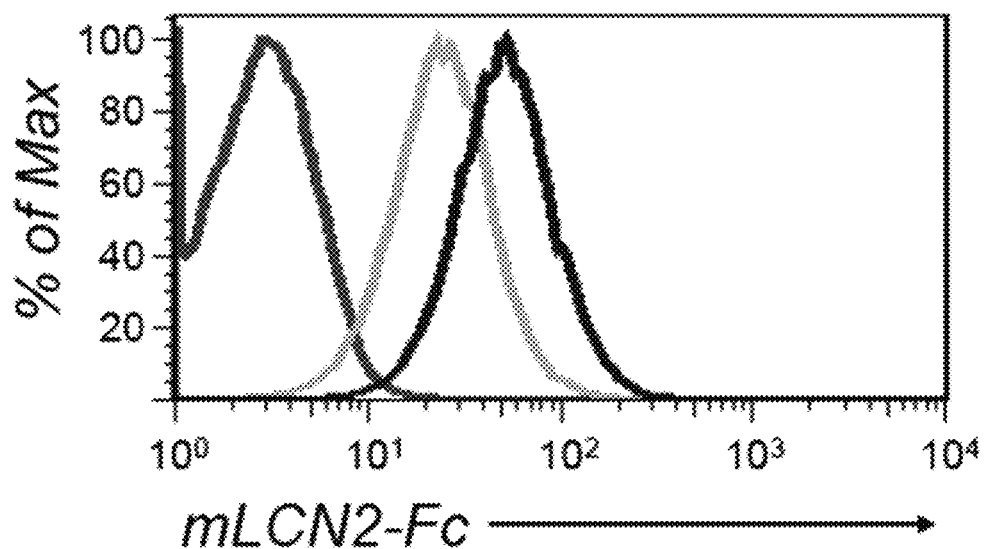
FIG. 9: CTLA4-Fc MMP9 binds CD80 and CD86 expressed on live cells. Human lymphoblast Daudi cells, which naturally express CD80 and CD86, were incubated with 647"CTLA4-Fc MMP9. CTLA4-Fc binding was assessed by flow cytometry.

The binding of CTLA4-Fc mask to endogenous ligand of CTLA4, CD86, was analyzed by flow cytometry and SEC. Fluorescent dye 647 was conjugated to CTLA4-Fc WP9 and tested by flow cytometry for binding to Daudi cells, a human lymphoma cell line that expresses CD80 and CD86. We observed 647"CTLA4-Fc stained Daudi cells in a concentration-dependent manner (FIG. 9). We also produced and purified recombinant bivalent CD86-Fc (human CD86 extracellular domain fused to human IgG1). When mixed 1:1 with CTLA4-Fc and analyzed by SEC, the elution peak signifies formation of a higher molecular weight complex (FIG. 10).

Further Engineering of the CTLA4-Fc Mask

To reduce the affinity of CTLA4-Fc MMP9 mask for CD80/CD86, we analyzed the crystal structures of CTLA4 bound to these ligands and to mLCN2. Looking at the superposition of the three crystal structures, there is an overlapping region of CTLA4 that interacts with all three ligands. However, there are also several residues on CTLA4 that contact CD80 and CD86 uniquely (Glu31, Arg33, Thr51) and several residues that recognize only mLCN2 (Lys95, Glu97). We made point mutations at these residues on our CTLA4-Fc mask to reduce affinities for CD80 and CD86 as well as increase the $k_d$ between the mask and mLCN2.

Figure 10:
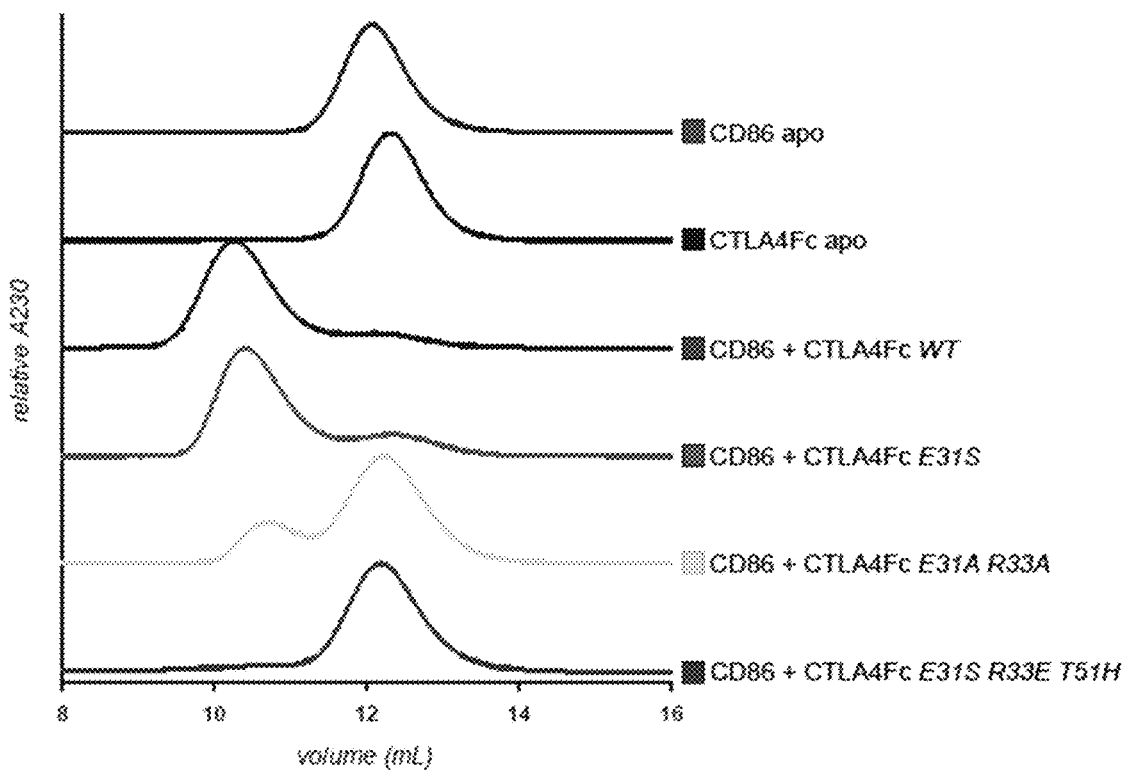
FIG. 10: SEC analysis of CD86-Fc interactions CTLA4-Fc mask variants. Equimolar solutions of recombinant human CD86-Fc and CTLA4-Fc variants were analyzed by analytical SEC. Absorbance at 230 nm is reported.

When analyzed by SEC, apo CTLA4-Fc variants eluted at 12.2 mL (FIG. 10). CTLA4-Fc variant E31S eluted at 10.4 mL when incubated with CD86-Fc, signifying binding to CD86-Fc. Two elution peaks were noted when E31A R33A was mixed with CD86-Fc, indicating heterogeneous mixture of bound and unbound protein. E31S R33E T51H showed no binding of CD86-Fc, as this sample eluted as one peak at 12.1 mL.

Figure 11:
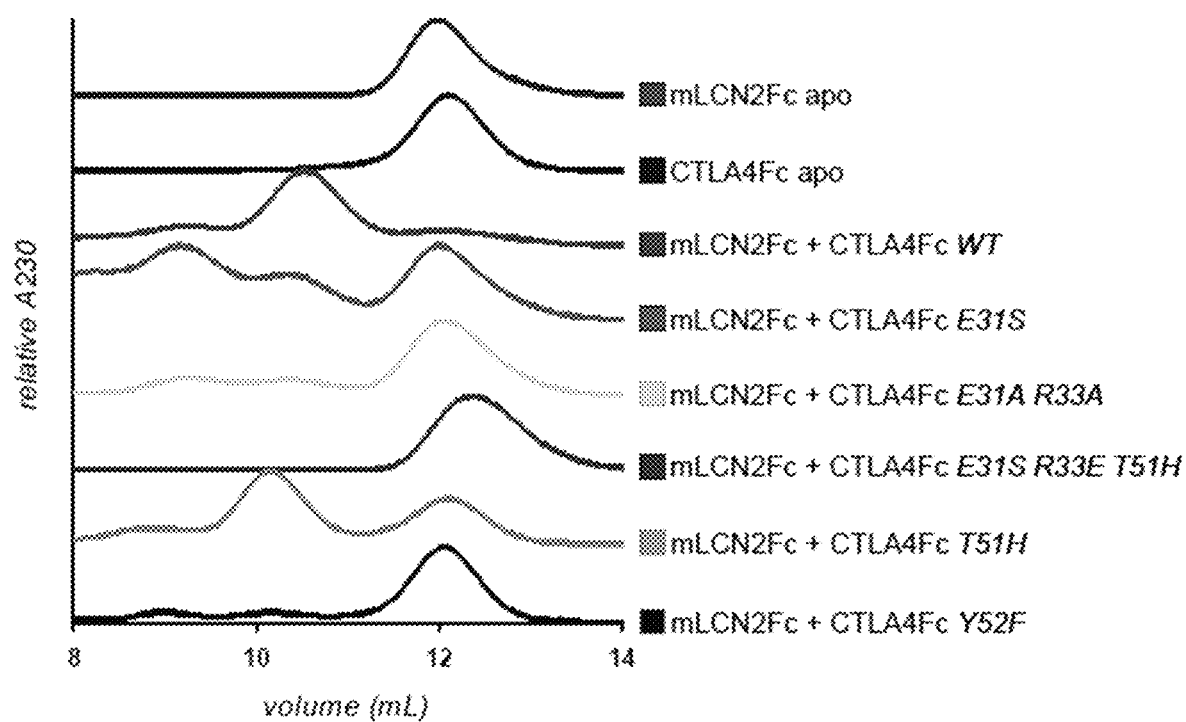
FIG. 11: SEC analysis of mLCN2-Fc interactions CTLA4-Fc mask variants. Equimolar solutions of mLCN2-Fc and CTLA4-Fc variants were analyzed by analytical SEC. Absorbance at 230 nm is reported.

SEC was also utilized to assess binding of CTLA4-Fc to mLCN2-Fc. E31S eluted as two peaks of higher molecular size with the addition of mLCN2-Fc (FIG. 11). A major elution peak from T51H mixture was observed at 10.2 mL. These two variants demonstrated substantial binding to mLCN2-Fc. Intermediate peaks of higher molecular sizes were seen for samples E31A R31A and Y52F, suggesting heterogeneous binding to mLCN2-Fc. E31S R33E T51H eluted at 12.2 mL, signifying no binding to mLCN2-Fc.

All CTLA4-Fc variants tested had lower affinity for mLCN2-Fc compared to CTLA4-Fc WT (Table 3). T51H had a $K_D$ of 9.07 nM and a $k_d$ of 2.20E-04 s$^{-1}$. Y52F had a $K_D$ of 6.14 nM and a $k_d$ of 2.15E-04 s$^{-1}$. E31A R33A had a $K_D$ of 100 nM and $k_d$ of 1.10E-03 s$^{-1}$. E31S R33E T51H had a $K_D$ of 5600 nM and a $k_d$ of 2.50E-02 s$^{-1}$.

TABLE 3

Kinetics of CTLA4-Fc mask variants, as measured by SPR. Binding kinetics of mLCN2 for each CTLA4-Fc variant was measured by SPR. Half-life time was calculated from equation: $t_{1/2} = \ln(2)/k_d$.

| CTLA4-Fc Variant | $k_a$ (M$^{-1}$s$^{-1}$) | $k_d$ (s$^{-1}$) | $K_D$ (M) | Calculated $t_{1/2}$ (s) |
|---|---|---|---|---|
| WT | 3.64E04 | 2.01E-04 | 5.52E-09 | 3466 |
| E31A R33A | 1.10E04 | 1.10E-03 | 1.00E-07 | 693 |

TABLE 3-continued

Kinetics of CTLA4-Fc mask variants, as measured by SPR.
Binding kinetics of mLCN2 for each CTLA4-Fc variant was measured
by SPR. Half-life time was calculated from equation: $t_{1/2} = \ln(2)/k_d$.

| CTLA4-Fc Variant | $k_a$ ($M^{-1}s^{-1}$) | $k_d$ ($s^{-1}$) | $K_D$ (M) | Calculated $t_{1/2}$ (s) |
|---|---|---|---|---|
| E31S R33E T51H | 4.43E03 | 2.50E−02 | 5.60E−06 | 28 |
| T51H | 2.42E04 | 2.20E−04 | 9.07E−09 | 3151 |
| Y52F | 3.51E04 | 2.15E−04 | 6.14E−09 | 3224 |

REFERENCES

1. Donaldson, J. M., et al., Design and development of masked therapeutic antibodies to limit off-target effects: application to anti-EGFR antibodies. Cancer Biol Ther, 2009. 8(22): p. 2147-52.
2. Maxwell, L. J. and J. A. Singh, Abatacept for rheumatoid arthritis: a Cochrane systematic review. J Rheumatol. 37(2): p. 234-45.
3. Morton, P. A., et al., Differential effects of CTLA-4 substitutions on the binding of human CD80 (B7-1) and CD86 (B7-2). J Immunol, 1996. 156(3): p. 1047-54.
4. Xu, Z., et al., Affinity and cross-reactivity engineering of CTLA4-Ig to modulate T cell costimulation. J Immunol. 189(9): p. 4470-7.
5. Charles, I. G., et al., Cloning and expression of a rat neuronal nitric oxide synthase coding sequence in a baculovirus/insect cell system. Biochem Biophys Res Commun, 1993. 196(3): p. 1481-9.
6. Au, L. C., et al., Secretory production of bioactive recombinant human granulocyte-macrophage colony-stimulating factor by a baculovirus expression system. J Biotechnol, 1996. 51(2): p. 107-13.
7. Waldman, S. A., Annual Progress Report: 2009 Nonformula Grant on Cancer Vaccines. 2011, Thomas Jefferson University: Philadelphia, Pa. p. 1-9.
8. Igoucheva, O., et al., Immunotargeting and eradication of orthotopic melanoma using a chemokine-enhanced DNA vaccine. Gene Ther, 2013. 20(9): p. 939-48.
9. Turk, B. E., et al., Determination of protease cleavage site motifs using mixture-based oriented peptide libraries. Nat Biotechnol, 2001. 19(7): p. 661-7.

VII. EMBODIMENTS

Embodiment 1

A recombinant masking protein comprising two identical masking protein domains, each of said masking protein domains comprising: (i) a masking dimerizing domain; (ii) a ligand-masking binding domain; and (iii) a cleavable masking linker connecting said ligand-masking binding domain to said masking dimerizing domain, wherein said masking protein domains are bound together.

Embodiment 2

The recombinant masking protein of embodiment 1, wherein said masking dimerizing domain is an Fc protein domain.

Embodiment 3

The recombinant masking protein of embodiment 2, wherein said Fc protein domain is an IgG$_1$ Fc protein.

Embodiment 4

The recombinant masking protein of any one of embodiments 1-3, wherein said ligand-masking binding domain is a small molecule or a cellular protein domain.

Embodiment 5

The recombinant masking protein of embodiment 4, wherein said cellular protein domain is a cellular growth factor domain, a cellular surface protein domain or functional fragment thereof.

Embodiment 6

The recombinant masking protein of embodiment 5, wherein said cellular growth factor domain is a TNF domain.

Embodiment 7

The recombinant masking protein of embodiment 5, wherein said cellular surface protein domain is an Erbb receptor domain or a T cell receptor domain.

Embodiment 8

The recombinant masking protein of embodiment 7, wherein said Erbb receptor domain is a Her2 domain or EGFR domain.

Embodiment 9

The recombinant masking protein of embodiment 7, wherein said T cell receptor domain is a CTLA-4 domain.

Embodiment 10

The recombinant masking protein of one of embodiments 1-9, wherein said cleavable masking linker comprises a protease cleavage site.

Embodiment 11

The recombinant masking protein of embodiment 10, wherein said protease cleavage site is a matrix metalloprotease cleavage site, a disintegrin and metalloproteinase domain-containing (ADAM) metalloprotease cleavage site or a prostate specific antigen (PSA) protease cleavage site.

Embodiment 12

The recombinant masking protein of one of embodiments 1-11, wherein said recombinant masking protein is bound to a recombinant ligand protein comprising two identical ligand protein domains, each of said ligand protein domains comprising: (i) a ligand dimerizing domain; (ii) a ligand domain; bound to one of said ligand-masking domains; and (iii) a ligand linker connecting said ligand domain to said ligand dimerizing domain, wherein said ligand protein domains are bound together.

Embodiment 13

The recombinant masking protein of embodiment 12, wherein said ligand dimerizing domain is an Fc protein domain.

Embodiment 14

The recombinant masking protein of embodiment 13, wherein said Fc protein domain is an IgG$_1$ Fc protein.

Embodiment 15

The recombinant masking protein of one of embodiments 12-14, wherein said ligand domain is a cellular protein binding domain.

Embodiment 16

The recombinant masking protein of embodiment 15, wherein said cellular protein binding domain is a cellular growth factor binding domain or a cellular surface protein binding domain.

Embodiment 17

The recombinant masking protein of embodiment 16, wherein said cellular growth factor binding domain is a TNF receptor domain.

Embodiment 18

The recombinant masking protein of embodiment 16, wherein said cellular surface protein binding domain is an Erbb receptor binding domain or a T cell receptor binding domain.

Embodiment 19

The recombinant masking protein of embodiment 18, wherein said Erbb receptor binding domain is a Her2 binding domain or an EGFR binding domain.

Embodiment 20

The recombinant masking protein of embodiment 18, wherein said T cell receptor binding domain is a CTLA-4 binding domain.

Embodiment 21

The recombinant masking protein of embodiment 20, wherein said CTLA-4 binding domain is LCN2.

Embodiment 22

The recombinant masking protein of one of embodiments 12-21, wherein said ligand domain comprises a CDR domain.

Embodiment 23

The recombinant masking protein of one of embodiments 12-22, wherein said ligand domain is an antibody domain.

Embodiment 24

The recombinant masking protein of one of embodiments 1-23, wherein said masking-dimerizing domains connect to a targeting domain through a targeting linker.

Embodiment 25

The recombinant masking protein of embodiment 24, wherein said targeting domain is a single-chain variable fragment (scFv) domain.

Embodiment 26

The recombinant masking protein of embodiment 25, wherein said scFv domain is a hemaglutinin (HA) scFv domain.

Embodiment 27

The recombinant masking protein of embodiment 24, wherein said targeting linker is connected to the C-terminus of said masking dimerizing domain.

Embodiment 28

The recombinant masking protein of embodiment 27, wherein said cleavable masking linker is connected to the N-terminus of said masking dimerizing domain.

Embodiment 29

The recombinant masking protein of one of embodiments 24-28, wherein said targeting linker is a cleavable targeting linker.

Embodiment 30

The recombinant masking protein of embodiment 29, wherein said cleavable targeting linker comprises a protease cleavage site.

Embodiment 31

The recombinant masking protein of embodiment 30, wherein said protease is a matrix metalloprotease cleavage site, a disintegrin and metalloproteinase domain-containing (ADAM) metalloprotease cleavage site or a prostate specific antigen (PSA) protease cleavage site.

Embodiment 32

The recombinant masking protein of one of embodiments 12-31, wherein said ligand dimerizing domains connect to a targeting domain through a targeting linker.

Embodiment 33

The recombinant masking protein of embodiment 32, wherein said targeting domain is a single-chain variable fragment (scFv) domain.

Embodiment 34

The recombinant masking protein of embodiment 33, wherein said scFv domain is a hemaglutinin (HA) scFv domain.

Embodiment 35

The recombinant masking protein of embodiment 32, wherein said targeting linker is connected to the C-terminus of said ligand dimerizing domain.

Embodiment 36

The recombinant masking protein of embodiment 32, wherein said ligand linker is connected to the N-terminus of said ligand dimerizing domain.

Embodiment 37

The recombinant masking protein of embodiment 32, wherein said targeting linker is a cleavable targeting linker.

Embodiment 38

The recombinant masking protein of embodiment 37, wherein said cleavable targeting linker comprises a protease cleavage site.

Embodiment 39

The recombinant masking protein of embodiment 38, wherein said protease cleavage site is a matrix metalloprotease cleavage site, a disintegrin and metalloproteinase domain-containing (ADAM) metalloprotease cleavage site or a prostate specific antigen (PSA) protease cleavage site.

Embodiment 40

A method of treating a disease in a subject in need thereof, said method comprising administering to a subject a therapeutically effective amount of a recombinant masking protein comprising two identical masking protein domains, each of said masking protein domains comprising: (i) a masking dimerizing domain; (ii) a ligand-masking binding domain; and (iii) a cleavable masking linker connecting said ligand-masking binding domain to said masking dimerizing domain, wherein said masking protein domains are bound together; and a recombinant ligand protein comprising two identical ligand protein domains, each of said ligand protein domains comprising: (i) a ligand dimerizing domain; (ii) a ligand domain; and (iii) a ligand linker connecting said ligand domain to said ligand dimerizing domain, wherein said ligand protein domains are bound together.

Embodiment 41

The method of embodiment 40, wherein said recombinant masking protein and said recombinant ligand protein are administered to said subject simultaneously.

Embodiment 42

The method of embodiment 40, wherein said ligand domain is bound to at least one of said ligand-masking domains prior to said administering.

Embodiment 43

The method of embodiment 40, wherein said masking-dimerizing domains connect to a targeting domain through a targeting linker.

Embodiment 44

The method of embodiment 43, wherein said targeting linker is connected to the C-terminus of said masking dimerizing domain.

Embodiment 45

The method of embodiment 44, wherein said cleavable masking linker is connected to the N-terminus of said masking dimerizing domain.

Embodiment 46

The method of embodiment 43, wherein said targeting linker is a cleavable targeting linker.

Embodiment 47

The method of embodiment 40, wherein said ligand dimerizing domains connect to a targeting domain through a targeting linker.

Embodiment 48

The method of embodiment 47, wherein said targeting linker is connected to the C-terminus of said ligand dimerizing domain.

Embodiment 49

The method of embodiment 48, wherein said ligand linker is connected to the N-terminus of said ligand dimerizing domain.

Embodiment 50

The method of embodiment 47, wherein said targeting linker is a cleavable targeting linker.

Embodiment 51

The method of embodiment 40, wherein said disease is cancer, an autoimmune disease, a neurodegenerative disease or a cardiovascular disease.

Embodiment 52

The method of embodiment 51, wherein said cancer is leukemia, lymphoma, head and neck cancer, colorectal cancer, prostate cancer, melanoma, breast cancer or neuroblastoma.

Embodiment 53

The method of embodiment 51, wherein said autoimmune disease is Crohn's disease, rheumatoid arthritis, asthma or psoriasis.

Embodiment 54

The method of embodiment 51, wherein said neurodegenerative disease is Alzheimer's Disease or multiple sclerosis.

Embodiment 55

A pharmaceutical composition comprising a pharmaceutically acceptable excipient and a recombinant masking protein comprising two identical masking protein domains, each of said masking protein domains comprising: (i) a masking dimerizing domain; (ii) a ligand-masking binding domain; and (iii) a cleavable masking linker connecting said ligand-masking binding domain to said masking dimerizing domain, wherein said masking protein domains are bound together; and a recombinant ligand protein comprising two identical ligand protein domains, each of said ligand protein domains comprising: (i) a ligand dimerizing domain; (ii) a ligand domain; and (iii) a ligand linker connecting said ligand domain to said ligand dimerizing domain, wherein said ligand protein domains are bound together.

Embodiment 56

The pharmaceutical composition of embodiment 55, wherein said ligand domain is bound to one of said ligand-masking domains.

Embodiment 57

The pharmaceutical composition of embodiment 55, wherein said masking-dimerizing domains connect to a targeting domain through a targeting linker.

Embodiment 58

The pharmaceutical composition of embodiment 57, wherein said targeting linker is connected to the C-terminus of said masking dimerizing domain.

Embodiment 59

The pharmaceutical composition of embodiment 58, wherein said cleavable masking linker is connected to the N-terminus of said masking dimerizing domain.

Embodiment 60

The pharmaceutical composition of embodiment 57, wherein said targeting linker is a cleavable targeting linker.

Embodiment 61

The pharmaceutical composition of embodiment 55, wherein said ligand dimerizing domains connect to a targeting domain through a targeting linker.

Embodiment 62

The pharmaceutical composition of embodiment 61, wherein said targeting linker is connected to the C-terminus of said ligand dimerizing domain.

Embodiment 63

The pharmaceutical composition of embodiment 62, wherein said ligand linker is connected to the N-terminus of said ligand dimerizing domain.

Embodiment 64

The pharmaceutical composition of embodiment 61, wherein said targeting linker is a cleavable targeting linker.

Embodiment 65

A kit comprising: (A) a recombinant masking protein comprising two identical masking protein domains, each of said masking protein domains comprising: (i) a masking dimerizing domain; (ii) a ligand-masking binding domain; and (iii) a cleavable masking linker connecting said ligand-masking binding domain to said masking dimerizing domain, wherein said masking protein domains are bound together; and (B) a recombinant ligand protein comprising two identical ligand protein domains, each of said ligand protein domains comprising: (i) a ligand dimerizing domain; (ii) a ligand domain; and (iii) a ligand linker connecting said ligand domain to said ligand dimerizing domain, wherein said ligand protein domains are bound together.

Embodiment 66

The kit of embodiment 65, wherein said recombinant masking protein and said recombinant ligand protein are in one container.

Embodiment 67

The kit of embodiment 66, wherein said ligand domain is bound to one of said ligand-masking domains.

Embodiment 68

The kit of embodiment 65, wherein said recombinant masking protein and said recombinant ligand protein are in separate containers.

What is claimed is:

1. A recombinant masking protein comprising two identical masking protein domains, each of said masking protein domains comprising: (i) a masking dimerizing domain, wherein the masking dimerizing domain is an Fc protein domain;
   (ii) a ligand-masking binding domain comprising a human CTLA 4 polypeptide that binds to lipocalin 2, ipilimumab, or tremelimumab;

and (iii) a cleavable masking linker comprising a tumor associated protease cleavage site connecting said ligand-masking binding domain to said masking dimerizing domain, wherein said masking protein domains are bound together.

2. The recombinant masking protein of claim 1, wherein the human CTLA 4 polypeptide comprises an amino acid sequence selected from SEQ ID NOs 1-10, or a sequence having at least 90% identity to a sequence of SEQ ID NOs 1-10.

3. The recombinant masking protein of claim 1, wherein said protease cleavage site is a matrix metalloprotease cleavage site, a disintegrin and metalloproteinase domain-containing (ADAM) metalloprotease cleavage site or a prostate specific antigen (PSA) protease cleavage site.

4. The recombinant masking protein of claim 1, wherein said recombinant masking protein is bound to a recombinant ligand protein comprising two identical ligand protein domains, each of said ligand protein domains comprising:

(i) a ligand dimerizing domain, wherein the ligand dimerizing domain is an Fc protein domain;

(ii) a ligand domain comprising a T cell receptor binding domain selected from a lipocalin 2 polypeptide or an anti-CTLA4 antibody directed against human CTLA4; bound to one of said ligand-masking domains; and (iii) a ligand linker comprising a tumor associated protease cleavage site connecting said ligand domain to said ligand dimerizing domain, wherein said ligand protein domains are bound together.

5. The recombinant masking protein of claim 4, wherein said ligand domain is a lipocalin 2 polypeptide comprising SEQ ID NO: 15 or a sequence having at least 90% identity to a sequence of SEQ ID NO: 15.

6. The recombinant masking protein of claim 4, wherein said ligand domain is an ipilimumab antibody, a tremelimumab antibody, or a CTLA4 binding fragment thereof.

7. A method of treating a cancer in a subject in need thereof, said method comprising administering to the subject a therapeutically effective amount of a recombinant masking protein comprising two identical masking protein domains, each of said masking protein domains comprising:

(i) a masking dimerizing domain, wherein the masking dimerizing domain is an Fc protein domain;

(ii) a ligand-masking binding domain comprising a human CTLA-4 polypeptide that binds to lipocalin 2, ipilimumab, or tremelimumab; and (iii) a cleavable masking linker comprising a tumor associated protease cleavage site connecting said ligand-masking binding domain to said masking dimerizing domain, wherein said masking protein domains are bound together; and a recombinant ligand protein comprising two identical ligand protein domains, each of said ligand protein domains comprising:

(i) a ligand dimerizing domain, wherein the ligand dimerizing domain is an Fc protein domain;

(ii) a ligand domain comprising a T cell receptor binding domain selected from a lipocalin 2 polypeptide or an anti-CTLA4 antibody directed against human CTLA4; and (iii) a ligand linker comprising a tumor associated protease cleavage site connecting said ligand domain to said ligand dimerizing domain, wherein said ligand protein domains are bound together.

8. The method of claim 7, wherein said cancer is prostate cancer.

9. A pharmaceutical composition comprising a pharmaceutically acceptable excipient and a recombinant masking protein comprising two identical masking protein domains, each of said masking protein domains comprising:

(i) a masking dimerizing domain, wherein the masking dimerizing domain is an Fc protein domain;

(ii) a ligand-masking binding domain comprising a human CTLA 4 polypeptide that binds to lipocalin 2, ipilimumab, or tremelimumab; and (iii) a cleavable masking linker comprising a tumor associated protease cleavage site connecting said ligand-masking binding domain to said masking dimerizing domain, wherein said masking protein domains are bound together; and a recombinant ligand protein comprising two identical ligand protein domains, each of said ligand protein domains comprising:

(i) a ligand dimerizing domain, wherein the ligand dimerizing domain is an Fc protein domain;

(ii) a ligand domain comprising a T cell receptor binding domain selected from a lipocalin 2 polypeptide or an anti-CTLA4 antibody directed against human CTLA4; and (iii) a ligand linker comprising a tumor associated protease cleavage site connecting said ligand domain to said ligand dimerizing domain, wherein said ligand protein domains are bound together.

10. The recombinant masking protein of claim 4, wherein said ligand domain is a lipocalin 2 polypeptide consisting of SEQ ID NO: 15 or a sequence having at least 90% identity to a sequence of SEQ ID NO: 15.

* * * * *

UNITED STATES PATENT AND TRADEMARK OFFICE
CERTIFICATE OF CORRECTION

| | |
|---|---|
| PATENT NO. | : 11,279,752 B2 |
| APPLICATION NO. | : 16/559561 |
| DATED | : March 22, 2022 |
| INVENTOR(S) | : John C. Williams, Ulrich Rodeck and Kurt Jenkins |

Page 1 of 1

It is certified that error appears in the above-identified patent and that said Letters Patent is hereby corrected as shown below:

In the Specification

At Column 1, Line 19, after the "STATEMENT AS TO RIGHTS TO INVENTIONS MADE UNDER FEDERALLY SPONSORED RESEARCH AND DEVELOPMENT", please replace with the following paragraph:
This invention was made with government support under R21 CA135216 and P30 CA033572 awarded by the National Institutes of Health. The government has certain rights in the invention.

Signed and Sealed this
Twentieth Day of August, 2024

Katherine Kelly Vidal
*Director of the United States Patent and Trademark Office*

SEQUENCE LISTING

```
<160> NUMBER OF SEQ ID NOS: 16

<210> SEQ ID NO 1
<211> LENGTH: 385
<212> TYPE: PRT
<213> ORGANISM: Homo sapiens

<400> SEQUENCE: 1

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45
```

```
Ala Ala Thr Tyr Met Met Gly Asn Glu Leu Thr Phe Leu Asp Asp Ser
     50                  55                  60

Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gly Ser Arg Ser
            115                 120                 125

Gly Gly Thr Ser Gly Gly Gly Ser Val Pro Leu Ser Leu Tyr Ser Gly
        130                 135                 140

Ser Thr Ser Gly Ser Gly Lys Ser Ser Glu Gly Ser Gly Gln Ala Ser
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
            195                 200                 205

Pro Glu Val Lys Phe Asn Trp Tyr Val Asp Gly Val Glu Val His Asn
210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Pro Ile Glu Lys
            260                 265                 270

Thr Ile Ser Lys Ala Lys Gly Gln Pro Arg Glu Pro Gln Val Tyr Thr
            275                 280                 285

Leu Pro Pro Ser Arg Asp Glu Leu Thr Lys Asn Gln Val Ser Leu Thr
        290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
    370                 375                 380

Lys
385

<210> SEQ ID NO 2
<211> LENGTH: 385
<212> TYPE: PRT
<213> ORGANISM: Artificial sequence
<220> FEATURE:
<223> OTHER INFORMATION: Synthetic polypeptide

<400> SEQUENCE: 2

Met His Val Ala Gln Pro Ala Val Val Leu Ala Ser Ser Arg Gly Ile
 1               5                  10                  15
```

```
Ala Ser Phe Val Cys Glu Tyr Ala Ser Pro Gly Lys Ala Thr Ala Val
                20                  25                  30

Ala Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gly Ser Arg Ser
        115                 120                 125

Gly Gly Thr Ser Gly Gly Ser Val Pro Leu Ser Leu Tyr Ser Gly
        130                 135                 140

Ser Thr Ser Gly Ser Gly Lys Ser Ser Glu Gly Ser Gly Gln Ala Ser
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205

Pro Glu Val Lys Phe Asn Trp Tyr Val Asp Gly Val Glu Val His Asn
    210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Pro Ile Glu Lys
            260                 265                 270

Thr Ile Ser Lys Ala Lys Gly Gln Pro Arg Glu Pro Gln Val Tyr Thr
        275                 280                 285

Leu Pro Pro Ser Arg Asp Glu Leu Thr Lys Asn Gln Val Ser Leu Thr
    290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
    370                 375                 380

Lys
385

<210> SEQ ID NO 3
<211> LENGTH: 385
<212> TYPE: PRT
<213> ORGANISM: Artificial sequence
<220> FEATURE:
<223> OTHER INFORMATION: Synthetic polypeptide
```

<400> SEQUENCE: 3

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Ser Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gly Ser Arg Ser
        115                 120                 125

Gly Gly Thr Ser Gly Gly Ser Val Pro Leu Ser Leu Tyr Ser Gly
    130                 135                 140

Ser Thr Ser Gly Ser Gly Lys Ser Ser Glu Gly Ser Gly Gln Ala Ser
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205

Pro Glu Val Lys Phe Asn Trp Tyr Val Asp Gly Val Glu Val His Asn
    210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Pro Ile Glu Lys
            260                 265                 270

Thr Ile Ser Lys Ala Lys Gly Gln Pro Arg Glu Pro Gln Val Tyr Thr
        275                 280                 285

Leu Pro Pro Ser Arg Asp Glu Leu Thr Lys Asn Gln Val Ser Leu Thr
    290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
    370                 375                 380

Lys
385
```

```
<210> SEQ ID NO 4
<211> LENGTH: 385
<212> TYPE: PRT
<213> ORGANISM: Artificial sequence
<220> FEATURE:
<223> OTHER INFORMATION: Synthetic polypeptide

<400> SEQUENCE: 4

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Lys Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gly Ser Arg Ser
        115                 120                 125

Gly Gly Thr Ser Gly Gly Gly Ser Val Pro Leu Ser Leu Tyr Ser Gly
    130                 135                 140

Ser Thr Ser Gly Ser Gly Lys Ser Ser Glu Gly Ser Gly Gln Ala Ser
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205

Pro Glu Val Lys Phe Asn Trp Tyr Val Asp Gly Val Glu Val His Asn
    210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Pro Ile Glu Lys
            260                 265                 270

Thr Ile Ser Lys Ala Lys Gly Gln Pro Arg Glu Pro Gln Val Tyr Thr
        275                 280                 285

Leu Pro Pro Ser Arg Asp Glu Leu Thr Lys Asn Gln Val Ser Leu Thr
    290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
```

370                 375                 380
Lys
385

<210> SEQ ID NO 5
<211> LENGTH: 385
<212> TYPE: PRT
<213> ORGANISM: Artificial sequence
<220> FEATURE:
<223> OTHER INFORMATION: Synthetic polypeptide

<400> SEQUENCE: 5

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Arg Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gly Ser Arg Ser
        115                 120                 125

Gly Gly Thr Ser Gly Gly Gly Ser Val Pro Leu Ser Leu Tyr Ser Gly
    130                 135                 140

Ser Thr Ser Gly Ser Gly Lys Ser Ser Glu Gly Ser Gly Gln Ala Ser
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205

Pro Glu Val Lys Phe Asn Trp Tyr Val Asp Gly Val Glu Val His Asn
    210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Pro Ile Glu Lys
            260                 265                 270

Thr Ile Ser Lys Ala Lys Gly Gln Pro Arg Glu Pro Gln Val Tyr Thr
        275                 280                 285

Leu Pro Pro Ser Arg Asp Glu Leu Thr Lys Asn Gln Val Ser Leu Thr
    290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys

```
            340                 345                 350
Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
        370                 375                 380

Lys
385

<210> SEQ ID NO 6
<211> LENGTH: 385
<212> TYPE: PRT
<213> ORGANISM: Artificial sequence
<220> FEATURE:
<223> OTHER INFORMATION: Synthetic polypeptide

<400> SEQUENCE: 6

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Ser Val
            20                  25                  30

Glu Val Thr Val Leu Arg Gln Ala Asp Ser Gln Val Thr Glu Val Cys
        35                  40                  45

Ala Ala His Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gly Ser Arg Ser
        115                 120                 125

Gly Gly Thr Ser Gly Gly Gly Ser Val Pro Leu Ser Leu Tyr Ser Gly
    130                 135                 140

Ser Thr Ser Gly Ser Gly Lys Ser Ser Glu Gly Ser Gly Gln Ala Ser
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205

Pro Glu Val Lys Phe Asn Trp Tyr Val Asp Gly Val Glu Val His Asn
    210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Pro Ile Glu Lys
            260                 265                 270

Thr Ile Ser Lys Ala Lys Gly Gln Pro Arg Glu Pro Gln Val Tyr Thr
        275                 280                 285

Leu Pro Pro Ser Arg Asp Glu Leu Thr Lys Asn Gln Val Ser Leu Thr
    290                 295                 300

Cys Leu Val Lys Gly Phe Tyr Pro Ser Asp Ile Ala Val Glu Trp Glu
```

305                 310                 315                 320

Ser Asn Gly Gln Pro Glu Asn Asn Tyr Lys Thr Thr Pro Pro Val Leu
                    325                 330                 335

Asp Ser Asp Gly Ser Phe Phe Leu Tyr Ser Lys Leu Thr Val Asp Lys
                340                 345                 350

Ser Arg Trp Gln Gln Gly Asn Val Phe Ser Cys Ser Val Met His Glu
                355                 360                 365

Ala Leu His Asn His Tyr Thr Gln Lys Ser Leu Ser Leu Ser Pro Gly
            370                 375                 380

Lys
385

<210> SEQ ID NO 7
<211> LENGTH: 385
<212> TYPE: PRT
<213> ORGANISM: Artificial sequence
<220> FEATURE:
<223> OTHER INFORMATION: Synthetic polypeptide

<400> SEQUENCE: 7

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala His Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Leu Gly Ile Gly Asn Gly Thr Gln Ile
                100                 105                 110

Tyr Val Ile Asp Pro Glu Pro Cys Pro Asp Ser Asp Gly Ser Arg Ser
            115                 120                 125

Gly Gly Thr Ser Gly Gly Gly Ser Val Pro Leu Ser Leu Tyr Ser Gly
        130                 135                 140

Ser Thr Ser Gly Ser Gly Lys Ser Ser Glu Gly Ser Gly Gln Ala Ser
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205

Pro Glu Val Lys Phe Asn Trp Tyr Val Asp Gly Val Glu Val His Asn
        210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Pro Ile Glu Lys
            260                 265                 270

Thr Ile Ser Lys Ala Lys Gly Gln Pro Arg Glu Pro Gln Val Tyr Thr

```
            275                 280                 285
Leu Pro Pro Ser Arg Asp Glu Leu Thr Lys Asn Gln Val Ser Leu Thr
    290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
    370                 375                 380

Lys
385

<210> SEQ ID NO 8
<211> LENGTH: 385
<212> TYPE: PRT
<213> ORGANISM: Artificial sequence
<220> FEATURE:
<223> OTHER INFORMATION: Synthetic polypeptide

<400> SEQUENCE: 8

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Ala Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gly Ser Arg Ser
        115                 120                 125

Gly Gly Thr Ser Gly Gly Gly Ser Val Pro Leu Ser Leu Tyr Ser Gly
    130                 135                 140

Ser Thr Ser Gly Ser Gly Lys Ser Ser Glu Gly Ser Gly Gln Ala Ser
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205

Pro Glu Val Lys Phe Asn Trp Tyr Val Asp Gly Val Glu Val His Asn
    210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
```

```
                      245                 250                 255
Tyr Lys Cys Lys Val Ser Asn Lys Ala Leu Pro Ala Pro Ile Glu Lys
                260                 265                 270

Thr Ile Ser Lys Ala Lys Gly Gln Pro Arg Glu Pro Gln Val Tyr Thr
            275                 280                 285

Leu Pro Pro Ser Arg Asp Glu Leu Thr Lys Asn Gln Val Ser Leu Thr
        290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
    370                 375                 380

Lys
385

<210> SEQ ID NO 9
<211> LENGTH: 384
<212> TYPE: PRT
<213> ORGANISM: Artificial sequence
<220> FEATURE:
<223> OTHER INFORMATION: Synthetic polypeptide

<400> SEQUENCE: 9

His Val Ala Gln Pro Ala Val Val Leu Ala Ser Ser Arg Gly Ile Ala
1               5                   10                  15

Ser Phe Val Cys Glu Tyr Ala Ser Pro Gly Lys Ala Thr Glu Val Arg
            20                  25                  30

Val Thr Val Leu Arg Gln Ala Asp Ser Gln Val Thr Glu Val Cys Ala
        35                  40                  45

Ala Thr Tyr Met Met Gly Asn Glu Leu Thr Phe Leu Asp Asp Ser Ile
    50                  55                  60

Cys Thr Gly Thr Ser Ser Gly Asn Gln Val Asn Leu Thr Ile Gln Gly
65                  70                  75                  80

Leu Arg Ala Met Asp Thr Gly Leu Tyr Ile Cys Lys Val Ala Leu Met
                85                  90                  95

Tyr Pro Pro Pro Tyr Tyr Leu Gly Ile Gly Asn Gly Thr Gln Ile Tyr
            100                 105                 110

Val Ile Asp Pro Glu Pro Cys Pro Asp Ser Asp Gly Ser Arg Ser Gly
        115                 120                 125

Gly Thr Ser Gly Gly Gly Ser Val Pro Leu Ser Leu Tyr Ser Gly Ser
    130                 135                 140

Thr Ser Gly Ser Gly Lys Ser Ser Glu Gly Ser Gly Gln Ala Ser Thr
145                 150                 155                 160

His Thr Cys Pro Pro Cys Pro Ala Pro Glu Leu Leu Gly Gly Pro Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser His Glu Asp Pro
        195                 200                 205

Glu Val Lys Phe Asn Trp Tyr Val Asp Gly Val Glu Val His Asn Ala
```

```
                  210                 215                 220
Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
                260                 265                 270

Ile Ser Lys Ala Lys Gly Gln Pro Arg Glu Pro Gln Val Tyr Thr Leu
                275                 280                 285

Pro Pro Ser Arg Asp Glu Leu Thr Lys Asn Gln Val Ser Leu Thr Cys
                290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
                340                 345                 350

Arg Trp Gln Gln Gly Asn Val Phe Ser Cys Ser Val Met His Glu Ala
                355                 360                 365

Leu His Asn His Tyr Thr Gln Lys Ser Leu Ser Leu Ser Pro Gly Lys
                370                 375                 380

<210> SEQ ID NO 10
<211> LENGTH: 385
<212> TYPE: PRT
<213> ORGANISM: Artificial sequence
<220> FEATURE:
<223> OTHER INFORMATION: Synthetic polypeptide

<400> SEQUENCE: 10

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
                35                  40                  45

Ala Ala Thr Tyr Met Met Gly Asn Glu Leu Thr Phe Leu Asp Asp Ser
                50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Ala Val Ala Leu
                85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp Gly Ser Arg Ser
                115                 120                 125

Gly Gly Thr Ser Gly Gly Gly Ser Val Pro Leu Ser Leu Tyr Ser Gly
                130                 135                 140

Ser Thr Ser Gly Ser Gly Lys Ser Ser Glu Gly Ser Gly Gln Ala Ser
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
                180                 185                 190

Arg Thr Pro Glu Val Thr Cys Val Val Val Asp Val Ser His Glu Asp
```

```
                195                 200                 205
Pro Glu Val Lys Phe Asn Trp Tyr Val Asp Gly Val Glu Val His Asn
210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Pro Ile Glu Lys
                260                 265                 270

Thr Ile Ser Lys Ala Lys Gly Gln Pro Arg Glu Pro Gln Val Tyr Thr
            275                 280                 285

Leu Pro Pro Ser Arg Asp Glu Leu Thr Lys Asn Gln Val Ser Leu Thr
290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
                340                 345                 350

Ser Arg Trp Gln Gln Gly Asn Val Phe Ser Cys Ser Val Met His Glu
            355                 360                 365

Ala Leu His Asn His Tyr Thr Gln Lys Ser Leu Ser Leu Ser Pro Gly
370                 375                 380

Lys
385

<210> SEQ ID NO 11
<211> LENGTH: 360
<212> TYPE: PRT
<213> ORGANISM: Artificial sequence
<220> FEATURE:
<223> OTHER INFORMATION: Synthetic polypeptide

<400> SEQUENCE: 11

Cys Ser Gln Phe Leu Arg Gly Gln Glu Cys Val Glu Glu Cys Arg Val
1               5                   10                  15

Leu Gln Gly Leu Pro Arg Glu Tyr Val Asn Ala Arg His Cys Leu Pro
            20                  25                  30

Cys His Pro Glu Cys Gln Pro Gln Asn Gly Ser Val Thr Cys Phe Gly
        35                  40                  45

Pro Glu Ala Asp Gln Cys Val Ala Cys Ala His Tyr Lys Asp Pro Pro
50                  55                  60

Phe Cys Val Ala Arg Cys Pro Ser Gly Val Lys Pro Asp Leu Ser Tyr
65                  70                  75                  80

Met Pro Ile Trp Lys Phe Pro Asp Glu Glu Gly Ala Cys Gln Pro Cys
                85                  90                  95

Pro Ile Asn Gly Ser Arg Ser Gly Gly Thr Ser Gly Gly Gly Ser Val
            100                 105                 110

Pro Leu Ser Leu Tyr Ser Gly Ser Thr Ser Gly Ser Gly Lys Ser Ser
        115                 120                 125

Glu Gly Ser Gly Gln Ala Ser Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
```

```
                165                 170                 175
Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 12
<211> LENGTH: 360
<212> TYPE: PRT
<213> ORGANISM: Artificial sequence
<220> FEATURE:
<223> OTHER INFORMATION: Synthetic polypeptide

<400> SEQUENCE: 12

Cys Ser Gln Phe Leu Arg Gly Gln Glu Cys Val Glu Glu Cys Arg Val
1               5                   10                  15

Leu Gln Gly Leu Pro Arg Glu Tyr Val Asn Ala Arg His Cys Leu Pro
            20                  25                  30

Cys His Pro Glu Cys Gln Pro Gln Asn Gly Ser Val Thr Cys Phe Gly
        35                  40                  45

Pro Glu Ala Asp Gln Cys Val Ala Cys Ala His Tyr Lys Asp Pro Pro
    50                  55                  60

Phe Cys Val Ala Arg Cys Pro Ser Gly Val Lys Pro Asp Leu Ser Tyr
65                  70                  75                  80

Met Pro Ile Trp Lys Phe Pro Asp Glu Glu Gly Ala Cys Gln Pro Cys
                85                  90                  95

Pro Ile Asn Gly Ser Arg Ser Gly Gly Thr Ser Gly Gly Gly Ser Val
            100                 105                 110

Pro Gly Ser Gly Ser Ser Gly Ser Thr Ser Gly Ser Gly Lys Ser Ser
        115                 120                 125

Glu Gly Ser Gly Gln Ala Ser Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
```

```
                    165                 170                 175
Val Asp Val Ser His Glu Asp Pro Glu Val Lys Phe Asn Trp Tyr Val
                180                 185                 190

Asp Gly Val Glu Val His Asn Ala Lys Thr Lys Pro Arg Glu Glu Gln
            195                 200                 205

Tyr Asn Ser Thr Tyr Arg Val Val Ser Val Leu Thr Val Leu His Gln
        210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 13
<211> LENGTH: 713
<212> TYPE: PRT
<213> ORGANISM: Artificial sequence
<220> FEATURE:
<223> OTHER INFORMATION: Synthetic polypeptide

<400> SEQUENCE: 13

Met Arg Pro Ser Gly Thr Ala Gly Ala Ala Leu Leu Ala Leu Leu Ala
1               5                   10                  15

Ala Leu Cys Pro Ala Ser Arg Ala Arg Lys Val Cys Asn Gly Ile Gly
            20                  25                  30

Ile Gly Glu Phe Lys Asp Ser Leu Ser Ile Asn Ala Thr Asn Ile Lys
        35                  40                  45

His Phe Lys Asn Cys Thr Ser Ile Ser Gly Asp Leu His Ile Leu Pro
    50                  55                  60

Val Ala Phe Arg Gly Asp Ser Phe Thr His Thr Pro Pro Leu Asp Pro
65                  70                  75                  80

Gln Glu Leu Asp Ile Leu Lys Thr Val Lys Glu Ile Thr Gly Phe Leu
                85                  90                  95

Leu Ile Ala Ala Trp Pro Glu Asn Arg Thr Asp Leu His Ala Phe Glu
            100                 105                 110

Asn Leu Glu Ile Ile Arg Gly Arg Thr Asn Met Asp Gly Gln Phe Ser
        115                 120                 125

Leu Ala Val Val Ser Leu Asn Ile Thr Ser Leu Gly Leu Arg Ser Leu
    130                 135                 140

Lys Glu Ile Ser Asp Gly Asp Val Ile Ile Ser Gly Asn Lys Asn Leu
145                 150                 155                 160

Cys Tyr Ala Asn Thr Ile Asn Trp Lys Lys Leu Phe Gly Thr Ser Gly
```

```
                165                 170                 175
Gln Lys Thr Lys Ile Ile Ser Asn Arg Gly Glu Asn Ser Cys Lys Ala
            180                 185                 190

Thr Gly Gln Val Cys His Ala Leu Cys Ser Pro Glu Gly Cys Trp Gly
            195                 200                 205

Pro Glu Pro Lys Asp Cys Val Ser Cys Arg Asn Val Ser Arg Gly Arg
            210                 215                 220

Glu Cys Ser Arg Gly Gly Ser Gly Gly Ser Gly Gly Gly Ser
225                 230                 235                 240

Val Pro Leu Ser Leu Tyr Ser Gly Ser Thr Gly Ser Gly Lys Ser
                245                 250                 255

Ser Glu Gly Ser Gly Ser Gly Ala Gln Val Gln Leu Lys Gln Ser Gly
                260                 265                 270

Pro Gly Leu Val Gln Pro Ser Gln Ser Leu Ser Ile Thr Cys Thr Val
            275                 280                 285

Ser Gly Phe Ser Leu Thr Asn Tyr Gly Val His Trp Val Arg Gln Ser
            290                 295                 300

Pro Gly Lys Gly Leu Glu Trp Leu Gly Val Ile Trp Ser Gly Gly Asn
305                 310                 315                 320

Thr Asp Tyr Asn Thr Pro Phe Thr Ser Arg Leu Ser Ile Asn Lys Asp
                325                 330                 335

Asn Ser Lys Ser Gln Val Phe Phe Lys Met Asn Ser Leu Gln Ser Asn
                340                 345                 350

Asp Thr Ala Ile Tyr Tyr Cys Ala Arg Ala Leu Thr Tyr Tyr Asp Tyr
            355                 360                 365

Glu Phe Ala Tyr Trp Gly Gln Gly Thr Leu Val Thr Val Ser Ala Ala
            370                 375                 380

Ser Thr Lys Gly Pro Ser Val Phe Pro Leu Ala Pro Ser Ser Lys Ser
385                 390                 395                 400

Thr Ser Gly Gly Thr Ala Ala Leu Gly Cys Leu Val Lys Asp Tyr Phe
                405                 410                 415

Pro Glu Pro Val Thr Val Ser Trp Asn Ser Gly Ala Leu Thr Ser Gly
            420                 425                 430

Val His Thr Phe Pro Ala Val Leu Gln Ser Ser Gly Leu Tyr Ser Leu
            435                 440                 445

Ser Ser Val Val Thr Val Pro Ser Ser Ser Leu Gly Thr Gln Thr Tyr
            450                 455                 460

Ile Cys Asn Val Asn His Lys Pro Ser Asn Thr Lys Val Asp Lys Arg
465                 470                 475                 480

Val Glu Pro Lys Ser Cys Asp Lys Thr His Thr Cys Pro Pro Cys Pro
                485                 490                 495

Ala Pro Glu Leu Leu Gly Gly Pro Ser Val Phe Leu Phe Pro Pro Lys
            500                 505                 510

Pro Lys Asp Thr Leu Met Ile Ser Arg Thr Pro Glu Val Thr Cys Val
            515                 520                 525

Val Val Asp Val Ser His Glu Asp Pro Glu Val Lys Phe Asn Trp Tyr
            530                 535                 540

Val Asp Gly Val Glu Val His Asn Ala Lys Thr Lys Pro Arg Glu Glu
545                 550                 555                 560

Gln Tyr Asn Ser Thr Tyr Arg Val Val Ser Val Leu Thr Val Leu His
                565                 570                 575

Gln Asp Trp Leu Asn Gly Lys Glu Tyr Lys Cys Lys Val Ser Asn Lys
            580                 585                 590
```

```
Ala Leu Pro Ala Pro Ile Glu Lys Thr Ile Ser Lys Ala Lys Gly Gln
            595                 600                 605

Pro Arg Glu Pro Gln Val Tyr Thr Leu Pro Pro Ser Arg Glu Glu Met
610                 615                 620

Thr Lys Asn Gln Val Ser Leu Thr Cys Leu Val Lys Gly Phe Tyr Pro
625                 630                 635                 640

Ser Asp Ile Ala Val Glu Trp Glu Ser Asn Gly Gln Pro Glu Asn Asn
                645                 650                 655

Tyr Lys Thr Thr Pro Pro Val Leu Asp Ser Asp Gly Ser Phe Phe Leu
            660                 665                 670

Tyr Ser Lys Leu Thr Val Asp Lys Ser Arg Trp Gln Gln Gly Asn Val
            675                 680                 685

Phe Ser Cys Ser Val Met His Glu Ala Leu His Asn His Tyr Thr Gln
690                 695                 700

Lys Ser Leu Ser Leu Ser Pro Gly Lys
705                 710

<210> SEQ ID NO 14
<211> LENGTH: 237
<212> TYPE: PRT
<213> ORGANISM: Artificial sequence
<220> FEATURE:
<223> OTHER INFORMATION: Synthetic polypeptide

<400> SEQUENCE: 14

Met Arg Pro Ser Gly Thr Ala Gly Ala Ala Leu Leu Ala Leu Leu Ala
1               5                   10                  15

Ala Leu Cys Pro Ala Ser Arg Ala Asp Ile Leu Leu Thr Gln Ser Pro
            20                  25                  30

Val Ile Leu Ser Val Ser Pro Gly Glu Arg Val Ser Phe Ser Cys Arg
        35                  40                  45

Ala Ser Gln Ser Ile Gly Thr Asn Ile His Trp Tyr Gln Gln Arg Thr
    50                  55                  60

Asn Gly Ser Pro Arg Leu Leu Ile Lys Tyr Ala Ser Glu Ser Ile Ser
65                  70                  75                  80

Gly Ile Pro Ser Arg Phe Ser Gly Ser Gly Ser Gly Thr Asp Phe Thr
                85                  90                  95

Leu Ser Ile Asn Ser Val Glu Ser Glu Asp Ile Ala Asp Tyr Tyr Cys
            100                 105                 110

Gln Gln Asn Asn Asn Trp Pro Thr Thr Phe Gly Ala Gly Thr Lys Leu
        115                 120                 125

Glu Leu Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Ala
225                 230                 235
```

```
<210> SEQ ID NO 15
<211> LENGTH: 178
<212> TYPE: PRT
<213> ORGANISM: Artificial sequence
<220> FEATURE:
<223> OTHER INFORMATION: Synthetic polypeptide

<400> SEQUENCE: 15

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Arg Ile Leu Arg Asp Asp Gln His Pro
        35                  40                  45

Met Asn Met Tyr Ala Thr Ile Tyr Glu Leu Lys Glu Asp Lys Ser Tyr
    50                  55                  60

Asn Val Thr Ser Val Ile Ser Ser His Lys Lys Cys Glu Tyr Thr Ile
65                  70                  75                  80

Ala Thr Phe Val Pro Gly Ser Gln Pro Gly Glu Phe Thr Leu Gly Asn
                85                  90                  95

Ile Lys Ser Tyr Gly Asp Lys Thr Ser Tyr Leu Val Arg Val Val Ser
            100                 105                 110

Thr Asp Tyr Asn Gln Tyr Ala Val Val Phe Phe Lys Leu Ala Glu Asp
            115                 120                 125

Asn Ala Glu Phe Phe Ala Ile Thr Ile Tyr Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 16
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 16

Val Pro Leu Ser Leu Tyr Ser
1               5
```